US012692241B2

(12) United States Patent
Inagaki et al.

(10) Patent No.: US 12,692,241 B2
(45) Date of Patent: Jul. 28, 2026

(54) SUBSTITUTED TRIAZINE COMPOUND

(71) Applicant: Nico Therapeutics, Inc., Chicago, IL (US)

(72) Inventors: Yusuke Inagaki, Tokyo (JP); Yumi Yamashita, Tokyo (JP); Hiroki Toya, Tokyo (JP); Takuya Washio, Tokyo (JP); Fumie Takahashi, Tokyo (JP); Kengo Saba, Tokyo (JP); Hiroshi Tomiyama, Nagano (JP); Yoshinori Iwai, Nagano (JP); Akihiko Nakamura, Nagano (JP)

(73) Assignee: Nico Therapeutics, Inc., Chicago, IL (US)

(*) Notice: Subject to any disclaimer, the term of this patent is extended or adjusted under 35 U.S.C. 154(b) by 397 days.

(21) Appl. No.: 18/288,588

(22) PCT Filed: Apr. 27, 2022

(86) PCT No.: PCT/JP2022/018994

§ 371 (c)(1),
(2) Date: Oct. 27, 2023

(87) PCT Pub. No.: WO2022/230912

PCT Pub. Date: Nov. 3, 2022

(65) Prior Publication Data

US 2024/0239758 A1     Jul. 18, 2024

(30) Foreign Application Priority Data

Apr. 28, 2021    (JP) ................................. 2021-075905

(51) Int. Cl.
| | | |
|---|---|---|
| *C07D 253/07* | (2006.01) |
| *C07D 211/56* | (2006.01) |
| *C07D 401/12* | (2006.01) |
| *C07D 401/14* | (2006.01) |
| *C07D 403/12* | (2006.01) |
| *C07D 405/12* | (2006.01) |
| *C07D 405/14* | (2006.01) |
| *C07D 407/14* | (2006.01) |
| *C07D 409/12* | (2006.01) |
| *C07D 413/12* | (2006.01) |
| *C07F 5/02* | (2006.01) |

(52) U.S. Cl.
CPC .......... *C07D 253/07* (2013.01); *C07D 211/56* (2013.01); *C07D 401/12* (2013.01); *C07D 401/14* (2013.01); *C07D 403/12* (2013.01); *C07D 405/12* (2013.01); *C07D 405/14* (2013.01); *C07D 407/14* (2013.01); *C07D 409/12* (2013.01); *C07D 413/12* (2013.01); *C07F 5/027* (2013.01)

(58) Field of Classification Search
CPC .. C07D 253/07; C07D 211/56; C07D 401/12;
C07D 403/12; C07D 405/12; C07D 407/14; C07D 409/12; C07D 413/12; C07D 401/14; C07D 405/14

See application file for complete search history.

(56) References Cited

U.S. PATENT DOCUMENTS

| | | | |
|---|---|---|---|
| 2020/0361898 A1 | 11/2020 | Farady et al. | |
| 2022/0048890 A1* | 2/2022 | Luzzio ................. | C07D 403/14 |
| 2023/0107277 A1 | 4/2023 | Inagaki et al. | |
| 2024/0391895 A1 | 11/2024 | Yu et al. | |
| 2025/0002470 A1 | 1/2025 | Xu et al. | |
| 2025/0152584 A1 | 5/2025 | Li et al. | |

FOREIGN PATENT DOCUMENTS

| | | |
|---|---|---|
| WO | 2011/133920 A1 | 10/2011 |
| WO | 2017/184604 A1 | 10/2017 |
| WO | 2018/015445 A1 | 1/2018 |
| WO | 2019/008025 A1 | 1/2019 |
| WO | 2019/191229 A1 | 10/2019 |
| WO | 2020/163248 A1 | 8/2020 |
| WO | 2020/231977 A1 | 11/2020 |
| WO | 2020/234715 A1 | 11/2020 |
| WO | 2021/193897 A1 | 9/2021 |
| WO | 2022/135567 A1 | 6/2022 |
| WO | 2022/238347 A1 | 11/2022 |
| WO | 2022/253936 A1 | 12/2022 |

(Continued)

OTHER PUBLICATIONS

Khoshneviszadeh et al., Design, synthesis and biological evaluation of novel anti-cytokine 1,2,4-triazine derivatives. Bioorg Med Chem. Nov. 1, 2013;21(21):6708-17.

(Continued)

*Primary Examiner* — Laura L Stockton

(74) *Attorney, Agent, or Firm* — McCarter & English, LLP; Wei Song; James M. Alburger

(57) ABSTRACT

An object of the present invention is to provide a pharmaceutical composition, particularly a compound suitable for preventing and/or treating an inflammatory disease and/or a neurodegenerative disease. The present inventors accomplished the present invention by conducting intensive studies to find a compound having an inhibitory effect on NLRP3 inflammasome activation, with the result that a substituted triazine compound is found to have the inhibitory effect on NLRP3 inflammasome activation. The substituted triazine compound of the present invention is expected to serve as a preventive and/or therapeutic drug for an inflammatory disease and/or a neurodegenerative disease.

8 Claims, No Drawings

(56)     References Cited

FOREIGN PATENT DOCUMENTS

| | | | |
|---|---|---|---|
| WO | 2023/003002 A1 | 1/2023 | |
| WO | 2023/028534 A1 | 3/2023 | |
| WO | WO-2023028536 A1 * | 3/2023 | ........... C07D 253/07 |
| WO | 2023/051761 A1 | 4/2023 | |
| WO | 2023/066377 A1 | 4/2023 | |
| WO | 2023/088856 A1 | 5/2023 | |
| WO | 2023/131277 A1 | 7/2023 | |
| WO | 2023/159148 A2 | 8/2023 | |
| WO | 2023/186020 A1 | 10/2023 | |

OTHER PUBLICATIONS

International Search Report and Written Opinion for Application No. PCT/JP2022/018994, dated Jul. 19, 2022, 9 pages.
European Office Action for Application No. 22795825.3, dated Mar. 25, 2025, 11 pages.

* cited by examiner

SUBSTITUTED TRIAZINE COMPOUND

CROSS-REFERENCE TO RELATED APPLICATIONS

This application is a U.S. national stage application, filed under 35 U.S.C. § 371 (c), of International Application No. PCT/JP2022/018994, filed on Apr. 27, 2022, which claims priority to Japanese Patent Application No. 2021-075905, filed on Apr. 28, 2021.

TECHNICAL FIELD

The present invention relates to a substituted triazine compound or a salt thereof having an inhibitory effect on NLRP3 inflammasome activation and expected to be useful as an active ingredient of a pharmaceutical composition, for example, a pharmaceutical composition for preventing and/or treating an inflammatory disease or a neurodegenerative disease.

BACKGROUND ART

An inflammasome is an assembly of intracellular proteins induced from endogenic/exogenic alarm molecules and is a mechanism responsible for amplification of an inflammatory reaction caused by activation and induction of cell death, which are caused by cleavage of inflammatory cytokines IL-1β and IL-18 through activation of caspase 1. As the molecule recognizing alarm molecules, a plurality of types of molecules are known, which include NLRP1, NLRP3, NLRC4 and AIM2. NLRP3 is activated by recognizing cellular stress caused by, e.g., an extracellular ATP molecule, a toxin of a pathogen, a crystal of uric acid or cholesterol, and abnormal aggregation of a protein(s).

As a disease caused by gain-of-function mutation of NLRP3, Cryopyrin-associated periodic syndrome (CAPS) is known (Nature Genetics, Vol. 29, No. 3, page 301-305, 2001). Also, it is reported that NLRP3 inflammasome is activated or highly expressed in a wide variety of diseases such as gout (Arthritis Research and Therapy, Vol. 12, No. 2, Article No. 206, 2010), non-alcoholic steatohepatitis (Journal of Molecular Medicine, Vol. 92, No. 10, page 1069-1082, 2014), inflammatory bowel disease (Gut, Vol. 59, No. 9, page 1192-1100, 2010), Alzheimer's disease (Nature, Vol. 493, No. 7434, page 674-678, 2013), Parkinson's disease (PLoS ONE, Vol. 8, No. 1, Article No. e55375, 2013), amyotrophic lateral sclerosis (Inflammation, Vol. 41, No. 1, page 93-103, 2018) and multiple system atrophy (Journal of Neuropathology and Experimental Neurology, Vol. 77, No. 11, page 1055-1065, 2018).

Also, it is known that α-synuclein fibers activate NLRP3 to promote IL-1β production from microglia; and that administration of NLRP3 inhibitors improve functions in a mouse model having α-synucleinopathy induced by α-synuclein fibers (Science Translational Medicine, Vol. 10, Article No. eaah4066, 2018).

PTL 1 discloses that compounds represented by the following formula have an inhibitory effect on NLRP3 inflammasome activation (for the reference symbols in the formula, see, the publication).

[Chem 1]

PTL2 discloses that compounds represented by the following formula have an inhibitory effect on NLRP3 inflammasome activation (for the reference symbols in the formula, see, the publication).

[Chem 2]

PTL3 discloses that compounds represented by the following formula have an inhibitory effect on NLRP3 inflammasome activation (for the reference symbols in the formula, see, the publication).

[Chem 3]

PTL4 discloses that compounds represented by the following formula have an inhibitory effect on NLRP3 inflammasome activation (for the reference symbols in the formula, see, the publication).

[Chem 4]

PTL5, which is published after the priority date of the present application, discloses that compounds represented by the following formula have an inhibitory effect on NLRP3 inflammasome activation (for the reference symbols in the formula, see, the publication).

[Chem 5]

Also, PTL6 discloses that compounds represented by the following formula are useful in treatment of Huntington's disease (B represents a hetero ring, and for the other reference symbols in the formula, see, the publication).

[Chem 6]

PTL7 discloses that compounds represented by the following formula have a modulatory function on mRNA splicing (for the reference symbols in the formula, see, the publication).

[Chem 7]

PTL8 discloses that compounds represented by the following formula have a modulatory function on muscle contraction (for the reference symbols in the formula, see, the publication).

[Chem 8]

CITATION LIST

Patent Literature

PTL1: International Publication No. WO 2020/234715
PTL2: International Publication No. WO 2019/008025
PTL3: International Publication No. WO 2017/184604
PTL4: International Publication No. WO 2018/015445
PTL5: International Publication No. WO 2021/193897
PTL6: International Publication No. WO 2019/191229
PTL7: International Publication No. WO 2020/163248
PTL8: International Publication No. WO 2011/133920

SUMMARY OF INVENTION

Technical Problem

The invention provides a pharmaceutical composition, particularly a compound having an inhibitory effect on NLRP3 inflammasome activation and expected to be useful as an active ingredient of a pharmaceutical composition for preventing and/or treating, e.g., an inflammatory disease or a neurodegenerative disease.

Solution to Problem

The present inventors conducted intensive studies on a compound having an inhibitory effect on NLRP3 inflammasome activation. As a result, they found that a substituted triazine compound has an inhibitory effect on NLRP3 inflammasome activation and expected to be useful as an active ingredient of a pharmaceutical composition for preventing and/or treating, e.g., inflammatory disease and a neurodegenerative disease. Based on the finding, the present invention was accomplished.

More specifically, the present invention relates to a compound of formula (I) or a salt thereof, and a pharmaceutical composition comprising a compound of formula (I) or a salt thereof and one or more excipients.

[Chem 9]

wherein $R^1$ are the same or different from each other, and are $C_{1-6}$ alkyl, halogeno-$C_{1-6}$ alkyl, $C_{3-8}$ cycloalkyl, halogen, —O—$C_{1-6}$ alkyl, —O-halogeno-$C_{1-6}$ alkyl or cyano, $R^2$ is $C_{1-6}$ alkyl, $C_{3-8}$ cycloalkyl, halogeno-$C_{1-6}$ alkyl, —O—$C_{1-6}$ alkyl, —N($C_{1-6}$ alkyl)$_2$ or aryl, $R^3$ is H or $C_{1-6}$ alkyl, $R^4$ is $C_{1-6}$ alkyl substituted with the same or different one to four $R^5$, —$C_{1-6}$ alkylene-(aryl optionally substituted with the same or different one to four $R^6$), —$C_{1-6}$ alkylene-($C_{3-8}$ cycloalkyl optionally substituted with the same or different one to four $R^7$), —$C_{1-6}$ alkylene-(heteroaryl optionally substituted with the same or different one to four $R^8$), —$C_{1-6}$ alkylene-(4 to 7-membered saturated heterocyclyl optionally substituted with the same or different one to four $R^9$), $C_{3-8}$ cycloalkyl optionally substituted with the same or different one to four $R^{10}$, a heteroaryl optionally substituted with the same or different one to four $R^{11}$, or a 4 to 8-membered saturated heterocyclyl optionally substituted with the same or different one to four $R^{12}$, $R^5$ is —$OR^{13}$, —$NR^{14}R^{15}$, halogen or cyano, $R^6$ is $C_{1-6}$ alkyl, halogeno-$C_{1-6}$ alkyl, $C_{3-8}$ cycloalkyl, —$OR^{13}$, —$NR^{14}R^{15}$, —$C_{1-6}$ alkylene-$OR^{13}$, —$C_{1-6}$ alkylene-$NR^{14}R^{15}$, halogen or cyano, $R^7$ is $C_{1-6}$ alkyl, halogeno-$C_{1-6}$ alkyl, $C_{3-8}$ cycloalkyl, —$OR^{13}$, —$NR^{14}R^{15}$, —$C_{1-6}$ alkylene-$OR^{13}$, —$C_{1-6}$ alkylene-$NR^{14}R^{15}$, halogen or cyano, $R^8$ is $C_{1-6}$ alkyl, halogeno-$C_{1-6}$ alkyl, $C_{3-8}$ cycloalkyl, —$OR^{13}$, —$NR^{14}R^{15}$, —$C_{1-6}$ alkylene-$OR^{13}$, —$C_{1-6}$ alkylene-$NR^{14}R^{15}$, halogen or cyano, $R^9$ is $C_{1-6}$ alkyl, halogeno-$C_{1-6}$ alkyl, $C_{3-8}$ cycloalkyl, —$OR^{13}$, —$NR^{14}R^{15}$, —$C_{1-6}$ alkylene-$OR^{13}$, —$C_{1-6}$ alkylene-$NR^{14}R^{15}$, halogen, cyano, oxo, —C(O)—$C_{1-6}$ alkyl or —S(O)$_2$—$C_{1-6}$ alkyl, $R^{10}$ is $C_{1-6}$ alkyl, halogeno-$C_{1-6}$ alkyl, $C_{3-8}$ cycloalkyl, —$OR^{13}$, —$NR^{14}R^{15}$, —$C_{1-6}$ alkylene-$OR^{13}$, —$C_{1-6}$alkylene-$NR^{14}R^{15}$, halogen, —C(O)—OH or cyano, $R^{11}$ is $C_{1-6}$ alkyl, halogeno-$C_{1-6}$ alkyl, $C_{3-8}$ cycloalkyl, —$OR^{13}$, —$NR^{14}R^{15}$, —$C_{1-6}$ alkylene-$OR^{13}$, —$C_{1-6}$ alkylene-$NR^{14}R^{15}$, halogen or cyano, $R^{12}$ is $C_{1-6}$ alkyl, halogeno-$C_{1-6}$ alkyl, $C_{3-8}$ cycloalkyl, 4 to 7-membered saturated heterocyclyl, —$OR^{13}$, —$NR^{14}R^{15}$, —$C_{1-6}$ alkylene-$C_{3-8}$ cycloalkyl, —$C_{1-6}$ alkylene-$OR^{13}$, $C_{1-6}$ alkylene-$NR^{14}R^{15}$, —$C_{1-6}$ alkylene-cyano, —$C_{1-6}$ alkylene-C(O)—OH, halogen, cyano, oxo, —C(O)—$NH_2$, —C(O)—$C_{1-6}$ alkyl or —$S(O)_2$—$C_{1-6}$ alkyl, $R^{13}$ is H or $C_{1-6}$ alkyl, $R^{14}$ and $R^{15}$ are the same or different from each other, and are H, $C_{1-6}$ alkyl or —C(O)—$C_{1-6}$ alkyl, and n is an integer of 1 to 4 and represents the number of $R^1$ substituents.

Note that, unless otherwise specified, if the reference symbols of a chemical formula in the specification are used in another chemical formula, the same reference symbols express the same meanings.

The present invention relates to a pharmaceutical composition comprising a compound of formula (I) or a salt thereof and one or more pharmaceutically acceptable excipients, particularly, a pharmaceutical composition for preventing and/or treating an inflammatory disease or a neurodegenerative disease. Note that, the pharmaceutical composition includes a preventive and/or therapeutic agent comprising a compound of formula (I) or a salt thereof, for an inflammatory disease or a neurodegenerative disease.

The present invention relates to a compound of formula (I) or a salt thereof as an NLRP3 inflammasome activation inhibitor; a compound of formula (I) or a salt thereof to be used as an NLRP3 inflammasome activation inhibitor; an NLRP3 inflammasome activation inhibitor comprising a compound of formula (I) or a salt thereof; a pharmaceutical composition comprising a compound of formula (I) or a salt thereof and one or more pharmaceutically acceptable excipients, which is an NLRP3 inflammasome activation inhibitor; use of a compound of formula (I) or a salt thereof for the manufacture of a medicament or a pharmaceutical composition for preventing and/or treating an inflammatory disease and/or a neurodegenerative disease; use of a compound of formula (I) or a salt thereof for preventing and/or treating an inflammatory disease and/or a neurodegenerative disease; a compound of formula (I) or a salt thereof for use in preventing and/or treating an inflammatory disease and/or a neurodegenerative disease; and a method for preventing and/or treating an inflammatory disease and/or a neurodegenerative disease, comprising administering to a subject an effective amount of a compound of formula (I) or a salt thereof. Note that, the "subject" refers to a human or another animal requiring prevention and/or treatment of a disease as mentioned above; in an embodiment, is a human requiring prevention and/or treatment of a disease as mentioned above.

Advantageous Effects of Invention

A compound of formula (I) or a salt thereof has an inhibitory effect on NLRP3 inflammasome activation and can be used as a preventive and/or therapeutic drug for, e.g., an inflammatory disease and/or a neurodegenerative disease.

DESCRIPTION OF EMBODIMENTS

Now, the present invention will be more specifically described below.

In the specification, the following terms have the following meanings, unless otherwise specified. The following definitions are made to clearly determine the terms and not intended to limit them. If the terms used herein are not specifically defined, the terms are those used in senses ordinarily known to those skilled in the art.

In the specification, the "$C_{1-6}$ alkyl" refers to a linear or branched saturated hydrocarbon group having 1 to 6 carbon atoms (hereinafter simply referred to as $C_{1-6}$). Examples of the $C_{1-6}$ alkyl include methyl, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1,3-dimethylbutyl and 1-ethyl-2-methylpropyl. The $C_{1-6}$alkyl represents methyl, ethyl, n-propyl, n-butyl, isobutyl, tert-butyl or 2,2-dimethylpropyl as an embodiment. The $C_{1-6}$ alkyl represents a linear or branched $C_{1-4}$ alkyl as an embodiment; methyl, ethyl, n-propyl, n-butyl, isobutyl or tert-butyl as an embodiment; and n-propyl or isobutyl as an embodiment. The $C_{1-6}$ alkyl represents methyl, ethyl, n-propyl or isopropyl as another embodiment; methyl or isopropyl as an embodiment; isopropyl as an embodiment; and methyl as an embodiment.

The "$C_{1-6}$ alkylene" refers to a linear or branched $C_{1-6}$ divalent saturated hydrocarbon. Examples of the $C_{1-6}$ alkylene include methylene, ethylene, trimethylene, tetramethylene, pentamethylene, hexamethylene, methylmethylene, 2-methylethylene, 2,2-dimethylethylene, 2-methyltrimethylene, ethylethylene, 1,2-dimethylethylene and 1,1,2,2-tetramethylethylene. The $C_{1-6}$ alkylene represents $C_{1-4}$ alkylene as an embodiment; methylene or ethylene as an embodiment; ethylene as an embodiment; and methylene as another embodiment.

The "$C_{3-8}$ cycloalkyl" refers to a $C_{3-8}$ saturated cyclic hydrocarbon group, which may have a crosslink and form a spiro ring. Examples of the $C_{3-8}$ cycloalkyl include cyclopropyl, cyclobutyl, cyclopentyl, cyclohexyl, cycloheptyl, cyclooctyl, bicyclo[1.1.1]pentyl, bicyclo[3.1.0]hexyl, bicyclo[2.2.1]heptyl, bicyclo[3.1.1]heptyl, bicyclo[3.3.0]octyl, spiro [2.2]pentyl, spiro [3.3]heptyl and spiro [2.5]octyl. The $C_{3-8}$ cycloalkyl represents cyclopropyl, cyclobutyl, cyclopentyl, cyclohexyl, cycloheptyl, bicyclo[1.1.1]pentyl, bicyclo[2.2.1]heptyl or spiro [3.3]heptyl as an embodiment. The $C_{3-8}$ cycloalkyl represents a $C_{3-6}$ saturated cyclic hydrocarbon group as an embodiment; cyclopropyl, cyclobutyl, cyclopentyl or cyclohexyl, as an embodiment; and cyclopropyl further as an embodiment. The $C_{3-8}$ cycloalkyl represents cyclobutyl or cyclohexyl as another embodiment; cyclobutyl as another embodiment; cyclopentyl as another embodiment; and cyclohexyl as another embodiment.

The "4 to 8-membered saturated heterocyclyl" refers to a 4 to 8-membered saturated cyclic hydrocarbon group having one or more heteroatoms, particularly oxygen atoms, nitrogen atoms or sulfur atoms as atoms constituting a ring. The "4 to 8-membered saturated heterocyclyl" may have a crosslink and form a spiro ring. Examples of the "4 to 8-membered saturated heterocyclyl" include oxetanyl, azetidinyl, thietanyl, tetrahydrofuranyl, pyrrolidinyl, tetrahydrothiophenyl, tetrahydropyranyl, piperidinyl, tetrahydrothiopyranyl, oxepanyl, azepanyl, thiepanyl, oxocanyl, azocanyl, thiocanyl, dioxolanyl, imidazolidinyl, pyrazoridinyl, dithiolanyl, oxazolidinyl, isoxazolidinyl, thiazolidinyl, isothiazolidinyl, dioxanyl, piperazinyl, dithianyl, morpholinyl, thiomorpholinyl, oxathiolanyl, dioxepanyl, diazepanyl, dithiepanyl, oxazepanyl, thiazepanyl, oxathiepanyl, 3-oxadicyclo[3.1.0]hexyl, 2-oxaspiro[3.3]heptyl, 2-oxa-6-azaspiro[3.3]heptyl, 7-oxabicyclo[2.2.1]heptyl or 6-azaspiro

[2.5]octyl. The "4 to 8-membered saturated heterocyclyl" is oxetanyl, azetidinyl, tetrahydrofuranyl, pyrrolidinyl, tetrahydropyranyl, piperidinyl, tetrahydrothiopyranyl, azepanyl, morpholinyl, 3-oxabicyclo[3.1.0]hexyl or 6-azaspiro[2.5] octyl, as an embodiment. The "4 to 8-membered saturated heterocyclyl" is a 4 to 7-membered saturated heterocyclyl, as an embodiment. The "4 to 7-membered saturated heterocyclyl" is oxetanyl, azetidinyl, tetrahydrofuranyl, pyrrolidinyl, tetrahydropyranyl, piperidinyl, tetrahydrothiopyranyl, azepanyl, morpholinyl or 3-oxabicyclo[3.1.0]hexyl, as an embodiment; tetrahydrofuranyl, pyrrolidinyl, tetrahydropyranyl, piperidinyl or morpholinyl as an embodiment; and tetrahydrofuranyl or tetrahydropyranyl as an embodiment. The "4 to 7-membered saturated heterocyclyl" is pyrrolidinyl or piperidinyl as another embodiment; tetrahydropyranyl or piperidinyl as another embodiment; morpholinyl as another embodiment; and oxetanyl or azetidinyl as another embodiment.

The "aryl" refers to $C_{6-14}$ monocyclic to tricyclic aromatic hydrocarbon group and includes a cyclic group obtained by condensation with $C_{5-8}$ cycloalkene at a double bond site thereof. Examples of the "aryl" include phenyl, naphthyl, tetrahydronaphthyl, indenyl and fluorenyl. The "aryl" is phenyl as an embodiment.

The "heteroaryl" refers to a 5 to 6-membered aromatic ring group having 1 to 4 heteroatoms selected from oxygen, sulfur and nitrogen. Examples of the "heteroaryl" include pyrrolyl, furfuryl, thienyl, pyrazolyl, imidazolyl, isoxazolyl, oxazolyl, isothiazolyl, thiazolyl, triazolyl, oxadiazolyl, thiadiazolyl, tetrazolyl, pyridyl, pyrazinyl, pyrimidinyl, pyridazinyl and triazinyl. The "heteroaryl" is pyrazolyl, pyridazinyl or pyridyl as an embodiment; pyrazolyl or pyridyl as an embodiment; and pyrazolyl, as an embodiment.

The "halogen" refers to F, Cl, Br or I. The "halogen" is F or Cl as an embodiment; F as an embodiment; and Cl as another embodiment.

The "halogeno-$C_{1-6}$ alkyl" refers to a linear or branched $C_{1-6}$ alkyl group substituted with one or more halogens. The "halogeno-$C_{1-6}$ alkyl" is trifluoromethyl, trifluoroethyl, trifluoropropyl, 2-fluoro-2-methylpropyl, difluoromethyl, difluoroethyl, fluoromethyl or chloromethyl as an embodiment; trifluoromethyl or difluoromethyl, as an embodiment; trifluoromethyl as an embodiment; and difluoromethyl as another embodiment.

In the specification, the phrase "optionally substituted" refers to the case having no substituents or the case "having one or more substituents".

Substitution may be carried out at any site at which usually a hydrogen atom is present in a group.

Even if a combination is not specifically described, one or more embodiments may be combined with another embodiment.

In the specification, the "inflammatory disease" refers to a disease including autoinflammatory diseases including Cryopyrin-associated periodic syndrome (CAPS), gout and pseudo-gout; and non-alcoholic steatohepatitis (NASH), but the "inflammatory disease" is not limited to these. The "inflammatory disease" is an autoinflammatory disease in an embodiment, and CAPS as another embodiment. In this regard, "Cryopyrin-associated periodic syndrome (CAPS)" refers to a disease consisting of diseases of Familial cold autoinflammatory syndrome (FCAS), Muckle-Wells syndrome (MWS) and Neonatal-onset multisystem inflammatory disease/Chronic Infantile Neurological, Cutaneous, and Articular syndrome (NOMID/CINCA syndrome).

In the specification, the "neurodegenerative disease" refers to a disease group including α-synucleinopathy including Parkinson's disease, multiple system atrophy and Lewy body dementia; Alzheimer's disease; amyotrophic lateral sclerosis; and multiple sclerosis, but the "neurodegenerative disease" is not limited to these. The "neurodegenerative disease" is Alzheimer's disease, multiple sclerosis and amyotrophic lateral sclerosis as an embodiment; multiple sclerosis as an embodiment. The "neurodegenerative disease" is α-synucleinopathy as another embodiment; Parkinson's disease, as another embodiment; multiple system atrophy as another embodiment; and Lewy body dementias as another embodiment.

An embodiment of a compound of formula (I) or a salt thereof in the present invention will be described below.

(1-1) A compound of formula (I) or a salt thereof (n represents the number of $R^1$ substituents).

[Chem 10]

(I)

(1-2) The compound or a salt thereof, wherein the formula (I) is the following formula (Ia) (k is the number of $R^{1b}$ substituents).

[Chem 11]

(Ia)

(2-1) The compound or a salt thereof, wherein n is an integer of 1 to 4.

(2-2) The compound or a salt thereof, wherein n is an integer of 1 to 3.

(2-3) The compound or a salt thereof, wherein n is an integer of 1 or 2.

(2-4) The compound or a salt thereof, wherein n is 1.

(3-1) The compound or a salt thereof, wherein k is 0 or 1.

(3-2) The compound or a salt thereof, wherein k is 0.

(4-1) The compound or a salt thereof, wherein $R^1$ are the same or different from each other, and are $C_{1-6}$ alkyl, halogeno-$C_{1-6}$ alkyl, $C_{3-8}$ cycloalkyl, halogen, —O—$C_{1-6}$ alkyl, —O-halogeno-$C_{1-6}$ alkyl or cyano.

(4-2) The compound or a salt thereof, wherein $R^1$ in the formula (I) is $R^{1a}$ and $R^{1b}$ in the formula (Ia).

(5-1) The compound or a salt thereof, wherein $R^{1a}$ is $C_{1-6}$ alkyl, halogeno-$C_{1-6}$ alkyl, $C_{3-8}$ cycloalkyl, halogen, —O—$C_{1-6}$ alkyl, —O-halogeno-$C_{1-6}$ alkyl or cyano.

(5-2) The compound or a salt thereof, wherein $R^{1a}$ is $C_{1-6}$ alkyl, halogeno-$C_{1-6}$ alkyl, $C_{3-8}$ cycloalkyl, halogen, —O—$C_{1-6}$ alkyl or —O-halogeno-$C_{1-6}$ alkyl.

(5-3) The compound or a salt thereof, wherein $R^{1a}$ is halogeno-$C_{1-6}$ alkyl, $C_{3-8}$ cycloalkyl, halogen, —O—$C_{1-6}$ alkyl or —O-halogeno-$C_{1-6}$ alkyl.

(5-4) The compound or a salt thereof, wherein $R^{1a}$ is halogeno-$C_{1-6}$ alkyl, halogen, —O—$C_{1-6}$ alkyl or —O-halogeno-$C_{1-6}$ alkyl.

(5-5) The compound or a salt thereof, wherein $R^{1a}$ is halogeno-$C_{1-6}$ alkyl.

(5-6) The compound or a salt thereof, wherein $R^{1a}$ is halogen.

(5-7) The compound or a salt thereof, wherein $R^{1a}$ is —O—$C_{1-6}$ alkyl.

(5-8) The compound or a salt thereof, wherein $R^{1a}$ is —O-halogeno-$C_{1-6}$ alkyl.

(5-9) The compound or a salt thereof, wherein $R^{1a}$ is halogeno-$C_{1-6}$ alkyl, —O—$C_{1-6}$ alkyl or —O-halogeno-$C_{1-6}$ alkyl.

(6-1) The compound or a salt thereof, wherein $R^{1b}$ are the same or different from each other, and are $C_{1-6}$ alkyl, halogeno-$C_{1-6}$ alkyl or halogen.

(6-2) The compound or a salt thereof, wherein $R^{1b}$ is halogen.

(7-1) The compound or a salt thereof, wherein $R^2$ is $C_{1-6}$ alkyl, $C_{3-8}$ cycloalkyl, halogeno-$C_{1-6}$ alkyl, —O—$C_{1-6}$ alkyl, —N($C_{1-6}$ alkyl)$_2$ or aryl.

(7-2) The compound or a salt thereof, wherein $R^2$ is $C_{1-6}$ alkyl, $C_{3-8}$ cycloalkyl, halogeno-$C_{1-6}$ alkyl, —N($C_{1-6}$ alkyl)$_2$ or aryl.

(7-3) The compound or a salt thereof, wherein $R^2$ is $C_{1-6}$ alkyl or $C_{3-8}$ cycloalkyl.

(7-4) The compound or a salt thereof, wherein $R^2$ is $C_{1-6}$ alkyl.

(7-5) The compound or a salt thereof, wherein $R^2$ is $C_{3-8}$ cycloalkyl.

(8-1) The compound or a salt thereof, wherein $R^3$ is H or $C_{1-6}$ alkyl.

(8-2) The compound or a salt thereof, wherein $R^3$ is H.

(9-1) The compound or a salt thereof, wherein $R^4$ is $C_{1-6}$ alkyl substituted with the same or different one to four $R^3$; —$C_{1-6}$ alkylene-(aryl optionally substituted with the same or different one to four $R^6$); —$C_{1-6}$ alkylene-($C_{3-8}$ cycloalkyl optionally substituted with the same or different one to four $R^7$), —$C_{1-6}$ alkylene-(heteroaryl optionally substituted with the same or different one to four $R^8$); —$C_{1-6}$ alkylene-(4 to 7-membered saturated heterocyclyl optionally substituted with the same or different one to four $R^9$); $C_{3-8}$ cycloalkyl optionally substituted with the same or different one to four $R^{10}$; heteroaryl optionally substituted with the same or different one to four $R^{11}$; or 4 to 8-membered saturated heterocyclyl optionally substituted with the same or different one to four $R^{12}$.

(9-2) The compound or a salt thereof, wherein $R^4$ is $C_{1-6}$ alkyl substituted with the same or different one to four $R^5$; —$C_{1-6}$ alkylene-(aryl optionally substituted with the same or different one to four $R^6$); —$C_{1-6}$ alkylene-($C_{3-8}$ cycloalkyl optionally substituted with the same or different one to four $R^7$), —$C_{1-6}$alkylene-(heteroaryl optionally substituted with the same or different one to four $R^8$); —$C_{1-6}$ alkylene-(4 to 7-membered saturated heterocyclyl optionally substituted with the same or different one to four $R^9$); $C_{3-8}$ cycloalkyl optionally substituted with the same or different one to four $R^{10}$; heteroaryl optionally substituted with the same or different one to four $R^{11}$; or 4 to 7-membered saturated heterocyclyl optionally substituted with the same or different one to four $R^{12}$.

(9-3) The compound or a salt thereof, wherein $R^4$ is $C_{1-6}$ alkyl substituted with the same or different one to four $R^5$; —$C_{1-6}$ alkylene-(aryl optionally substituted with the same or different one to four $R^6$); —$C_{1-6}$ alkylene-($C_{3-8}$ cycloalkyl optionally substituted with the same or different one to four $R^7$); —$C_{1-6}$ alkylene-heteroaryl; —$C_{1-6}$ alkylene-(4 to 7-membered saturated heterocyclyl optionally substituted with the same or different one to four $R^9$); $C_{3-8}$ cycloalkyl optionally substituted with the same or different one to four $R^{10}$; heteroaryl; or 4 to 7-membered saturated heterocyclyl optionally substituted with the same or different one to four $R^{12}$.

(9-4) The compound or a salt thereof, wherein $R^4$ is —$C_{1-6}$ alkylene-($C_{3-8}$ cycloalkyl optionally substituted with the same or different one to four $R^7$), —$C_{1-6}$ alkylene-(4 to 7-membered saturated heterocyclyl optionally substituted with the same or different one to four $R^9$, $C_{3-8}$ cycloalkyl optionally substituted with the same or different one to four $R^{10}$, or 4 to 7-membered saturated heterocyclyl optionally substituted with the same or different one to four $R^{12}$.

(9-5) The compound or a salt thereof, wherein $R^4$ is $C_{3-8}$ cycloalkyl optionally substituted with the same or different one to four $R^{10}$, or 4 to 7-membered saturated heterocyclyl optionally substituted with the same or different one to four $R^{12}$.

(9-6) The compound or a salt thereof, wherein $R^4$ is $C_{1-6}$ alkyl substituted with the same or different 1 to 4 substituents $R^5$.

(9-7) The compound or a salt thereof, wherein $R^4$ is $C_{1-6}$ alkyl substituted with the same or different one to three $R^5$.

(9-8) The compound or a salt thereof, wherein $R^4$ is $C_{1-6}$ alkyl substituted with the same or different one or two $R^5$.

(9-9) The compound or a salt thereof, wherein $R^4$ is $C_{1-6}$ alkyl substituted with one $R^5$.

(9-10) The compound or a salt thereof, wherein $R^4$ is —$C_{1-6}$ alkylene-(aryl optionally substituted with the same or different one to four $R^6$).

(9-11) The compound or a salt thereof, wherein $R^4$ is —$C_{1-6}$ alkylene-(aryl optionally substituted with the same or different one to three $R^6$).

(9-12) The compound or a salt thereof, wherein $R^4$ is —$C_{1-6}$ alkylene-(aryl optionally substituted with the same or different one or two $R^6$).

(9-13) The compound or a salt thereof, wherein $R^4$ is —$C_{1-6}$ alkylene-(aryl optionally substituted with one $R^6$).

(9-14) The compound or a salt thereof, wherein $R^4$ is —$C_{1-6}$ alkylene-aryl.

(9-15) The compound or a salt thereof, wherein $R^4$ is —$C_{1-6}$ alkylene-($C_{3-8}$ cycloalkyl optionally substituted with the same or different one to four $R^7$).

(9-16) The compound or a salt thereof, wherein $R^4$ is —$C_{1-6}$ alkylene-($C_{3-8}$ cycloalkyl optionally substituted with the same or different one to three $R^7$).

(9-17) The compound or a salt thereof, wherein $R^4$ is —$C_{1-6}$ alkylene-($C_{3-8}$ cycloalkyl optionally substituted with the same or different one or two $R^7$).

(9-18) The compound or a salt thereof, wherein $R^4$ is —$C_{1-6}$ alkylene-($C_{3-8}$ cycloalkyl optionally substituted with one $R^7$).

(9-19) The compound or a salt thereof, wherein $R^4$ is —$C_{1-6}$ alkylene-$C_{3-8}$ cycloalkyl.

(9-20) The compound or a salt thereof, wherein $R^4$ is —$C_{1-6}$ alkylene-(heteroaryl optionally substituted with the same or different one to four $R^8$).

(9-21) The compound or a salt thereof, wherein $R^4$ is —$C_{1-6}$ alkylene-(heteroaryl optionally substituted with the same or different one to three $R^8$).

(9-22) The compound or a salt thereof, wherein $R^4$ is —$C_{1-6}$ alkylene-(heteroaryl optionally substituted with the same or different one or two $R^8$).

(9-23) The compound or a salt thereof, wherein $R^4$ is —$C_{1-6}$ alkylene-(heteroaryl optionally substituted with one $R^8$).

(9-24) The compound or a salt thereof, wherein $R^4$ is —$C_{1-6}$ alkylene-heteroaryl.

(9-25) The compound or a salt thereof, wherein $R^4$ is —$C_{1-6}$ alkylene-(4 to 7-membered saturated heterocyclyl optionally substituted with the same or different one to four $R^9$.

(9-26) The compound or a salt thereof, wherein $R^4$ is —$C_{1-6}$ alkylene-(4 to 7-membered saturated heterocyclyl optionally substituted with the same or different one to three $R^9$.

(9-27) The compound or a salt thereof, wherein $R^4$ is —$C_{1-6}$ alkylene-(4 to 7-membered saturated heterocyclyl optionally substituted with the same or different one or two $R^9$.

(9-28) The compound or a salt thereof, wherein $R^4$ is —$C_{1-6}$ alkylene-(4 to 7-membered saturated heterocyclyl optionally substituted with one $R^9$).

(9-29) The compound or a salt thereof, wherein $R^4$ is —$C_{1-6}$ alkylene-4 to 7-membered saturated heterocyclyl.

(9-30) The compound or a salt thereof, wherein $R^4$ is —$C_{3-8}$ cycloalkyl optionally substituted with the same or different one to four $R^{10}$.

(9-31) The compound or a salt thereof, wherein $R^4$ is $C_{3-8}$cycloalkyl optionally substituted with the same or different one to three $R^{10}$.

(9-32) The compound or a salt thereof, wherein $R^4$ is $C_{3-8}$ cycloalkyl optionally substituted with the same or different one or two $R^{10}$.

(9-33) The compound or a salt thereof, wherein $R^4$ is $C_{3-8}$ cycloalkyl optionally substituted with one $R^{10}$.

(9-34) The compound or a salt thereof, wherein $R^4$ is —$C_{3-8}$ cycloalkyl.

(9-35) The compound or a salt thereof, wherein $R^4$ is heteroaryl optionally substituted with the same or different one to four $R^{11}$.

(9-36) The compound or a salt thereof, wherein $R^4$ is heteroaryl optionally substituted with the same or different one to three $R^{11}$.

(9-37) The compound or a salt thereof, wherein $R^4$ is heteroaryl optionally substituted with the same or different one or two $R^{11}$.

(9-38) The compound or a salt thereof, wherein $R^4$ is heteroaryl optionally substituted with one $R^{11}$.

(9-39) The compound or a salt thereof, wherein $R^4$ is heteroaryl.

(9-40) The compound or a salt thereof, wherein $R^4$ is 4 to 7-membered saturated heterocyclyl optionally substituted with the same or different one to four $R^{12}$.

(9-41) The compound or a salt thereof, wherein $R^4$ is 4 to 7-membered saturated heterocyclyl optionally substituted with the same or different one to three $R^{12}$.

(9-42) The compound or a salt thereof, wherein $R^4$ is 4 to 7-membered saturated heterocyclyl optionally substituted with the same or different one or two $R^{12}$.

(9-43) The compound or a salt thereof, wherein $R^4$ is 4 to 7-membered saturated heterocyclyl optionally substituted with one $R^{12}$.

(9-44) The compound or a salt thereof, wherein $R^4$ is 4 to 7-membered saturated heterocyclyl.

(9-45) The compound or a salt thereof, wherein $R^4$ is —$C_{1-6}$ alkylene-(4 to 7-membered saturated heterocyclyl); $C_{3-8}$ cycloalkyl optionally substituted with the same or different one to two $R^{10}$; or 4 to 7-membered saturated heterocyclyl optionally substituted with one $R^{12}$.

(9-46) The compound or a salt thereof, wherein $R^4$ is $C_{3-8}$cycloalkyl optionally substituted with one $R^{10}$; or 4 to 7-membered saturated heterocyclyl optionally substituted with one $R^{12}$.

(9-47) The compound or a salt thereof, wherein $R^4$ is —$C_{1-6}$ alkylene-(4 to 7-membered saturated heterocyclyl optionally substituted with the same or different one to four $R^9$); $C_{3-8}$ cycloalkyl optionally substituted with the same or different one to four $R^{10}$; or 4 to 7-membered saturated heterocyclyl optionally substituted with the same or different one to four $R^{12}$.

(10-1) The compound or a salt thereof, wherein $R^5$ is —$OR^{13}$, —$NR^{14}R^{15}$, halogen or cyano.

(10-2) The compound or a salt thereof, wherein $R^5$ is —$OR^{13}$ or —$NR^{14}R^{15}$.

(10-3) The compound or a salt thereof, wherein $R^5$ is —$OR^{13}$.

(10-4) The compound or a salt thereof, wherein $R^5$ is —$NR^{14}R^{13}$.

(11-1) The compound or a salt thereof, wherein $R^6$ is $C_{1-6}$ alkyl, a halogeno-$C_{1-6}$ alkyl, $C_{3-8}$ cycloalkyl, —$OR^{13}$, —$NR^{14}R^{15}$, —$C_{1-6}$ alkylene-$OR^{13}$, —$C_{1-6}$ alkylene-$NR^{14}R^{15}$, halogen or cyano.

(11-2) The compound or a salt thereof, wherein $R^6$ is $C_{1-6}$alkyl, halogeno-$C_{1-6}$ alkyl, —$OR^{13}$, —$NR^{14}R^{15}$ or halogen.

(11-3) The compound or a salt thereof, wherein $R^6$ is —$OR^{13}$.

(12-1) The compound or a salt thereof, wherein $R^7$ is $C_{1-6}$ alkyl, halogeno-$C_{1-6}$ alkyl, $C_{3-8}$ cycloalkyl, —$OR^{13}$, —$NR^{14}R^{15}$, —$C_{1-6}$alkylene-$OR^{13}$, —$C_{1-6}$alkylene-$NR^{14}R^{15}$, halogen or cyano.

(12-2) The compound or a salt thereof, wherein $R^7$ is —$OR^{13}$, —$NR^{14}R^{15}$, —$C_{1-6}$ alkylene-$OR^{13}$ or —$C_{1-6}$ alkylene-$NR^{14}R^{15}$.

(12-3) The compound or a salt thereof, wherein $R^7$ is —$OR^{13}$ or —$NR^{14}R^{15}$.

(12-4) The compound or a salt thereof, wherein $R^7$ is —$OR^{13}$.

(12-5) The compound or a salt thereof, wherein $R^7$ is —$NR^{14}R^{15}$.

(12-6) The compound or a salt thereof, wherein R is —$C_{1-6}$ alkylene-$OR^{13}$ or —$C_{1-6}$ alkylene-$NR^{14}R^{15}$.

(12-7) The compound or a salt thereof, wherein $R^7$ is —$C_{1-6}$ alkylene-$OR^{13}$.

(12-8) The compound or a salt thereof, wherein $R^7$ is —$C_{1-6}$ alkylene-$NR^{14}R^{15}$.

(13-1) The compound or a salt thereof, wherein $R^8$ is $C_{1-6}$alkyl, halogeno-$C_{1-6}$ alkyl, $C_{3-8}$ cycloalkyl, —$OR^{13}$, —$NR^{14}R^{15}$, —$C_{1-6}$alkylene-$OR^{13}$, —$C_{1-6}$alkylene-$NR^{14}R^{15}$, halogen or cyano.

(13-2) The compound or a salt thereof, wherein $R^8$ is $C_{1-6}$alkyl, halogeno-$C_{1-6}$ alkyl, —$OR^{13}$, —$NR^{14}R^{15}$ or halogen.

(13-3) The compound or a salt thereof, wherein $R^8$ is —$OR^{13}$, —$NR^{14}R^{15}$ or halogen.

(14-1) The compound or a salt thereof, wherein $R^9$ is $C_{1-6}$alkyl, halogeno-$C_{1-6}$ alkyl, $C_{3-8}$ cycloalkyl, —$OR^{13}$, —$NR^{14}R^{15}$, —$C_{1-6}$alkylene-$OR^{13}$, —$C_{1-6}$alkylene-$NR^{14}R^{15}$, halogen, cyano, oxo, —$C(O)$—$C_{1-6}$ alkyl or —$S(O)_2$—$C_{1-6}$ alkyl.

(14-2) The compound or a salt thereof, wherein $R^9$ is $C_{1-6}$ alkyl, halogeno-$C_{1-6}$ alkyl, —$OR^{13}$, —$NR^{14}R^{15}$, halogen, oxo or —$C(O)$—$C_{1-6}$ alkyl.

(14-3) The compound or a salt thereof, wherein $R^9$ is —$OR^{13}$, —$NR^{14}R^{15}$, halogen or —$C(O)$—$C_{1-6}$ alkyl.

(14-4) The compound or a salt thereof, wherein $R^9$ is —$OR^{13}$ or —C(O)—$C_{1-6}$ alkyl.

(14-5) The compound or a salt thereof, wherein $R^9$ is —C(O)—$C_{1-6}$ alkyl.

(15-1) The compound or a salt thereof, wherein $R^{10}$ is $C_{1-6}$ alkyl, halogeno-$C_{1-6}$ alkyl, $C_{3-8}$ cycloalkyl, —$OR^{13}$, —$NR^{14}R^{15}$, —$C_{1-6}$ alkylene-$OR^{13}$, —$C_{1-6}$ alkylene-$NR^{14}R^{15}$, halogen, —C(O)—OH or cyano.

(15-2) The compound or a salt thereof, wherein $R^{10}$ is $C_{1-6}$ alkyl, halogeno-$C_{1-6}$ alkyl, $C_{3-8}$ cycloalkyl, —$OR^{13}$, —$NR^{14}R^{15}$, —$C_{1-6}$alkylene-$OR^{13}$, —$C_{1-6}$alkylene-$NR^{14}R^{15}$, halogen or cyano.

(15-3) The compound or a salt thereof, wherein $R^{10}$ is $C_{1-6}$ alkyl, —$OR^{13}$, —$NR^{14}R^{15}$, —$C_{1-6}$ alkylene-$OR^{13}$, —$C_{1-6}$ alkylene-$NR^{14}R^{15}$, halogen or cyano.

(15-4) The compound or a salt thereof, wherein $R^{10}$ is $C_{1-6}$ alkyl, —$OR^{13}$, —$NR^{14}R^{15}$, halogen or cyano.

(15-5) The compound or a salt thereof, wherein $R^{10}$ is $C_{1-6}$ alkyl, —$OR^{13}$ or —$NR^{14}R^{15}$.

(15-6) The compound or a salt thereof, wherein $R^{10}$ is $C_{1-6}$ alkyl or —$OR^{13}$.

(15-7) The compound or a salt thereof, wherein $R^{10}$ is —$OR^{13}$ or —$NR^{14}R^{15}$.

(15-8) The compound or a salt thereof, wherein $R^{10}$ is —$OR^{13}$.

(15-9) The compound or a salt thereof, wherein $R^{10}$ is —$NR^{14}R^{15}$.

(16-1) The compound or a salt thereof, wherein $R^{11}$ is $C_{1-6}$ alkyl, a halogeno-$C_{1-6}$ alkyl, $C_{3-8}$ cycloalkyl, —$OR^{13}$, —$NR^{14}R^{15}$, —$C_{1-6}$ alkylene-$OR^{13}$, —$C_{1-6}$ alkylene-$NR^{14}R^{15}$, halogen or cyano.

(16-2) The compound or a salt thereof, wherein $R^{11}$ is $C_{1-6}$alkyl, halogeno-$C_{1-6}$ alkyl, —$OR^{13}$, —$NR^{14}R^{15}$, —$C_{1-6}$ alkylene-$OR^{13}$, —$C_{1-6}$ alkylene-$NR^{14}R^{15}$ or halogen.

(16-3) The compound or a salt thereof, wherein $R^{11}$ is $C_{1-6}$ alkyl or —$C_{1-6}$ alkylene-$OR^{13}$.

(16-4) The compound or a salt thereof, wherein $R^{11}$ is $C_{1-6}$alkyl.

(16-5) The compound or a salt thereof, wherein $R^{11}$ is —$C_{1-6}$ alkylene-$OR^{14}$ thereof.

(17-1) The compound or a salt thereof, wherein $R^{12}$ is $C_{1-6}$ alkyl, halogeno-$C_{1-6}$ alkyl, $C_{3-8}$ cycloalkyl, 4 to 7-membered saturated heterocyclyl, —$OR^{13}$, —$NR^{14}R^{15}$, —$C_{1-6}$ alkylene-$C_{3-8}$ cycloalkyl, —$C_{1-6}$ alkylene-$OR^{13}$, —$C_{1-6}$ alkylene-$NR^{14}R^{15}$, —$C_{1-6}$alkylene-cyano, —$C_{1-6}$ alkylene-C(O)—OH, halogen, cyano, oxo, —C(O)—$NH_2$, —C(O)—$C_{1-6}$ alkyl or —$S(O)_2$—$C_{1-6}$ alkyl.

(17-2) The compound or a salt thereof, wherein $R^{12}$ is $C_{1-6}$alkyl, halogeno-$C_{1-6}$ alkyl, $C_{3-8}$ cycloalkyl, —$OR^{13}$, —$NR^{14}R^{15}$, —$C_{1-6}$ alkylene-$OR^{13}$, —$C_{1-6}$alkylene-$NR^{14}R^{15}$, halogen, cyano, oxo, —C(O)—$C_{1-6}$alkyl or —$S(O)_2$—$C_{1-6}$ alkyl.

(17-3) The compound or a salt thereof, wherein $R^{12}$ is $C_{1-6}$ alkyl, $C_{3-8}$ cycloalkyl, —$OR^{13}$, —$NR^{14}R^{15}$, —$C_{1-6}$alkylene-$OR^{13}$, —$C_{1-6}$alkylene-$NR^{14}R^{15}$, oxo, —C(O)—$C_{1-6}$ alkyl or —$S(O)_2$—$C_{1-6}$ alkyl.

(17-4) The compound or a salt thereof, wherein $R^{12}$ is $C_{1-6}$ alkyl, $C_{3-8}$ cycloalkyl, —$OR^{13}$, —$C_{1-6}$ alkylene-$OR^{13}$, oxo or —C(O)—$C_{1-6}$ alkyl.

(17-5) The compound or a salt thereof, wherein $R^{12}$ is $C_{1-6}$ alkyl, $C_{3-8}$ cycloalkyl, —$OR^{13}$ or oxo.

(17-6) The compound or a salt thereof, wherein $R^{12}$ is $C_{1-6}$ alkyl, —$OR^{13}$ or oxo.

(17-7) The compound or a salt thereof, wherein $R^{12}$ is $C_{1-6}$ alkyl or —$OR^{13}$.

(17-8) The compound or a salt thereof, wherein $R^{12}$ is —$OR^{13}$.

(17-9) The compound or a salt thereof, wherein $R^{12}$ is oxo.

(17-10) The compound or a salt thereof, wherein $R^{12}$ is $C_{3-8}$ cycloalkyl.

(17-11) The compound or a salt thereof, wherein $R^{12}$ is —C(O)—$C_{1-6}$ alkyl.

(17-12) The compound or a salt thereof, wherein $R^{12}$ is $C_{1-6}$ alkyl, $C_{3-8}$ cycloalkyl or —$OR^{13}$.

(17-13) The compound or a salt thereof, wherein $R^{12}$ is $C_{1-6}$ alkyl.

(18-1) The compound or a salt thereof, wherein $R^{13}$ is H or $C_{1-6}$ alkyl.

(18-2) The compound or a salt thereof, wherein $R^{13}$ is H.

(18-3) The compound or a salt thereof, wherein $R^{13}$ is $C_{1-6}$ alkyl.

(19-1) The compound or a salt thereof, wherein $R^{14}$ and $R^{15}$ are the same or different from each other, and are H, $C_{1-6}$ alkyl or —C(O)—$C_{1-6}$ alkyl.

(19-2) The compound or a salt thereof, wherein $R^{14}$ and $R^{15}$ are the same or different from each other, and are H or $C_{1-6}$ alkyl.

(19-3) The compound or a salt thereof, wherein $R^{14}$ and $R^{15}$ are H.

(19-4) The compound or a salt thereof, wherein $R^{14}$ is —C(O)—$C_{1-6}$ alkyl and $R^{15}$ is H.

(20) The compound or a salt thereof, having a combination of two or more embodiments of groups selected from those described in the above (1-1) to (19-4) and not mutually contradicted. Examples of the groups include, but are not particularly limited to, the following combinations.

(20-1) The compound or a salt thereof, having a combination of embodiments (1-1), (2-1), (4-1), (7-1), (8-1), (9-2), (10-1), (11-1), (12-1), (13-1), (14-1), (15-2), (16-1), (17-2), (18-1) and (19-1).

(20-2) The compound or a salt thereof, having a combination of embodiments (1-2), (3-1), (5-1), (6-1), (7-2), (8-2), (9-3), (10-1), (11-3), (12-2), (14-5), (15-3), (17-2), (18-1) and (19-1).

(20-3) The compound or a salt thereof, having a combination of embodiments (1-2), (3-2), (5-2), (6-1), (7-3), (8-2), (9-4), (12-2), (14-5), (15-3), (17-2), (18-1) and (19-1).

(20-4) The compound or a salt thereof, having a combination of embodiments (1-2), (3-2), (5-8), (7-4), (8-2), (9-33), (15-8), and (18-2).

(20-5) The compound or a salt thereof, having a combination of embodiments (1-2), (3-2), (5-6), (7-4), (8-2), (9-43), (17-8), and (18-2).

(20-6) The compound or a salt thereof, having a combination of embodiments (1-2), (3-2), (5-5), (7-5), (8-2), (9-32), (15-6), and (18-2).

(20-7) The compound or a salt thereof, having a combination of embodiments (1-2), (3-2), (5-7), (7-4), (8-2), (9-33), (15-8), and (18-2).

(20-8) The compound or a salt thereof, having a combination of embodiments (1-2), (3-2), (5-5), (7-4), (8-2), (9-43), and (17-10).

(20-9) The compound or a salt thereof, having a combination of embodiments (1-2), (3-2), (5-5), (7-4), (8-2), (9-33), (15-8), and (18-2).

(20-10) The compound or a salt thereof, having a combination of embodiments (1-2), (3-2), (5-5), (7-4), (8-2), (9-33), (15-9), and (19-3).

(20-11) The compound or a salt thereof, having a combination of embodiments (1-2), (3-2), (5-5), (7-4), (8-2), and (9-29).

(20-12) The compound or a salt thereof, having a combination of embodiments (1-2), (3-2), (5-5), (7-4), (8-2), (9-43) and (17-8).

(20-13) The compound or a salt thereof, having a combination of embodiments (1-2), (3-2), (5-8), (7-4), (8-2), (9-43) and (17-8).

(20-14) The compound or a salt thereof, having a combination of embodiments (1-2), (3-2), (5-4), (7-3), (8-2), (9-45), (15-5), (17-12), (18-2) and (19-3).

(20-15) The compound or a salt thereof, having a combination of embodiments (1-2), (3-2), (5-9), (7-4), (8-2), (9-46), (15-7), (17-13), (18-2) and (19-3).

(20-16) The compound or a salt thereof, in which the formula (I) is the formula (Ia), wherein $R^{1a}$ is trifluoromethyl, Cl, —O-methyl, —O-difluoromethyl, or —O-trifluoromethyl; $R^2$ is methyl, or cyclopropyl; $R^3$ is H; $R^4$ is -methylene-morpholinyl, cyclobutyl optionally substituted with the same or different one to two $R^{10}$ cyclohexyl optionally substituted with the same or different one to two $R^{10}$, tetrahydropyranyl optionally substituted with one substituent, $R^{12}$, or piperidinyl optionally substituted with one $R^{12}$; $R^{10}$ is methyl, —OH, or —NH$_2$; $R^{12}$ is methyl, cyclopropyl, or —OH; and k is 0.

Examples of compounds of the present invention include a compound or a salt thereof, wherein the compound is selected from the group of:

2-(3-{[(1R,2R)-2-hydroxycyclohexyl]amino}-5-methyl-1,2,4-triazin-6-yl)-5-(trifluoromethoxy)phenol, (3S,4R)-4-{[6-(4-chloro-2-hydroxyphenyl)-5-methyl-1,2,4-triazin-3-yl]amino}oxan-3-ol, 2-(5-cyclopropyl-3-{[(1s,3s)-3-hydroxy-3-methylcyclobutyl]amino}-1,2,4-triazin-6-yl)-5-(trifluoromethyl) phenol, 2-(3-{[(1R,2R)-2-hydroxycyclohexyl]amino}-5-methyl-1,2,4-triazin-6-yl)-5-methoxyphenol, 2-(3-{[(3R)-1-cyclopropylpiperidin-3-yl]amino}-5-methyl-1,2,4-triazin-6-yl)-5-(trifluoromethyl)phenol, 2-(3-{[(1R,3S)-3-hydroxycyclohexyl]amino}-5-methyl-1,2,4-triazin-6-yl)-5-(trifluoromethyl)phenol, 5-(difluoromethoxy)-2-(3-{[(1R,2R)-2-hydroxycyclohexyl]amino}-5-methyl-1,2,4-triazin-6-yl)phenol, 2-(3-{[(1R,2R)-2-aminocyclohexyl]amino}-5-methyl-1,2,4-triazin-6-yl)-5-(trifluoromethyl)phenol, 2-[5-methyl-3-({[(2R)-morpholin-2-yl]methyl)amino}-1,2,4-triazin-6-yl]-5-(trifluoromethyl)phenol, 2-(5-methyl-3-{[(3R)-1-methylpiperidin-3-yl]amino}-1,2,4-triazin-6-yl)-5-(trifluoromethyl)phenol, and 5-(difluoromethoxy)-2-(5-methyl-3-{[(3R)-1-methylpiperidin-3-yl]amino}-1,2,4-triazin-6-yl)phenol.

Also, one embodiment of compounds of the present invention include a compound or a salt thereof, which is selected from the group of:

2-(3-{[(1R,2R)-2-hydroxycyclohexyl]amino}-5-methyl-1,2,4-triazin-6-yl)-5-(trifluoromethoxy)phenol, (3S,4R)-4-{[6-(4-chloro-2-hydroxyphenyl)-5-methyl-1,2,4-triazin-3-yl]amino}oxan-3-ol, 2-(5-cyclopropyl-3-{[(1s,3s)-3-hydroxy-3-methylcyclobutyl]amino}-1,2,4-triazin-6-yl)-5-(trifluoromethyl) phenol, 2-(3-{[(1R,2R)-2-hydroxycyclohexyl]amino}-5-methyl-1,2,4-triazin-6-yl)-5-methoxyphenol, 2-(3-{[(3R)-1-cyclopropylpiperidin-3-yl]amino}-5-methyl-1,2,4-triazin-6-yl)-5-(trifluoromethyl)phenol, 2-(3-{[(1R,3S)-3-hydroxycyclohexyl]amino}-5-methyl-1,2,4-triazin-6-yl)-5-(trifluoromethyl)phenol, 5-(difluoromethoxy)-2-(3-{[(1R,2R)-2-hydroxycyclohexyl]amino}-5-methyl-1,2,4-triazin-6-yl)phenol, 2-(3-{[(1R,2R)-2-aminocyclohexyl]amino}-5-methyl-1,2,4-triazin-6-yl)-5-(trifluoromethyl)phenol, and 2-[5-methyl-3-({[(2R)-morpholin-2-yl]methyl}amino)-1,2,4-triazin-6-yl]-5-(trifluoromethyl)phenol.

Examples of compounds of the present invention include following compounds:

2-(3-{[(1R,2R)-2-hydroxycyclohexyl]amino}-5-methyl-1,2,4-triazin-6-yl)-5-methoxyphenol monohydrochloride, 2-(3-{[(1R,3S)-3-hydroxycyclohexyl]amino}-5-methyl-1,2,4-triazin-6-yl)-5-(trifluoromethyl)phenol monohydrochloride, 5-(difluoromethoxy)-2-(3-{[(1R,2R)-2-hydroxycyclohexyl]amino}-5-methyl-1,2,4-triazin-6-yl)phenol monohydrochloride, 2-(5-methyl-3-{[(3R)-1-methylpiperidin-3-yl]amino}-1,2,4-triazin-6-yl)-5-(trifluoromethyl)phenol dihydrochloride, and 2-(3-{[(1R,2R)-2-aminocyclohexyl]amino}-5-methyl-1,2,4-triazin-6-yl)-5-(trifluoromethyl)phenol dihydrochloride.

In the compounds represented by formula (I), tautomers and geometric isomers may exist depending on the types of substituents. In the specification, only a single type of isomer may sometimes be shown as the form of a compound of formula (I) or a salt thereof. Other isomers are also included in the present invention, and isomers isolated or a mixture thereof are also included herein.

A compound of formula (I) or a salt thereof may sometimes have an asymmetric center or an axial chirality, and correspondingly, enantiomers (optical isomers) thereof may exist. (R) form and (S) form enantiomers individually isolated and a mixture (including a racemic mixture or non-racemic mixture) of enantiomers are all included in the compound of formula (I) or a salt thereof. In an embodiment, an enantiomer is "stereochemically pure". The phrase "stereochemically pure" refers to the degree of purity, which is recognized as substantially stereochemically pure by that those skilled in the art. As another embodiment, an enantiomer is defined as a compound having a stereochemical purity of, for example, 90% ee (enantiomeric excess) or more, 95% ee or more, 98% ee or more or 99% ee or more.

The present invention further includes a pharmaceutically acceptable prodrug of a compound represented by formula (I). The pharmaceutically acceptable prodrug refers to a compound having a group, which can be converted into, e.g., an amino group, a hydroxy group or a carboxyl group, by decomposition with a solvent or in physiological conditions. Examples of a group responsible for formation of a prodrug are described, for example, in Prog. Med., 5, 2157-2161 (1985) and "Development of pharmaceuticals" (Hirokawa Shoten, 1990), Vol. 7, molecular design 163-198.

The salt of a compound of formula (I) is a pharmaceutically acceptable salt of a compound of formula (I). An acid addition salt or a salt with a base may be formed depending on the type of a substituent. Specific examples of the salt include acid addition salts including salts of inorganic acids such as hydrochloric acid, hydrogen bromide, hydrogen iodide acid, sulfuric acid, nitric acid, and phosphoric acid, and organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methanesulfonic acid, ethane sulfonic acid, benzenesulfonic acid, p-toluenesulfonic acid, aspartic acid, glutamic acid; salts of inorganic bases such as sodium, potassium, magnesium, calcium and aluminum; salts with organic bases such as methylamine, ethylamine, ethanolamine, ricin and ornithine; salts of amino acids and amino acid derivatives such as acetyl leucine; and ammonium salts.

The present invention includes hydrates, solvates and crystal polymorphism forms of a compound of formula (I) or a salt thereof.

The present invention includes a compound of formula (I) or a salt thereof labeled with one or more pharmaceutically acceptable radioactive or non-radioactive isotopes, as a whole. Examples of isotopes to be suitably used as an isotope label to the compound of the present invention include isotopes of hydrogen (e.g., $^2H$ and $^3H$), carbon (e.g., $^{11}C$, $^{13}C$ and $^{14}C$), nitrogen (e.g., $^{13}N$ and $^{15}N$), oxygen (e.g., $^{15}O$, $^{17}O$ and $^{18}O$), fluorine (e.g., $^{18}F$), chlorine (e.g., $^{36}Cl$), iodine (e.g., $^{123}I$ and $^{125}I$), phosphor (e.g., $^{32}P$) and sulfur (e.g., $^{35}S$). The compound of the invention of the present application labeled with an isotope can be used in studies such as tissue distribution study of a drug and/or a substrate. For example, a radioisotope such as tritium ($^3H$) and carbon 14 ($^{14}C$), since it is easily labeled and simply detected, can be used for the purpose of labelling and detection. In the case where an isotope is switched to a heavier isotope, for example, from a hydrogen atom to a deuterium ($^2H$) atom, metabolic stability is improved. Such a case may be therapeutically advantageous (for example, an increase of in vivo half-life, a reduction of dosage requirement, reduction of drug interaction). Positron emission isotopes (e.g., $^{11}C$, $^{18}F$, $^{15}O$ and $^{13}N$) can be used in positron emission tomography (PET) for examining a substrate receptor occupancy. The compound labeled with an isotope of the present invention can be produced by a method commonly known to those skilled in the art or in the same process as described in Examples or Production Examples except that an appropriate reagent labeled with an isotope is used in place of a reagent not labeled.

(Production Process)

A compound of formula (I) or a salt thereof can be produced by taking advantage of the fundamental structure or properties based on the types of substituents and using various synthesis methods known in the art thereto. At this time, depending on the type of functional group, replacing the functional group with an appropriate protective group (a group easily converted into the functional group) in the stage starting from a raw material to an intermediate is sometimes effective in view of manufacturing technique. Examples of the protective group are described, for example, in "Greene's Protective Groups in Organic Synthesis (4th edition, 2006) written by "Wuts (P. G. M. Wuts) and Greene (T. W. Greene). The protective group to be used may be appropriately selected depending on the reaction conditions. In this method, a reaction is carried out by introducing the protective group and thereafter, the protective group is removed, as needed. In this manner, a desired compound can be obtained.

A prodrug of a compound of formula (I) can be produced by introducing a predetermined group in the same manner as in the protective group in the stage starting from a raw material to an intermediate or subjecting the compound of formula (I) obtained further to a reaction. The reaction can be carried out by applying methods ordinarily known to those skilled in the art, such as esterification, amidation and dehydration.

Now, typical production processes for a compound of formula (I) will be described. Each of the processes can be carried out with reference to the literatures attached hereto. Note that the production process of the present invention is not limited to the following examples.

In the specification, the following brevity codes will be sometimes used.

CN: cyano, DMF: N,N-dimethylformamide, DMSO: dimethylsulfoxide, DIPEA: N,N-diisopropylethylamine, mCPBA: m-chloroperbenzoic acid, NBS: N-bromosuccinimide, NCS: N-chlorosuccinimide, NIS: N-iodosuccinimide, NMP: 1-methylpyrrolidin-2-one, Me: methyl, Oxone (registered trademark): potassium peroxymonosulfate, $PdCl_2(PPh_3)_2$: bis(triphenylphosphine)palladium (II) dichloride, $PdCl_2(dppf)$: [1,1'-bis(diphenylphosphino)ferrocene]palladium (II) dichloride, $PdCl_2(dppf)\cdot CH_2Cl_2$: [1,1'-bis(diphenylphosphino)ferrocene]palladium (II) dichloride/dichloromethane adduct, $Pd_2(dba)_3$: (1E,4E)-1,5-diphenylpenta-1,4-dien-3-one/palladium (3:2), $Pd(PPh_3)_4$: tetrakis(triphenylphosphine)palladium, SPhos Pd G3: (2-dicyclohexylphosphino-2',6'-dimethoxybiphenyl) [2-(2'-amino-1,1'-biphenyl)]palladium (II) methanesulfonic acid, RuPhos Pd G3: (2-dicyclohexylphosphino-2',6'-diisopropoxy-1,1'-biphenyl)[2-(2'-amino-1,1'-biphenyl)]palladium (II) methanesulfonic acid, THF: tetrahydrofuran, TFA: trifluoroacetic acid.

(First Process)

[Chem 12]

(wherein $X^1$ and $X^2$ are the same or different, and are Cl, Br or I. $R^a$ and $R^b$ are both H, or $R^a$ and $R^b$ are united with boronic acid residue to which said $R^a$ and $R^b$ are attached to form 4,4,5,5-tetramethyl-1,3,2-dioxaborolane. The same applied to the followings.)

(First Step)

This step is a step of obtaining a compound of formula (IV) by reacting a compound of formula (II) and a compound of formula (III). In the reaction, a compound of formula (II) and a compound of formula (III) are used in equal amounts or either one of the compounds is used in an excessive amount. The mixture of these are stirred in an inert solvent to a reaction or in the absence of a solvent, under cooling to heat reflux, preferably at room temperature to 190° C., usually for 0.1 hours to 5 days. Examples of the solvent used herein include, but are not particularly limited to, ethers such as diethyl ether, THF, 1,4-dioxane and 1,2-dimethoxyethane; alcohols such as methanol, ethanol, 1-propanol, 2-propanol and 1-butanol; water, pyridine, acetonitrile, NMP, DMF, DMSO; and mixtures thereof. It may be advantageous to carry out the reaction in the presence of an organic base such as triethylamine and DIPEA, or an inorganic base such as potassium carbonate, sodium carbonate, cesium carbonate and sodium hydride, in order to smoothly facilitate the reaction. The reaction may be carried out while applying microwave.

(Second Step)

This step is a step of obtaining a compound of formula (I) by reacting a compound of formula (IV) and a compound of formula (V).

In this reaction, the compound of formula (IV) and the compound of formula (V) are used in equal amounts or either one of the compounds is used in an excessive amount. The mixture of these are stirred in an inert solvent to a reaction in the presence of a catalyst and a base, under cooling to heat reflux, preferably at room temperature to 150° C., usually for 0.1 hours to 5 days. Examples of the solvent used herein include, but are not particularly limited to, Pd(PPh$_3$)$_4$, PdCl$_2$(PPh$_3$)$_2$, PdCl$_2$(dppf), PdCl$_2$(dppf)·CH$_2$Cl$_2$, Pd$_2$(dba)$_3$ and RuPhos Pd G3. Examples of the base include, but are not particularly limited to, tripotassium phosphate, sodium carbonate, potassium carbonate, cesium carbonate, sodium hydroxide, and sodium-t-butoxide. Examples of the solvent include, but are not particularly limited to, ethers such as diethyl ether, THF, 1,4-dioxane and 1,2-dimethoxyethane; aromatic hydrocarbons such as benzene, toluene and xylene; water, pyridine, acetonitrile, NMP, DMF, DMSO, and mixtures thereof. The reaction may be carried out while applying microwave.

LITERATURE

Journal of the American Chemical Society, 127, pp 4685-4696 (2005)

(Second Process)

[Chem 13]

(VI)

(VII)

(VIII)

-continued (IV)

(I)

(wherein Rc represents C$_{1-6}$ alkyl and m represents 1 or 2. The same applies to the followings.)

(First Step)

This step is a step of obtaining a compound of formula (VII) by reacting a compound of formula (VI) and an oxidizing agent. In the reaction, a compound of formula (VI) and an oxidizing agent are used in equal amounts or either one of them is used in an excessive amount. The mixture are stirred in an inert solvent to a reaction under cooling to room temperature conditions, preferably at −78° C. to room temperature, usually for 0.1 hours to 5 days. Examples of the oxidizing agent used herein include, but are not particularly limited to, mCPBA, hydrogen peroxide, Oxone (registered trademark). Examples of the solvent include, but are not particularly limited to, halogenated solvents such as dichloromethane, chloroform, carbon tetrachloride; ethers such as diethyl ether, THF, 1,4-dioxane and 1,2-dimethoxyethane; aromatic hydrocarbons such as benzene, toluene, xylene and mixtures thereof.

(Second Step)

The step is a step of obtaining a compound of formula (VIII) by reacting a compound of formula (VII) and a compound of formula (III).

In the reaction, a compound of formula (VII) and a compound of formula (III) are used in equal amounts or either one of the compounds is used in an excessive amount. The mixture of these is stirred in an inert solvent to a reaction or in the absence of a solvent under cooling to heat reflux, preferably at 0 to 190° C., usually for 0.1 hours to 5 days. Examples of the solvent used herein include, but are not particularly limited to, ethers such as diethyl ether, THF, 1,4-dioxane and 1,2-dimethoxyethane; alcohols such as methanol, ethanol, 1-propanol, 2-propanol and 1-butanol; water, pyridine, acetonitrile, NMP, DMF, DMSO, dichloromethane and mixtures thereof. It may be advantageous to carry out the reaction in the presence of an organic base such as triethylamine and DIPEA, or an inorganic base such as potassium carbonate, sodium carbonate, cesium carbonate and sodium hydride, in order to smoothly facilitate the reaction. The reaction may be carried out while applying microwave. Note that, the compound of formula (VIII) can be sometimes obtained also by adding the compound of formula (III) directly to the reaction mixture of the first step.

(Third Step)

This step is a step of obtaining a compound of formula (IV) by reacting a compound of formula (VIII) and a halogenating agent. In the reaction, a compound of formula (VIII) and a halogenating agent are used in equal amounts or either one of them is used in an excessive amount. The mixture of these is stirred in an inert solvent to a reaction or in the absence of a solvent, under cooling to heat reflux, preferably at −78 to 50° C., usually for 0.1 hours to 5 days. Examples of the halogenating agent to be used here include, but are not particularly limited to, NCS, NBS, NIS, bromine, iodine, dibromoisocyanuric acid, tetra-n-butylammonium tribromide and pyridinium tribromide. Examples of solvents include, but are not particularly limited to, ethers such as diethyl ether, THF, 1,4-dioxane and 1,2-dimethoxyethane; alcohols such as methanol, ethanol, 1-propanol, 2-propanol and 1-butanol; water, pyridine, acetonitrile, NMP, DMF, DMSO and mixtures thereof (Fourth Step)

The step is a step of obtaining a compound of formula (T) by reacting a compound of formula (IV) and a compound of formula (V) as in the second step of the first process.

(Other Processes)

Another compound of formula (I) can be obtained by subjecting the compound of formula (I) obtained by the above process used as a raw material to chemical modification reactions ordinarily employed by those skilled in the art, such as alkylation, esterification, amidation, sulfonylation, and deprotection reactions.

A compounds of formula (I) is isolated and purified as a free compound, a salt, hydrate and solvate thereof, or a crystalline polymorph.

A salt of a compound of formula (I) can also be produced by subjecting the compound to a reaction for forming a salt routinely employed.

Isolation and purification can be carried out using conventional chemical operations such as extraction, fractional crystallization, and various types of fractional chromatographic methods. Various isomers can be produced by selecting appropriate raw-material compounds or separated by using the difference in physicochemical properties between the isomers.

For example, an optical isomer can be obtained by general optical resolution of a racemate (e.g., fractional crystallization leading to a diastereomeric salt with an optically active base or an acid, chromatography using, e.g., chiral column) or can be produced from a suitable optically active raw material compound.

The pharmacological activities of a compound of formula (I) were confirmed by the following tests. Also, the pharmacological activities can be confirmed by modified tests known in the technical field.

Test Example 1

THP-1 IL-1β Production Inhibitory Test

To THP-1 cells, 50 ng/mL PMA (phorbol myristate acetate, SIGMA, P1585) was added at 37° C. and then the cells were cultured for 2 days. The culture medium was exchanged with serum-free RPMI-1640 medium, and a compound known in concentration was added. The cells were cultured at 37° C. for 15 minutes. LPS (lipopolysaccharide, SIMGA, L2880) and ATP (adenosine triphosphate, SIGMA, A2383) were added such that the final concentrations of them became 50 ng/mL and 5 mM, respectively. The cells were cultured at 37° C. for 2 hours. The supernatant was collected and the concentration of IL-1β was measured by ELISA (DuoSet ELISA human IL-1β, R&D Systems, DY201). The concentration of IL-1β was plotted against the logarithm of the concentration of the test compound, and the $IC_{50}$ value was calculated by sigmoidal Emax model non-linear regression analysis. The results are shown in Table 1-1 and Table 1-2. It was confirmed that compounds of Examples suppress IL-1β production.

TABLE 1-1

| Ex | $IC_{50}$ (nM) |
|---|---|
| 1 | 7.6 |
| 2 | 32 |
| 3 | 69 |
| 4 | 35 |
| 5 | 21 |
| 6 | 26 |
| 7 | 28 |
| 8 | 6.9 |
| 9 | 59 |
| 10 | 40 |
| 11 | 15 |
| 12 | 53 |
| 13 | 260 |
| 14 | 62 |
| 15 | 100 |
| 16 | 88 |
| 17 | 66 |
| 18 | 88 |
| 19 | 7.4 |
| 20 | 34 |
| 21 | 290 |
| 22 | 13 |
| 23 | 23 |
| 24 | 40 |
| 25 | 77 |
| 26 | 62 |
| 27 | 10 |
| 28 | 630 |
| 29 | 84 |
| 30 | 18 |
| 31 | 25 |
| 32 | 10 |
| 33 | 150 |
| 34 | 49 |
| 35 | 50 |
| 36 | 17 |
| 37 | 11 |
| 38 | 11 |
| 39 | 19 |
| 40 | 22 |
| 41 | 310 |
| 42 | 28 |
| 43 | 19 |
| 44 | 7.0 |
| 45 | 24 |
| 46 | 30 |
| 47 | 8.8 |
| 48 | 34 |
| 49 | 14 |
| 50 | 31 |
| 51 | 33 |
| 52 | 21 |
| 53 | 63 |
| 54 | 7.3 |
| 55 | 11 |
| 56 | 12 |
| 57 | 0.50 |
| 58 | 9.3 |
| 59 | 14 |
| 60 | 38 |
| 61 | 36 |
| 62 | 28 |
| 63 | 200 |
| 64 | 62 |
| 65 | 110 |
| 66 | 150 |
| 67 | 9.6 |
| 68 | 57 |
| 69 | 30 |
| 70 | 10 |
| 71 | 8.2 |
| 72 | 8.3 |

TABLE 1-1-continued

| Ex | IC$_{50}$ (nM) |
|---|---|
| 73 | 1.3 |
| 74 | 620 |
| 75 | 6.5 |
| 76 | 16 |
| 77 | 67 |
| 78 | 27 |
| 79 | 14 |
| 80 | 12 |
| 81 | 42 |
| 82 | 30 |
| 83 | 32 |
| 84 | 38 |
| 85 | 57 |
| 86 | 12 |
| 87 | 130 |
| 88 | 180 |
| 89 | 230 |
| 90 | 53 |
| 91 | 52 |
| 92 | 200 |
| 93 | 130 |
| 94 | 70 |
| 95 | 410 |
| 96 | 81 |
| 97 | 150 |
| 98 | 280 |
| 99 | 9.4 |
| 100 | 6.4 |
| 101 | 130 |
| 102 | 11 |
| 103 | 30 |
| 104 | 91 |
| 105 | 36 |
| 106 | 26 |
| 107 | 25 |
| 108 | 21 |
| 109 | 17 |
| 110 | 15 |
| 111 | 12 |
| 112 | 18 |
| 113 | 37 |
| 114 | 33 |
| 115 | 8.5 |
| 116 | 23 |
| 117 | 19 |
| 118 | 47 |
| 119 | 42 |
| 120 | 83 |
| 121 | 43 |
| 122 | 15 |
| 123 | 54 |
| 124 | 37 |
| 125 | 33 |
| 126 | 20 |
| 127 | 10 |
| 128 | 7.9 |
| 129 | 55 |
| 130 | 260 |
| 131 | 9.5 |
| 132 | 15 |
| 133 | 95 |
| 134 | 38 |
| 135 | 450 |
| 136 | 61 |
| 137 | 1500 |
| 138 | 5.6 |
| 139 | 690 |
| 140 | 160 |
| 141 | 470 |
| 142 | 340 |
| 143 | 220 |
| 144 | 160 |
| 145 | 39 |
| 146 | 12 |
| 147 | 28 |
| 148 | 150 |
| 149 | 23 |
| 150 | 6.8 |

TABLE 1-1-continued

| Ex | IC$_{50}$ (nM) |
|---|---|
| 151 | 35 |
| 152 | 22 |
| 153 | 7.8 |
| 154 | 31 |
| 155 | 370 |
| 156 | 23 |
| 157 | 5.7 |
| 158 | 850 |
| 159 | 120 |
| 160 | 210 |
| 161 | 70 |
| 162 | 350 |
| 163 | 640 |

TABLE 1-2

| Ex | IC$_{50}$ (nM) |
|---|---|
| 164 | 1.5 |
| 165 | 6.7 |
| 166 | 23 |
| 167 | 580 |
| 168 | 26 |
| 169 | 38 |
| 170 | 390 |
| 171 | 240 |
| 172 | 35 |
| 173 | 58 |
| 174 | 1.1 |
| 175 | 24 |
| 176 | 43 |
| 177 | 48 |
| 178 | 4.2 |
| 179 | 19 |
| 180 | 180 |
| 181 | 12 |
| 182 | 67 |
| 183 | 150 |
| 184 | 5.8 |
| 185 | 5.2 |
| 186 | 11 |
| 187 | 1.3 |
| 188 | 21 |

Test Example 2

TNF-α Production Inhibitory Test

To THP-1 cells, 50 ng/mL PMA (phorbol myristate acetate, SIGMA, P1585) was added and then the cells were cultured at 37° C. for 2 days. The culture medium was exchanged with serum-free RPMI-1640 medium, and a compound known in concentration was added. The cells were cultured at 37° C. for 15 minutes. LPS (lipopolysaccharide, SIMGA, L2880) was added such that the final concentrations of them became 50 ng/mL. The cells were cultured at 37° C. for 2 hours. The supernatant was collected and the concentration of TNF-α was measured by ELISA (DuoSet ELISA human TNF-α, R&D Systems, DY201). The concentration of TNF-α was plotted against the logarithm of the concentration of the test compound, and the IC$_{50}$ value was calculated by sigmoidal Emax model nonlinear regression analysis.

It was confirmed in this study that the compounds of Examples 27, 31, 59, 73, 75, 108, 131, 132, 141, 164 and 174, which are the compounds of formula (I), showed IC$_{50}$ values of 10 μM or higher.

Test Example 3

Rat Central Nervous System IL-1β Production Test

Male Wistar rats of 10-14 weeks old were administered with 12.5 μg/5 μL LPS (SIGMA, L2880) in the cisterna magna under isoflurane anesthesia. Two hours later, a test compound was orally administered. Further one hour later, 50 μg/5 μL BzATP (2'(3')—O-(4-benzoylbenzoyl)adenosine 5'-triphosphate triethylammonium salt, SIGMA, B6396) was administered in the cisterna magna. Thirty minutes later, the cerebrospinal fluid was collected. The cerebrospinal fluid was subjected to Western blotting using an anti-IL-1β antibody (Millipore, AB1832P) to measure IL-1β p17, and then, the suppression rate thereof relative to the solvent-administered group was calculated.

Table 2 shows the suppression rate of IL-1β p17 relative to the solvent-administered group, for the compounds of Examples 59, 75, 131, 132 and 164, which are the compounds of formula (I). In the Table, Dose refers to a dosage amount of each test compound, and Ex59, Ex75, Ex131, Ex132 and Ex164 represent Example 59, Example 75, Example 131, Example 132 and Example 164, respectively. It was confirmed that the compounds have inhibitory effects on IL-1β production.

TABLE 2

| Dose | Ex59 | Ex75 | Ex131 | Ex132 | Ex164 |
|---|---|---|---|---|---|
| 0.3 mg/kg | 45% | 12% | −33% | −3.7% | 67% |
| 1 mg/kg | 54% | 73% | −54% | 88% | 81% |
| 3 mg/kg | 85% | 100% | 61% | 88% | 80% |

Test Example 4

Motor Function Evaluation in Mouse α-Synuclein Fiber-Induced Neuroinflammation Model To male C57BL/6J mice, 8 μg of mouse α-synuclein fibrotic protein (StressMarq Biosciences Inc., SPR-324) was administered at the left striatum. Thirteen to fourteen weeks later, a test compound suspended in a 0.5% methyl cellulose solution was orally administered once per day. To a negative control group, a 0.5% methyl cellulose solution is administered. Four weeks later after initiation of administration, motor function was evaluated by the hanging wire test. A mouse was allowed to catch a wire horizontally stretched. When the mouse falls, the mouse was allowed to catch the wire again. This operation was continued for 3 minutes, and the number of falls was recorded. In this study, it was confirmed that a specific compound of formula (I) or a salt thereof has improvement effects on movement disorder.

Test Example 5

Mouse Ex Vivo IL-1β Production Test

Male C57BL/6J mice are orally administered with the compound suspended in 0.5% methylcellulose at an arbitrary dose at single or multiple times, and blood is collected after certain periods of time. LPS is added to the blood to a final concentration of 50 ng/mL, which is cultured at 37° C. for 3 hours. Then, ATP is added to a final concentration of 5 mM, which is cultured at 37° C. for 30 minutes. After removing blood cells by centrifugation, the concentration of IL-1β is measured by the ELISA method (DuoSet ELISA mouse IL-1β, R & D Systems, DY401).

Test Example 6

In Vitro Phototoxicity Test

The evaluation of in vitro phototoxicity tests was based on ICH S10: Guidelines for Evaluation of Phototoxicity of Drugs (Notification No. 0521-1) and OECD guideline for testing of chemicals 432: In vitro 3T3 NRU phototoxicity test, 2004, which was described in the OECD report. In this test, it was confirmed that the compounds of Examples 59, 75, 131, 132 and 164 had no phototoxic effect.

Test Example 7

Safety Pharmacological Test

As a safety pharmacological test, the human Ether-a-go-go Related Gene (hereinafter referred to as hERG) channel inhibitory effect was evaluated. The hERG channel inhibitory effect was evaluated using a modified method described in Combinatorial Chemistry & High Throughput Screening, 12, 1, 78-95 (2009). In this study, the compound of Examples 59, 75, 131, 132 and 164 showed $IC_{50}$ values of 10 μM or higher.

From the above results, it is expected that the compound of formula (I) or a salt thereof can be used for the preventing and/or treating e.g., an inflammatory disease and a neurodegenerative disease, as highly safe pharmaceuticals.

In the Test Example 1, it was confirmed that the compounds listed in Table 1, which are the compounds of formula (I) or a salt thereof, suppress IL-1β production. In the Test Example 3, it was confirmed that the compounds of Examples 59, 75, 131, 132 and 164 have inhibitory effects on IL-1β production in central nervous system. In the Test Example 4 of mouse α-synuclein fiber-induced neuroinflammation model, it was confirmed that a specific compound of formula (I) or a salt thereof improves motor function. From the above results, it is strongly expected that the compounds of formula (I) or a salt thereof can be used for the preventing and/or treating a neurodegenerative disease, particularly α-synucleinopathy including Parkinson's disease, multiple system atrophy and Lewy body dementia.

In addition, it is demonstrated from the results of Test Examples 6 and 7, that the compounds of the Examples 59, 75, 131, 132 and 164 do not show a phototoxic effect and hERG channel inhibitory effect of these compounds is weak. From the above results, it is strongly expected that the compounds of the Examples 59, 75, 131, 132 and 164 can be highly safe pharmaceuticals.

A pharmaceutical composition comprising one or more of compounds of formula (I) or salts thereof as an active ingredient can be prepared by using an excipient commonly used in the art, more specifically, e.g., a pharmaceutical excipient, a pharmaceutical carrier, in accordance with a method routinely employed.

Dosage form may be either oral administration using tablets, pills, capsules, granules, powders and liquids or parenteral administration using e.g., injection such as intra-articular, intravenous and intramuscular injections, suppositories, eye drops, eye ointments, transdermal liquids, ointments, transdermal patches, transmucosal fluids, transmucosal patches and inhalants.

As a solid composition for oral administration, e.g., tablets, powders and granules, are used. In such solid compositions, one or more active ingredients are blended with at least one inert excipient. Inert additives such as a lubricant, a disintegrant, a stabilizer and a dissolution aid may be incorporated in the composition in accordance with a method routinely used. Tablets, powders, granules or pills may be coated with wax, sugar film or a film of gastric soluble or enteric soluble material, as needed.

A liquid composition for oral administration contains a pharmaceutically acceptable opalizer, solution, suspension, syrup or elixir and an inert diluent ordinarily used such as purified water or ethanol. The liquid composition may contain, other than an inert diluent, an auxiliary agent such as a solubilizer, a wetting agent and a suspension, a sweetener, a flavoring agent, an aromatic agent and a preservative.

An injection for parenteral administration contains an aseptic aqueous or non-aqueous solvent, a suspension or an emulsifying agent. Examples of the aqueous solvent include distilled water for injection and saline. Examples of the non-aqueous solvent include an alcohol such as ethanol. The injections may further contain a tonicity agent, a preservative, a wetting agent, an emulsifier, a dispersant, a stabilizer or a dissolution aid. The injections can be sterilized, for example, by filtration through a bacteria-retaining filter, blending a disinfectant or irradiation. These can be also used by preparing an aseptic solid composition and dissolving or suspending the solid composition in aseptic water or an aseptic solvent for injection before use.

Example of the external preparation include ointments, plasters, creams, jellies, patches, sprays, lotions, eye drops and eye ointments. External preparations contain an ointment base, a lotion base, an aqueous or non-aqueous liquid, a suspension and an emulsion that are generally used.

As transmucosal agents such as inhalants and nasal agents, liquid or semi-solid agents are used and prepared in accordance with methods conventionally known. For example, excipients known in the technical field may be added and further pH adjusters, preservatives, surfactants, lubricants, stabilizers and thickeners may be appropriately added. For administration, an appropriate device for inhalation or insufflation can be used. For example, a device or atomizer known in the technical field such as a metered dose inhalation device may be used. The compound can be administered alone or in the form a powder mixture previously prepared or in combination with a pharmaceutically acceptable carrier in the form of a solution or suspension by use of such a device. Dry powder inhalers and other devices may be for single or multiple doses. Dry powders or powder-containing capsules may be used in the inhalers. Alternatively, the device may have the form of, for example, pressurized aerosol spray using a suitable gas such as chlorofluoroalkane or carbon dioxide appropriately as an ejection agent.

In oral administration, the appropriate daily dose is about 0.001 to 100 mg/kg body weight, preferably 0.1 to 30 mg/kg, and further preferably 0.1 to 10 mg/kg, and administered once or in two or four divided portions. In the case of intravenous administration, a daily dose is about 0.0001 to 10 mg/kg body weight and administered once or in several divided doses. As a transmucosal agent, a dose of about 0.001 to 100 mg/kg body weight is administered once or in a plurality of divided portions. The dose is appropriately determined on a case-by-case basis, in consideration of the symptom, age and gender.

The pharmaceutical composition of the present invention contains 0.01-100 wt %, or in some cases, 0.01-50 wt %, of one or more compounds of formula (I) or salts thereof as the active ingredient, although the content thereof varies depending on the route of administration, dosage form, site of administration, and type of excipient or additive.

A compound of formula (I) can be used in combination with various therapeutic agents or preventive agents for diseases to which the compound of formula (I) conceivably produces an effect. In the case of combination use, simultaneous administration or sequential administration with or without predetermined intervals may be made. A preparation for simultaneous administration may be a blending agent or consist of individual drug products.

EXAMPLES

Now, the production process for a compound of formula (I) will be more specifically described based on Examples. Note that, the present invention is not limited to the compounds described in the following Production Examples. The production processes for raw material compounds will be described below. The production process for a compound of formula (I) is not limited to those specifically described in Examples shown below. A compound of formula (I) can be produced also by combination of these production processes or a method obvious to those skilled in the art.

The onset temperature of the DSC curve obtained by measuring under the following conditions is shown in the table below as the melting point. DSC was measured using an aluminum sample pan and DSC Q2000 (manufactured by TA Instruments) under the conditions of measurement temperature range: 25 to 300° C., heating rate: 10° C./min, nitrogen flow rate: 50 mL/min. The measurement was performed without the lid on the aluminum sample pan.

The powder X-ray diffraction results described herein are obtained by measurement performed under the conditions of bulb: Cu, tube current: 40 mA, tube voltage: 45 kV, step width: 0.013°, wavelength: 1.5418 angstrom and measurement diffraction angle range (2θ): 2.5 to 40° using Empyrean (PANalytical). In the powder X-ray diffraction patterns described herein, crystal lattice intervals and general patterns are important due to the nature of the data for identification of crystals. In general, the diffraction angle may be within the error range of ±0.2°. Diffraction angles and diffraction intensity should not be taken in a strict sense because there may be some errors depending on the direction of crystal growth, the size of particles and the measurement conditions.

In Examples, Production Examples and the tables (described later), the following brevity codes are sometimes used.

PEx: Production Example No., Ex: Example No., PSyn: Production Example No. employing the same method, Syn: Example No. employing the same method, Str: chemical structural formula, DAT: physicochemical data, EI+: m/z value in mass spectrometry (electron ionization EI, unless otherwise specified, [M]+), ESI+: m/z value in mass spectrometry (ionization method ESI, unless otherwise specified, [M+H]+), ESI–: m/z value in mass spectrometry (ionization method ESI, unless otherwise specified [M–H]–), FAB: m/z value in mass spectrometry (ionization method FAB, unless otherwise specified [M+H]+), CI: m/z value in mass spectrometry (ionization method CI, unless otherwise specified [M+H]+), $^1$H-NMR (400 MHz, CDCl$_3$): δ value (ppm) of a signal in CDCl$_3$ by $^1$H-NMR, $^1$H-NMR (400 MHz, DMSO-d$_6$) and $^1$H-NMR (500 MHz, DMSO-d$_6$): δ value (ppm) of a signal in DMSO-d$_6$ by $^1$H-NMR, $^1$H-NMR (400 MHz, CD$_3$OD) and $^1$H-NMR (500 MHz, CD$_3$OD): δ value (ppm) of a signal in CD$_3$OD by $^1$H-NMR, J: coupling constant, s: singlet, d: doublet, t: triplet, q: quartet, dd: double-doublet, tt: triple-triplet, br: broad (example: br s), and m: multiplet, m.p.: melting point, 2θ: diffraction angle of peaks in powder X-ray diffraction.

In the tables (described later), in the columns of PSyn and Syn, hyphen (-) means that the production method is described as sentences in Production Example or Example.

In the tables (described later), in the column of chemical structural formula, a steric configuration marked with "#" means that the configuration is a relative configuration, and that other steric configurations are absolute steric configurations.

For convenience sake, concentration, mol/L will be shown by M. For example, 1 M aqueous sodium hydroxide solution means a 1 mol/L aqueous sodium hydroxide solution.

Production Example 1

A mixture of 3,6-dichloro-5-methyl-1,2,4-triazine (800 mg), (1R,2R)-2-aminocyclohexan-1-ol monohydrochloride (1.1 g), 1,4-dioxane (20 mL) and DIPEA (2.5 mL) was stirred at 100° C. for one hour under an argon atmosphere. To the reaction mixture, water was added and the mixture was extracted with chloroform. The organic layer was dried over anhydrous sodium sulfate and the solution was concentrated under reduced pressure. The obtained residue was purified by silica gel column chromatography (chloroform/methanol) to obtain (1R,2R)-2-[(6-chloro-5-methyl-1,2,4-triazin-3-yl)amino]cyclohexan-1-ol (710 mg), as a solid substance.

Production Example 11

A mixture of 3,6-dichloro-5-methyl-1,2,4-triazine (120 mg), 1,4-dioxane (5.0 mL), DIPEA (0.38 mL) and (3S,4R)-4-aminoxan-3-ol monohydrochloride (170 mg) was stirred at 100° C. for 2.5 hours under an argon atmosphere. To the reaction mixture, water was added and the mixture was extracted with chloroform. After the organic layer was concentrated under reduced pressure, the obtained residue was purified by silica gel column chromatography (chloroform/methanol) to obtain (3S,4R)-4-[(6-chloro-5-methyl-1,2,4-triazin-3-yl)amino]oxan-3-ol (90 mg), as an oily substance.

Production Example 53

A mixture of 3,6-dichloro-5-methyl-1,2,4-triazine (190 mg), (3R)-1-cyclopropylpiperidin-3-amine mono(trifluoroacetic acid) salt (290 mg), 1,4-dioxane (5 mL) and DIPEA (1 mL) was stirred at 100° C. for 2 hours (the mixture is designated as mixture A). A mixture of 3,6-dichloro-5-methyl-1,2,4-triazine (600 mg), (3R)-1-cyclopropylpiperidin-3-amine mono(trifluoroacetic acid) salt (930 mg), 1,4-dioxane (5 mL) and DIPEA (1.6 mL) was stirred at 100° C. for 2 hours (the mixture is designated as mixture B). Mixture A and mixture B were combined, and then, basic silica gel was added thereto. The mixture was concentrated under reduced pressure. The obtained residue was purified by silica gel column chromatography (chloroform/methanol) to obtain 6-chloro-N-[(3R)-1-cyclopropylpiperidin-3-yl]-5-methyl-1,2,4-triazin-3-amine (1.2 g), as a solid substance.

Production Example 55

A mixture of 3,6-dichloro-5-methyl-1,2,4-triazine (400 mg), (1S,3R)-3-aminocyclohexan-1-ol monohydrochloride (370 mg), DIPEA (0.84 mL) and 1,4-dioxane (5 mL) was stirred at 100° C. for 4 hours. To the reaction mixture, water was added and the mixture was extracted with chloroform. After the organic layer was concentrated under reduced pressure, the obtained residue was purified by silica gel column chromatography (chloroform/methanol) to obtain (1S,3R)-3-[(6-chloro-5-methyl-1,2,4-triazin-3-yl)amino]cyclohexan-1-ol (320 mg), as a solid substance.

Production Example 73

A mixture of 3,6-dichloro-5-methyl-1,2,4-triazine (150 mg), 1,4-dioxane (5 mL), tert-butyl [(1R,2R)-2-aminocyclohexyl]carbamate (290 mg) and DIPEA (0.48 mL) was stirred at 90° C. for 2.5 hours under an argon atmosphere. After allowed to cool to room temperature, the reaction mixture was poured in water and extracted with ethyl acetate. The organic layer was washed with a saturated aqueous sodium chloride solution, dried over anhydrous sodium sulfate and concentrated under reduced pressure. The obtained residue was purified by silica gel column chromatography (hexane/ethyl acetate) to obtain tert-butyl {(1R,2R)-2-[(6-chloro-5-methyl-1,2,4-triazin-3-yl)amino]cyclohexyl}carbamate (280 mg), as an oily substance.

Production Example 87

To a mixture of tert-butyl (2S)-2-(aminomethyl)morpholine-4-carboxylate (400 mg) and 1,4-dioxane (6 mL), 3,6-dichloro-5-methyl-1,2,4-triazine (200 mg) and DIPEA (0.32 mL) were added at room temperature. The mixture was stirred at 95 to 99° C. for 3 hours. After the reaction mixture was allowed to cool to room temperature, water was poured to the mixture, which was then extracted with ethyl acetate. The organic layer was washed with a saturated aqueous sodium chloride solution, dried over anhydrous sodium sulfate and concentrated under reduced pressure. The obtained residue was purified by silica gel column chromatography (hexane/ethyl acetate) to obtain tert-butyl (2S)-2-{[(6-chloro-5-methyl-1,2,4-triazin-3-yl)amino]methyl}morpholine-4-carboxylate (410 mg), as an oily substance.

Production Example 94

A mixture of 1-bromo-4-(difluoromethoxy)-2-(methoxymethoxy)benzene (920 mg), 1,4-dioxane (9.2 mL), bis(pinacolato)diboron (1.2 g), PdCl$_2$(dppf) (240 mg) and potassium acetate (960 mg) was stirred at 100° C. for 3 hours. After the reaction mixture was allowed to cool to room temperature, PdCl$_2$(dppf) (240 mg) was added thereto. The mixture was stirred at 100° C. for 2 hours. The obtained mixture was allowed to cool to room temperature, bis(pinacolato)diboron (620 mg) was added thereto. The mixture was stirred at 100° C. for 3 hours. After the reaction mixture was allowed to cool to room temperature, hexane was added thereto. The mixture was stirred at room temperature for 30 minutes. The obtained mixture was filtered with celite (registered trademark). The filtration was concentrated under reduced pressure to obtain 2-[4-(difluoromethoxy)-2-(methoxymethoxy)phenyl]-4,4,5,5-tetramethyl-1,3,2-dioxaborolane (2.0 g), as an oily substance. The substance was used in the following step without purification.

Production Example 97

To a mixture of tert-butyl [(3R)-1-cyclopropylpiperidin-3-yl]carbamate (3 g) and dichloromethane (20 mL), TFA (5.7 mL) was added on ice. The mixture was stirred at room temperature for 16 hours. To the reaction mixture, dichloromethane (10 mL) was added and TFA (5.7 mL) was added on ice. The mixture was stirred at room temperature for 2 hours. The reaction mixture was concentrated under reduced pressure. To the obtained residue, toluene was added, and then, the mixture was concentrated under reduced pressure. This operation was repeated three times to obtain (3R)-1-cyclopropylpiperidine-3-amine mono(trifluoroacetic acid) salt (3.2 g), as an oily substance.

Production Example 99

To a mixture of 5-cyclopropyl-3-(methylsulfanyl)-1,2,4-triazine (150 mg) and dichloromethane (3 mL), mCPBA (70%, 550 mg) was added on ice. The mixture was stirred at room temperature for 2 hours. To the reaction mixture, (1s,3s)-3-amino-1-methylcyclobutan-1-ol monohydrochloride (250 mg) and DIPEA (0.62 mL) were added and the reaction mixture was stirred at room temperature for 4 hours. To the obtained mixture, (1s,3s)-3-amino-1-methylcyclobutan-1-ol monohydrochloride (550 mg) and DIPEA (0.62 mL) were added and the reaction mixture was stirred at 50° C. for one hour. To the reaction mixture, a saturated aqueous sodium thiosulfate solution was added and the reaction mixture was extracted with chloroform. After the organic layer was concentrated under reduced pressure, the obtained residue was purified by silica gel column chromatography (chloroform/methanol) to obtain (1s,3s)-3-[(5-cyclopropyl-1,2,4-triazin-3-yl)amino]-1-methylcyclobutan-1-ol (170 mg), as a solid substance.

Production Example 105

To a mixture of (1s,3s)-3-[(5-cyclopropyl-1,2,4-triazin-3-yl)amino]-1-methylcyclobutan-1-ol (170 mg), acetonitrile (4 mL) and water (6 mL), NBS (270 mg) was added on ice. The mixture was stirred at room temperature for 18 hours. After the reaction mixture was concentrated under reduced pressure, the obtained residue was purified by silica gel column chromatography (chloroform/methanol) to obtain (1s,3s)-3-[(6-bromo-5-cyclopropyl-1,2,4-triazin-3-yl)amino]-1-methylcyclobutan-1-ol (180 mg), as a solid substance.

Production Example 117

A mixture of tert-butyl {(1R,2R)-2-[(6-chloro-5-methyl-1,2,4-triazin-3-yl)amino]cyclohexyl}carbamate (270 mg), [2-hydroxy-4-(trifluoromethyl)phenyl]boronic acid (330 mg), 1,4-dioxane (8 mL), water (2 mL), potassium carbonate (220 mg) and PdCl₂(dppf)·CH₂Cl₂ (65 mg) was stirred at 100 to 110° C. for 4 hours under an argon atmosphere. After allowed to cool to room temperature, the reaction mixture was poured in water and extracted with ethyl acetate. The organic layer was washed with a saturated aqueous sodium chloride solution, dried over anhydrous sodium sulfate and concentrated under reduced pressure. The obtained residue was purified by silica gel column chromatography (hexane/ethyl acetate) to obtain tert-butyl [(1R,2R)-2-({6-[2-hydroxy-4-(trifluoromethyl)phenyl]-5-methyl-1,2,4-triazin-3-yl}amino)cyclohexyl]carbamate (320 mg), as a solid substance.

Production Example 132

To a mixture of tert-butyl (2S)-2-([(6-chloro-5-methyl-1,2,4-triazin-3-yl)amino]methyl)morpholine-4-carboxylate (410 mg) and 1,4-dioxane (12 mL) and water (3 mL), [2-hydroxy-4-(trifluoromethyl)phenyl]boronic acid (490 mg), potassium carbonate (330 mg) and PdCl₂(dppf)

·CH₂Cl₂ (96 mg) were added at room temperature under an argon atmosphere. The mixture was stirred at 97 to 103° C. for 15 hours. After the reaction mixture was allowed to cool to room temperature, water was added to the reaction mixture, which was then extracted with ethyl acetate. The organic layer was washed with a saturated aqueous sodium chloride solution, dried over anhydrous sodium sulfate and concentrated under reduced pressure. The obtained residue was purified by silica gel column chromatography (hexane/ethyl acetate) to obtain tert-butyl (2S)-2-[({6-[2-hydroxy-4-(trifluoromethyl)phenyl]-5-methyl-1,2,4-triazin-3-yl}amino)methyl]morpholine-4-carboxylate (390 mg), as a solid substance.

Production Example 139

To a mixture of tert-butyl (3R,4R)-3-hydroxy-4-({6-[2-hydroxy-4-(trifluoromethyl)phenyl]-5-methyl-1,2,4-triazin-3-yl}amino)piperidine-1-carboxylate (400 mg) and dichloromethane (6 mL), TFA (1.5 mL) was added. The mixture was stirred at room temperature for 30 minutes. After the reaction mixture was concentrated under reduced pressure, the obtained residue was purified by silica gel column chromatography (basic silica gel, chloroform/methanol). To the purified product, ethyl acetate was added and the mixture was subjected to sonication. The solid precipitated was filtered to obtain (3R,4R)-4-({6-[2-hydroxy-4-(trifluoromethyl)phenyl]-5-methyl-1,2,4-triazin-3-yl}amino)piperidin-3-ol (170 mg), as a solid substance.

Production Example 141

To a mixture of 2-amino-5-cyclopropylphenol (3.5 g) and ethanol (50 mL), 12 M hydrochloric acid (16 mL) was added at −15° C. The mixture was stirred at the same temperature for 10 minutes. To the obtained mixture, amyl nitrite (9.6 mL) was added at −15° C., and the mixture was stirred at the same temperature for 30 minutes. To the obtained mixture, a mixture of potassium iodide (51 g) and water (50 mL) were added dropwise at −15° C. The mixture was stirred under an argon atmosphere for 20 hours while raising temperature from −15° C. to room temperature. The reaction mixture was extracted with ethyl acetate. The organic layer was washed sequentially with a saturated aqueous sodium thiosulfate solution and a saturated aqueous sodium chloride solution, and dried over anhydrous sodium sulfate. After the solution was concentrated under reduced pressure, the obtained residue was purified by silica gel column chromatography (hexane/ethyl acetate) to obtain 5-cyclopropyl-2-iodophenol (5 g), as an oily substance.

Production Example 142

A mixture of selenium dioxide (5.1 g), 1,1-difluoroacetone (3.2 mL), 1,4-dioxane (60 mL) and water (2 mL) was stirred at 100° C. for 16 hours under an argon atmosphere. After allowed to cool to room temperature, the reaction mixture was filtered with celite (registered trademark). To the obtained filtrate, water (14 mL) and sodium hydrogen carbonate (6.6 g) were added on ice. To the obtained mixture, a mixture of methyl hydrazinecarboximidothioate monohydroiodide (9.4 g) and water (81 mL) was added on ice. The mixture was stirred at room temperature for 2 days. After the reaction mixture was filtered, the filtrate was concentrated under reduced pressure. A saturated aqueous sodium thiosulfate solution was added to the obtained residue. The mixture was extracted with chloroform. The organic layer was dried over anhydrous sodium sulfate. After the solution was concentrated under reduced pressure, the obtained residue was purified by silica gel column chromatography (hexane/ethyl acetate) to obtain 5-(difluoromethyl)-3-(methylsulfanyl)-1,2,4-triazine (840 mg), as an oily substance.

Production Example 143

To a mixture of tert-butyl [(3R)-piperidin-3-yl]carbamate (5.1 g), THF (38 mL) and methanol (38 mL), [(1-ethoxy-cyclopropyl)oxy]tri(methyl)silane (10 mL) and acetic acid (7.3 mL) were added. The mixture was stirred at room temperature for 30 minutes. To the obtained mixture, sodium cyanoborohydride (2.4 g) was added and the mixture was stirred at 60° C. for 12 hours. After the reaction mixture was allowed to cool to room temperature, ice was added thereto. To the obtained mixture, water and a saturated aqueous sodium chloride solution were added. The mixture was extracted with ethyl acetate. The organic layer was washed with a saturated aqueous sodium chloride solution and dried over anhydrous sodium sulfate. After the solution was concentrated under reduced pressure, the obtained residue was purified by silica gel column chromatography (hexane/ethyl acetate) to obtain tert-butyl [(3R)-1-cyclopropylpiperidin-3-yl]carbamate (3 g), as a solid substance.

Production Example 144

To a mixture of 5-cyclopropyl-3-(methylsulfanyl)-1,2,4-triazine (450 mg) and dichloromethane (20 mL), mCPBA (70%, 1700 mg) was added on ice. The mixture was stirred at room temperature for 2 hours. To the reaction mixture, a saturated aqueous sodium thiosulfate solution was added, and then, the mixture was extracted with chloroform. After the organic layer was concentrated under reduced pressure, the obtained residue was purified by silica gel column chromatography (chloroform/methanol) to obtain 5-cyclopropyl-3-(methanesulfonyl)-1,2,4-triazine (590 mg), as a solid substance.

Production Example 145

A mixture of 5-cyclopropyl-3-(methanesulfonyl)-1,2,4-triazine (490 mg), DIPEA (1.6 mL), (3S)-3-aminopyrrolidin-2-one monohydrochloride (340 mg) and 1,4-dioxane (5 mL) was stirred at 90° C. for 4 hours under an argon atmosphere. After allowed to cool to room temperature, the reaction mixture was concentrated under reduced pressure. The obtained residue was purified by silica gel column chromatography (basic and neutral silica gel, chloroform/methanol) to obtain (3S)-3-[(5-cyclopropyl-1,2,4-triazin-3-yl)amino]pyrrolidin-2-one (210 mg), as a solid substance.

Production Example 150

A mixture of tert-butyl ((3R,4R)-3-hydroxy-4-({6-[2-hydroxy-4-(trifluoromethyl)phenyl]-5-methyl-1,2,4-triazin-3-yl}amino)pyrrolidine-1-carboxylate (500 mg), 1,4-dioxane (5.0 mL) and 4 M 1,4-dioxane solution of hydrogen chloride (5.0 mL) was stirred at room temperature for 16 hours under a nitrogen atmosphere. The reaction mixture was concentrated under reduced pressure to obtain (3R,4R)-4-({6-[2-hydroxy-4-(trifluoromethyl)phenyl]-5-methyl-1,2,4-triazin-3-yl}amino)pyrrolidin-3-ol monohydrochloride (500 mg), as a solid substance.

Production Example 151

To a mixture of ((3R,4R)-4-({6-[2-hydroxy-4-(trifluoromethyl)phenyl]-5-methyl-1,2,4-triazin-3-yl}amino)pyrrolidin-3-ol monohydrochloride (250 mg) and dichloromethane (10 mL), DIPEA (0.37 mL) and acetyl chloride (0.075 mL) were added at 0° C. under a nitrogen atmosphere. The mixture was stirred at room temperature for 3 hours. To the reaction mixture, ethyl acetate was added, and then, the mixture was washed sequentially with water, a saturated aqueous sodium chloride solution and a saturated aqueous sodium hydrogen carbonate solution. After the organic layer was dried over anhydrous sodium sulfate, the solution was concentrated under reduced pressure to obtain (3R,4R)-1-acetyl-4-({6-[2-hydroxy-4-(trifluoromethyl)phenyl]-5-methyl-1,2,4-triazin-3-yl}amino)pyrrolidin-3-yl acetate (280 mg), as a solid substance.

Production Example 152

To a mixture of tert-butyl [(3S,4R)-3-hydroxyoxan-4-yl]carbamate (3.7 g) and dichloromethane (46 mL), 1,1,1-triacetoxy-1,1-dihydro-1,2-benziodoxol-3-(1H)-one (8.8 g) was added on ice under an argon atmosphere. The mixture was stirred at the same temperature for 30 minutes. After the temperature of the reaction mixture was raised to room temperature, the reaction mixture was stirred for 2.5 hours. To the obtained mixture, 1,1,1-triacetoxy-1,1-dihydro-1,2-benziodoxol-3-(1H)-one (1.1 g) was added and the mixture was stirred at room temperature for one hour. To the reaction mixture, a saturated aqueous sodium sulfite solution was added on ice, and then, a saturated aqueous sodium hydrogen carbonate solution was added. The mixture was extracted with dichloromethane, and then, the organic layer was dried over anhydrous sodium sulfate. After concentrated under reduced pressure, the solution was purified by silica gel column chromatography (hexane/ethyl acetate) to obtain tert-butyl [(4R)-3-oxooxan-4-yl]carbamate (3.4 g), as a solid substance.

Production Example 153

To a mixture of tert-butyl [(4R)-3-oxooxan-4-yl]carbamate (2.8 g) and THF (42 mL), a 1 M THF solution of methylmagnesium bromide (32 mL) was added at a temperature of −73° C. to −65° C. under an argon atmosphere. The mixture was stirred for 4 hours while raising the temperature from −70° C. to 8° C. After the temperature of the reaction mixture was raised to room temperature, the mixture was stirred at the same temperature, overnight. To the obtained mixture, an aqueous ammonium chloride solution was added, and then, the mixture was extracted with ethyl acetate. The organic layer was washed with a saturated aqueous sodium chloride solution, and then, dried over anhydrous sodium sulfate. After concentrated under reduced pressure, the solution was purified by silica gel column chromatography (hexane/ethyl acetate). The obtained purified product was purified by reversed phase silica gel column chromatography (10 mM aqueous ammonium hydrogen carbonate solution/methanol) to obtain tert-butyl [(3S,4R)-3-hydroxy-3-methyloxan-4-yl]carbamate (830 mg), as a solid substance.

Production Example 154

To a mixture of tert-butyl [(3S,4R)-3-hydroxy-3-methyl-oxan-4-yl]carbamate (890 mg) and dichloromethane (3 mL), TFA (1 mL) was added. The mixture was stirred at room temperature for 2 hours. To the obtained mixture, TFA (0.50 mL) was added and the mixture was stirred for 2 hours at room temperature. After the reaction mixture was concentrated under reduced pressure, to the obtained residue, 1,4-dioxane (5 mL), 3,6-dichloro-5-methyl-1,2,4-triazine (630 mg) and DIPEA (2 mL) were added. The mixture was stirred at 100° C. for 1.5 hours. To the obtained mixture, basic silica gel was added, and then, the mixture was concentrated under reduced pressure. The obtained residue was purified with silica gel column chromatography (chloroform/methanol) to obtain (3S,4R)-4-[(6-chloro-5-methyl-1,2,4-triazin-3-yl)amino]-3-methyloxan-3-ol (380 mg), as an oily substance.

Production Example 155

To a mixture of potassium carbonate (1.7 g) and DMF (7.4 mL), a mixture of 4-bromo-3-(methoxymethoxy)phenol (1.9 g), sodium chlorodifluoroacetate (2.4 g) and DMF (11 mL) was added dropwise at 95° C. over one hour. The mixture was stirred at the same temperature for 15 minutes. After the reaction mixture was allowed to cool to room temperature, potassium carbonate (1.7 g) and sodium chlorodifluoroacetate (2.4 g) were added thereto. The mixture was stirred at 95° C. for one hour. After the obtained mixture was allowed to cool to room temperature, ethyl acetate and water were added thereto. The mixture was extracted with ethyl acetate. The organic layer was washed sequentially with water and a saturated aqueous sodium chloride solution, and dried over anhydrous sodium sulfate. After the solution was concentrated under reduced pressure, the obtained residue was purified by silica gel column chromatography (hexane/ethyl acetate) to obtain 1-bromo-4-(difluoromethoxy)-2-(methoxymethoxy)benzene (920 mg), as an oily substance.

Production Example 156

To a mixture of 6-[2-methoxy-4-(trifluoromethyl)phenyl]-5-methyl-N-{[(2S)-pyrrolidin-2-yl]methyl}-1,2,4-triazin-3-amine (220 mg) and dichloromethane (6 mL), DIPEA (0.16 mL) and acetic anhydride (0.085 mL) were added while stirring on ice. The mixture was stirred for 2 hours while the temperature of the mixture was allowed to rise naturally to room temperature. To the reaction mixture, a saturated aqueous ammonium chloride solution was added. The mixture was extracted with dichloromethane. The organic layer was dried over anhydrous sodium sulfate and concentrated under reduced pressure. The obtained residue was purified by silica gel column chromatography (dichloromethane/methanol) to obtain 1-{(2S)-2-[({6-[2-methoxy-4-(trifluoromethyl)phenyl]-5-methyl-1,2,4-triazin-3-yl}amino)methyl]pyrrolidin-1-yl}ethan-1-one (160 mg), as a solid substance.

Production Example 157

A mixture of 3-(methylsulfanyl)-5-(trifluoromethyl)-1,2,4-triazine (160 mg), 1,4-dioxane (6 mL) and (R)-(−)-1-amino-2-propanol (120 mg) was stirred at room temperature for 2 days. To the reaction mixture, (R)-(−)-1-amino-2-propanol (120 mg) and 1,4-dioxane (1 mL) were added and the mixture was stirred at room temperature for further one day. After the reaction mixture was concentrated under reduced pressure, the obtained residue was purified by silica gel column chromatography (hexane/ethyl acetate) to obtain (2R)-1-{[5-(trifluoromethyl)-1,2,4-triazin-3-yl]amino}propan-2-ol (91 mg), as an oily substance.

Production Example 158

To a mixture of (2R)-4-amino-2-methylbutan-1-ol (2.0 g) and THF (7 mL), di-tert-butyl dicarbonate (4.5 mL) was added dropwise while stirring on ice. The mixture was stirred for 2 hours while the temperature of the mixture was allowed to rise naturally to room temperature. After the reaction mixture was concentrated under reduced pressure, the obtained residue was purified by silica gel column chromatography (dichloromethane/methanol) to obtain tert-butyl [(3R)-4-hydroxy-3-methylbutyl]carbamate (3.6 g), as an oily substance.

Production Example 159

To a mixture of tert-butyl [(3R)-4-hydroxy-3-methyl-butyl]carbamate (1.8 g), dichloromethane (30 mL) and triethylamine (1.9 mL), methanesulfonyl chloride (1.1 mL) was added dropwise while stirring on ice. The mixture was stirred for 1.5 hours on ice. The temperature of the reaction mixture was raised to room temperature and a saturated aqueous sodium hydrogen carbonate solution (30 mL) was gradually added thereto. Thereafter, the mixture was extracted with dichloromethane. The organic layer was dried over anhydrous sodium sulfate, and then concentrated under reduced pressure to obtain (2R)-4-[(tert-butoxycarbonyl)amino]-2-methylbutyl methane sulfonate (2.7 g), as an oily substance.

Production Example 160

To a mixture of (2R)-4-[(tert-butoxycarbonyl)amino]-2-methylbutyl methane sulfonate (2.7 g) and DMF (16 mL), sodium azide (1.9 g) was added while stirring on ice. The temperature of the reaction mixture was raised to room temperature, and then, the mixture was stirred for 4 hours and stirred at a temperature of 47 to 56° C. for 17 hours. After the reaction mixture was allowed to cool to room temperature, water (30 mL) was added thereto. The mixture was extracted with ethyl acetate. The organic layer was washed with a saturated aqueous sodium chloride solution, dried over anhydrous sodium sulfate and concentrated under reduced pressure. The obtained residue was purified by silica gel column chromatography (hexane/ethyl acetate) to obtain tert-butyl [(3R)-4-azido-3-methylbutyl]carbamate (1.8 g), as an oily substance.

Production Example 161

A mixture of tert-butyl [(3R)-4-azido-3-methylbutyl]carbamate (1.8 g), THE (19 mL), water (1.5 mL) and triphenylphosphine (2.2 g) was stirred at room temperature for 16 hours. The reaction mixture was concentrated under reduced pressure and the obtained residue was purified by silica gel column chromatography (dichloromethane/methanol) to obtain tert-butyl [(3R)-4-amino-3-methylbutyl]carbamate (0.65 g), as an oily substance.

Production Example 162

To a mixture of tert-butyl {[1-(2-aminoethyl)cyclobutyl]methyl}carbamate (290 mg), dichloromethane (13 mL) and DIPEA (0.26 mL), acetic anhydride (0.14 mL) was added while stirring on ice. Thereafter, the mixture was stirred at room temperature for 6 hours. To the reaction mixture, water and 10% hydrochloric acid were added and the mixture was extracted with dichloromethane. The organic layer was dried over anhydrous sodium sulfate and the solution was concentrated under reduced pressure to obtain tert-butyl {[1-(2-acetamidoethyl)cyclobutyl]methyl}carbamate (360 mg), as an oily substance.

Production Example 165

A mixture of tert-butyl [(1R,3R)-3-cyanocyclopentyl]carbamate (180 mg) and an about 4 M 1,4-dioxane solution of hydrogen chloride (1 mL) was stirred at room temperature for 19 hours. The reaction mixture was concentrated under reduced pressure to obtain (1R,3R)-3-aminocyclopentane-1-carbonitrile monohydrochloride (150 mg), as a solid substance.

Production Example 169

To a mixture of (3R)-1-methylpiperidin-3-amine dihydrochloride (14 g) and 2-propanol (48 mL), DIPEA (37 mL) was added at room temperature and stirred at 80° C. for 10 minutes. To the mixture, a mixture of 3,6-dichloro-5-methyl-1,2,4-triazine (8.8 g) and 2-propanol (64 mL) was added dropwise at 80° C. and washed with 2-propanol (16 mL). The mixture was stirred at 80° C. for 2 hours. After the reaction mixture was allowed to cool to room temperature, water and saturated aqueous sodium chloride solution were added, and then, the mixture was extracted with chloroform. After the organic layer was dried over anhydrous magnesium sulfate and concentrated under reduced pressure, the obtained residue was purified by silica gel column chromatography (chloroform/methanol) to obtain 6-chloro-5-methyl-N-[(3R)-1-methylpiperidin-3-yl]-1,2,4-triazin-3-amine (8.8 g), as a solid substance.

Production Example 180

A mixture of 6-chloro-5-methyl-N-[(3R)-1-methylpiperidin-3-yl]-1,2,4-triazin-3-amine (4.5 g), 1,4-dioxane (90 mL), water (18 mL), 2-[4-(difluoromethoxy)-2-(methoxymethoxy)phenyl]-4,4,5,5-tetramethyl-1,3,2-dioxaborolane (12 g), RuPhos Pd G3 (1.6 g) and potassium carbonate (7.7 g) was stirred at 100° C. for 14 hours under an argon atmosphere. After the reaction mixture was allowed to cool to room temperature, chloroform/methanol (9/1) and water were added, which was stirred at room temperature for 10 minutes. After the organic layer was separated by adding saturated aqueous sodium chloride solution to the mixture, the organic layer was dried over anhydrous sodium sulfate. The reaction mixture was concentrated under reduced pressure and the obtained residue was purified by silica gel column chromatography (basic and neutral silica gel, hexane/ethyl acetate and chloroform/methanol) to obtain 6-[4-(difluoromethoxy)-2-(methoxymethoxy)phenyl]-5-methyl-N-[(3R)-1-methylpiperidin-3-yl]-1,2,4-triazin-3-amine (6.4 g), as a solid substance.

Production Example 190

To a mixture of 4-bromo-3-hydroxybenzaldehyde (2.9 g) and dichloromethane (30 mL), DIPEA (2.9 mL) and chloromethylmethylether (1.2 mL) were added, which was stirred at room temperature for 1 hour. To the reaction mixture, water was added and the organic layer was separated and concentrated under reduced pressure. The obtained residue was purified by silica gel column chromatography (hexane/ethyl acetate) to obtain 4-bromo-3-(methoxymethoxy)benzaldehyde (1.4 g), as an oily substance.

Production Example 192

To a mixture of 4-bromo-3-(methoxymethoxy)benzaldehyde (1.4 g) and dichloromethane (20 mL), diethylaminosulfur trifluoride (2.2 mL) was added on ice. After the mixture was stirred at the same temperature for 1 hour, the temperature of the reaction mixture was raised to room temperature, and then, the mixture was stirred for 3 hours. To the reaction mixture, a mixture of ice water, sodium bicarbonate and chloroform was added, which was stirred. After the organic layer was separated and concentrated under reduced pressure, the obtained residue was purified by silica gel column chromatography (hexane/ethyl acetate) to obtain 1-bromo-4-(difluoromethyl)-2-(methoxymethoxy) benzene (1.3 g), as an oily substance.

Production Example 193

To a mixture of 2-(5-methyl-3-{[(3R)-piperidin-3-yl]amino}-1,2,4-triazin-6-yl)-5-(trifluoromethyl)phenol (160 mg), dichloromethane (4.4 mL) and methanol (0.4 mL), tert-butyl 3-oxoazetidine-1-carboxylate (150 mg) was added, which was stirred at room temperature for 30 minutes. To the reaction mixture, sodium triacetoxyborohydride (190 mg) was added, which was stirred at room temperature for 21 hours. To the reaction mixture, tert-butyl 3-oxoazetidine-1-carboxylate (150 mg) and sodium triacetoxyborohydride (190 mg) were added, which was stirred at room temperature for 25 hours. To the reaction mixture, saturated aqueous sodium hydrogen carbonate solution was added, and the reaction mixture was extracted with dichloromethane. After the organic layer was dried over anhydrous sodium sulfate and concentrated under reduced pressure, the obtained residue was purified by silica gel column chromatography (dichloromethane/methanol) to obtain tert-butyl 3-[(3R)-3-({6-[2-hydroxy-4-(trifluoromethyl)phenyl]-5-methyl-1,2,4-triazin-3-yl}amino)piperidin-1-yl]azetidine-1-carboxylate (220 mg), as a solid substance.

Production Example 194

To a mixture of 1-(tert-butyloxycarbonyl)-5-({6-[2-hydroxy-4-(trifluoromethyl)phenyl]-5-methyl-1,2,4-triazin-3-yl}amino)piperidine-2-carboxylic acid (200 mg) and THF (2 mL), triethylamine (56 µL), methyl chloroformate (31 µL) and 25% aqueous ammonia (0.1 mL) were added while stirring on ice. The mixture was stirred for 6 hours while the temperature of the mixture was allowed to rise naturally to room temperature. To the reaction mixture, triethylamine (110 µL), methyl chloroformate (62 µL) and 25% aqueous ammonia (0.2 mL) were added, which was stirred at room temperature for 15 hours. The reaction mixture was concentrated under reduced pressure. After water was added to the residue, the mixture was extracted with ethyl acetate. The organic layer was washed with a saturated aqueous sodium chloride solution, dried over anhydrous sodium sulfate and concentrated under reduced pressure. The organic layer was washed with citric acid aqueous solution, saturated sodium hydrogen carbonate aqueous solution and saturated sodium chloride aqueous solution, dried with anhydrous sodium sulfate and concentrated under reduced pressure. The obtained residue was purified by silica gel column chromatography (ethyl acetate/methanol) to obtain tert-butyl 2-car-bamoyl-5-({6-[2-hydroxy-4-(trifluoromethyl)phenyl]-5-methyl-1,2,4-triazin-3-yl}amino)piperidine-1-carboxylate (80 mg), as a solid substance.

Production Example 195

To a mixture of 1-tert-butyl 2-methyl 5-({6-[2-hydroxy-4-(trifluoromethyl)phenyl]-5-methyl-1,2,4-triazin-3-yl}amino)piperidine-1,2-dicarboxylate (430 mg), THF (3.5 mL), methanol (0.7 mL) and water (2.5 mL), lithium hydroxide monohydrate (1.0 g) was added, which was stirred at 55 to 65° C. for 3.5 hours. After the reaction mixture was allowed to cool to room temperature, the reaction mixture was concentrated under reduced pressure. After water was added to the residue, 10% hydrochloric acid was gradually added to pH 3 while stirred at room temperature. After the organic layer was washed with a saturated aqueous sodium chloride solution, the organic layer was dried over anhydrous sodium sulfate and concentrated under reduced pressure to obtain 1-(tert-butoxycarbonyl)-5-({6-[2-hydroxy-4-(trifluoromethyl)phenyl]-5-methyl-1,2,4-triazin-3-yl}amino)piperidine-2-carboxylic acid (440 mg), as a solid substance.

Production Example 196

A mixture of tert-butyl (3R)-3-({6-[2-(acetyloxy)-4-(trifluoromethyl)phenyl]-5-methyl-1,2,4-triazin-3-yl}amino)piperidine-1-carboxylate (470 mg), dichloromethane (9 mL) and TFA (1 mL) was stirred at room temperature for 4.5 hours. The reaction mixture was concentrated under reduced pressure. After dichloromethane (12 mL) and ethyl bromo-acetate (0.3 mL) were added to the obtained residue, DIPEA (1.5 mL) was added dropwise and stirred at room temperature for 4 hours. To the reaction mixture, saturated aqueous sodium hydrogen carbonate solution was added, and the reaction mixture was extracted with dichloromethane. After the organic layer was dried over anhydrous sodium sulfate and concentrated under reduced pressure, the obtained residue was purified by silica gel column chromatography (hexane/ethyl acetate) to obtain ethyl [(3R)-3-({6-[2-(acetyloxy)-4-(trifluoromethyl)phenyl]-5-methyl-1,2,4-triazin-3-yl}amino)piperidine-yl]acetate (300 mg), as a solid substance.

Production Example 197

To a mixture of tert-butyl (3R)-3-({6-[2-hydroxy-4-(trifluoromethyl)phenyl]-5-methyl-1,2,4-triazin-3-yl}amino)piperidin-1-carboxylate (710 mg) and dichloromethane (10 mL), DIPEA (0.53 mL) and acetic anhydride (0.3 mL) were added at 0° C. The mixture was stirred for 5.5 hours while the temperature of the mixture was allowed to rise naturally to room temperature. After water was added to the reaction mixture, the mixture was extracted with dichloromethane. After the organic layer was dried over anhydrous sodium sulfate and concentrated under reduced pressure, the obtained residue was purified by silica gel column chromatography (hexane/ethyl acetate) to obtain tert-butyl (3R)-3-({6-[2-(acetyloxy)-4-(trifluoromethyl)phenyl]-5-methyl-1,2,4-triazin-3-yl}amino)piperidine-1-carboxylate (470 mg), as an oily substance.

Example 1

A mixture of (1R,2R)-2-[(6-chloro-5-methyl-1,2,4-triazin-3-yl)amino]cyclohexan-1-ol (710 mg), 1,4-dioxane (8.6 mL), water (2.1 mL), [2-hydroxy-4-(trifluoromethyl)phenyl]boronic acid (1.8 g), potassium carbonate (1.2 g) and RuPhos Pd G3 (250 mg) was stirred while applying microwave at 100° C. for one hour under an argon atmosphere. To the reaction mixture, RuPhos Pd G3 (120 mg) was added under an argon atmosphere. The mixture was stirred at 100° C. for one hour while applying microwave. Water was added to the mixture, which was then extracted with chloroform. After the organic layer was concentrated under reduced pressure, the obtained residue was purified by silica gel column chromatography (basic and neutral silica gel, chloroform/methanol) to obtain 2-(3-{[(1R,2R)-2-hydroxycyclohexyl]amino}-5-methyl-1,2,4-triazin-6-yl)-5-(trifluoromethyl)phenol (560 mg), as a solid substance.

Example 27

A mixture of (1R,2R)-2-[(6-chloro-5-methyl-1,2,4-triazin-3-yl)amino]cyclohexan-1-ol (170 mg), 1,4-dioxane (2.8 mL), water (0.70 mL), [2-hydroxy-4-(trifluoromethoxy)phenyl]boronic acid (200 mg), potassium carbonate (290 mg) and $PdCl_2(dppf) \cdot CH_2Cl_2$ (58 mg) was stirred while applying microwave at 100° C. for 2 hours under an argon atmosphere. After the reaction mixture was allowed to cool to room temperature, basic silica gel was added thereto. The mixture was concentrated under reduced pressure. The obtained residue was purified by silica gel column chromatography (basic and neutral silica gel, chloroform/methanol). To the purified product obtained, ethyl acetate and diisopropyl ether were added. The mixture was subjected to sonication. The precipitated solid substance was filtered to obtain 2-(3-{[(1R,2R)-2-hydroxycyclohexyl]amino}-5-methyl-1,2,4-triazin-6-yl)-5-(trifluoromethoxy)phenol (190 mg), as a solid substance.

Example 31

A mixture of (3S,4R)-4-[(6-chloro-5-methyl-1,2,4-triazin-3-yl)amino]oxan-3-ol (100 mg), 1,4-dioxane (2 mL), water (0.40 mL), (4-chloro-2-hydroxyphenyl)boronic acid (77 mg), potassium carbonate (180 mg) and $PdCl_2(dppf) \cdot CH_2Cl_2$ (35 mg) was stirred while applying microwave at 120° C. for one hour under an argon atmosphere. Water was added to the mixture, which was then extracted with chloroform. After the organic layer was concentrated under reduced pressure, the obtained residue was purified by silica gel column chromatography (basic and neutral silica gel, chloroform/methanol). To the purified product obtained, diisopropyl ether was added. The mixture was subjected to sonication. The precipitated solid substance was filtered to obtain (3S,4R)-4-{[6-(4-chloro-2-hydroxyphenyl)-5-methyl-1,2,4-triazin-3-yl]amino}oxan-3-ol (44 mg), as a solid substance.

Example 59

To a mixture of (1R,2R)-2-[(6-chloro-5-methyl-1,2,4-triazin-3-yl)amino]cyclohexan-1-ol (70 mg), 1,4-dioxane (2.8 mL), 5-methoxy-2-(4,4,5,5-tetramethyl-1,3,2-dioxaborolan-2-yl)phenol (87 mg), RuPhos Pd G3 (24 mg), potassium carbonate (120 mg) and water (0.56 mL) was stirred while applying microwave at 100° C. for one hour. After the reaction mixture was cooled to room temperature, chloroform and water were added thereto. The mixture was stirred at room temperature for 5 minutes. The obtained mixture was extracted with chloroform and the organic layer was dried over anhydrous sodium sulfate. After the solution was concentrated under reduced pressure, the obtained residue was purified by silica gel column chromatography (basic and neutral silica gel, chloroform/methanol). To the purified product obtained, diethyl ether (3 mL) and hexane (9 mL) were added. The mixture was stirred for 5 minutes. The precipitated solid substance was filtered to obtain 2-(3-{[(1R,2R)-2-hydroxycyclohexyl]amino}-5-methyl-1,2,4-triazin-6-yl)-5-methoxyphenol (80 mg), as a solid substance.

Example 73

A mixture of 6-chloro-N-[(3R)-1-cyclopropylpiperidin-3-yl]-5-methyl-1,2,4-triazin-3-amine (100 mg), 1,4-dioxane (3 mL), water (0.60 mL), [2-hydroxy-4-(trifluoromethyl)phenyl]boronic acid (94 mg), potassium carbonate (160 mg) and PdCl₂(dppf)·CH₂Cl₂ (31 mg) was stirred at 100° C. for 2 hours under an argon atmosphere. To the reaction mixture, basic silica gel was added. The mixture was concentrated under reduced pressure and the obtained residue was purified by silica gel column chromatography (basic and neutral silica gel, chloroform/methanol). To the purified product obtained, diisopropyl ether and hexane were added and the mixture was subjected to sonication. The precipitated solid substance was obtained by filtration (the solid is designated as solid A). The filtrate was concentrated under reduced pressure and hexane was added thereto. The mixture was subjected to sonication. The precipitated solid substance was obtained by filtration (the solid is designated as solid B). Solid A and solid B were combined to obtain 2-(3-{[(3R)-1-cyclopropylpiperidin-3-yl]amino}-5-methyl-1,2,4-triazin-6-yl)-5-(trifluoromethyl)phenol (45 mg), as a solid substance.

Example 75

A mixture of (1 S,3R)-3-[(6-chloro-5-methyl-1,2,4-triazin-3-yl)amino]cyclohexan-1-ol (120 mg), [2-hydroxy-4-(trifluoromethyl)phenyl]boronic acid (150 mg), RuPhos Pd G3 (42 mg), potassium carbonate (140 mg), 1,4-dioxane (2.4 mL) and water (0.60 mL) was stirred at 100° C. for 2 hours under an argon atmosphere. After the reaction mixture was allowed to cool to room temperature, basic silica gel was added thereto. The mixture was concentrated under reduced pressure. The obtained residue was purified by silica gel column chromatography (basic and neutral silica gel, chloroform/methanol). To the purified product obtained, diisopropyl ether and hexane were added. The mixture was subjected to sonication. The precipitated solid substance was filtered to obtain 2-(3-{[(1R,3S)-3-hydroxycyclohexyl]amino}-5-methyl-1,2,4-triazin-6-yl)-5-(trifluoromethyl)phenol (160 mg), as a solid substance.

Example 108

A mixture of (1s,3s)-3-[(6-bromo-5-cyclopropyl-1,2,4-triazin-3-yl)amino]-1-methylcyclobutan-1-ol (180 mg), [2-hydroxy-4-(trifluoromethyl)phenyl]boronic acid (380 mg), RuPhos Pd G3 (53 mg), potassium carbonate (340 mg), 1,4-dioxane (4 mL) and water (1 mL) was stirred at 70° C. for 5 hours under an argon atmosphere. To the reaction mixture, water was added and the mixture was extracted with chloroform. The organic layer was dried over anhydrous sodium sulfate. After the solution was concentrated under reduced pressure, the obtained residue was purified by silica gel column chromatography (basic and neutral silica gel, chloroform/methanol). To the purified product obtained, diisopropyl ether and hexane were added. The mixture was subjected to trituration. The precipitated solid substance was obtained by filtration and washed with hexane to obtain 2-(5-cyclopropyl-3-{[(1s,3s)-3-hydroxy-3-methylcyclobutyl]amino}-1,2,4-triazin-6-yl)-5-(trifluoromethyl)phenol (48 mg), as a solid substance.

Example 131

A mixture of (1R,2R)-2-[(6-chloro-5-methyl-1,2,4-triazin-3-yl)amino]cyclohexan-1-ol (99 mg), 1,4-dioxane (3 mL), water (0.60 mL), 2-[4-(difluoromethoxy)-2-(methoxymethoxy)phenyl]-4,4,5,5-tetramethyl-1,3,2-dioxaborolane (390 mg), RuPhos Pd G3 (35 mg) and potassium carbonate (170 mg) was stirred at 100° C. for 1.7 hours under an argon atmosphere. The reaction mixture was allowed to cool to room temperature and methanol (3 mL) and 12 M hydrochloric acid (2 mL) were added thereto at room temperature. The mixture was stirred at 60° C. for 2 hours. To the reaction mixture, basic silica gel was added. The reaction mixture was concentrated under reduced pressure. The obtained residue was purified by silica gel column chromatography (basic and neutral silica gel, chloroform/methanol). To the purified product obtained, diisopropyl ether was added. The mixture was subjected to sonication. The precipitated solid substance was filtered to obtain 5-(difluoromethoxy)-2-(3-{[(1R,2R)-2-hydroxycyclohexyl]amino}-5-methyl-1,2,4-triazin-6-yl)phenol (59 mg), as a solid substance.

Example 132

A mixture of tert-butyl [(1R,2R)-2-({6-[2-hydroxy-4-(trifluoromethyl)phenyl]-5-methyl-1,2,4-triazin-3-yl}amino)cyclohexyl]carbamate (310 mg), dichloromethane (7 mL) and trifluoroacetic acid (0.7 mL) was stirred at room temperature for 2 hours. To the reaction mixture, a saturated aqueous sodium hydrogen carbonate solution was added dropwise while stirring on ice. The mixture was extracted with a solvent mixture of dichloromethane/methanol=10/1. The organic layer was dried over anhydrous sodium sulfate, and then, concentrated under reduced pressure. The obtained residue was purified by silica gel column chromatography (dichloromethane/methanol) to obtain 2-(3-{[(1R,2R)-2-aminocyclohexyl]amino}-5-methyl-1,2,4-triazin-6-yl)-5-(trifluoromethyl)phenol (220 mg), as a solid substance.

Example 141

A mixture of tert-butyl (2S)-2-[({6-[2-hydroxy-4-(trifluoromethyl)phenyl]-5-methyl-1,2,4-triazin-3-yl}amino)methyl]morpholine-4-carboxylate (350 mg), dichloromethane (7 mL) and trifluoroacetic acid (1 mL) was stirred at room temperature for 2 hours. To the reaction mixture, trifluoroacetic acid (1 mL) was added while stirring under room temperature and stirred for 15 hours further at room temperature. To the reaction mixture, a saturated aqueous sodium hydrogen carbonate solution was added dropwise while stirring on ice. After methanol was added, the mixture was extracted with dichloromethane. The organic layer was dried over anhydrous sodium sulfate and concentrated under reduced pressure. The obtained residue was purified by silica gel column chromatography (dichloromethane/methanol) to obtain 2-[5-methyl-3-({[(2R)-morpholin-2-yl]methyl}amino)-1,2,4-triazin-6-yl]-5-(trifluoromethyl)phenol (210 mg), as a solid substance.

Example 148

To a mixture of tert-butyl [(2R)-1-({6-[2-hydroxy-4-(trifluoromethyl)phenyl]-5-methyl-1,2,4-triazin-3-yl}amino)

propan-2-yl]carbamate (140 mg) and dichloromethane (5.0 mL), 4 M 1,4-dioxane solution of hydrogen chloride (1.0 mL) was added at 0° C. The mixture was stirred at room temperature for 4 hours. After the reaction mixture was concentrated under reduced pressure, the obtained residue was washed with diethyl ether to obtain 2-(3-{[(2R)-2-aminopropyl]amino}-5-methyl-1,2,4-triazin-6-yl)-5-(trifluoromethyl)phenol monohydrochloride (70 mg), as a solid substance.

Example 149

A mixture of 2-(5-methyl-3-{[1-(oxan-2-yl)-1H-pyrazol-4-yl]amino}-1,2,4-triazin-6-yl)-5-(trifluoromethyl)phenol (210 mg), dichloromethane (5 mL) and trifluoroacetic acid (0.5 mL) was stirred at room temperature for 4 hours. To the reaction mixture, trifluoroacetic acid (0.5 mL) was added at room temperature. The mixture was stirred for 2 hours further at room temperature. To the reaction mixture, a saturated aqueous sodium hydrogen carbonate solution was added dropwise while stirring on ice. The precipitated solid substance was obtained by filtration and washed with water. To the obtained solid substance, dichloromethane and hexane were added. The mixture was subjected to trituration. The precipitated solid substance was filtered to obtain 2-{5-methyl-3-[(1H-pyrazol-4-yl)amino]-1,2,4-triazin-6-yl}-5-(trifluoromethyl)phenol (140 mg), as a solid substance.

Example 151

To a mixture of 1-{(2S)-2-[({6-[2-methoxy-4-(trifluoromethyl)phenyl]-5-methyl-1,2,4-triazin-3-yl}amino)methyl]pyrrolidin-1-yl}ethan-1-one (150 mg) and dichloromethane (1.8 mL), boron tribromide (17% dichloromethane solution, 1.8 mL) was added dropwise while stirring on ice. The reaction mixture was stirred for 2 hours while the temperature of the mixture was allowed to rise naturally to room temperature. To the reaction mixture, a saturated aqueous sodium hydrogen carbonate solution was added dropwise while stirring on ice. After the temperature of the mixture was raised to room temperature, the mixture was extracted with dichloromethane. The organic layer was dried over anhydrous sodium sulfate and concentrated under reduced pressure. The obtained residue was purified by silica gel column chromatography (dichloromethane/methanol) to obtain 1-((2S)-2-[({6-[2-hydroxy-4-(trifluoromethyl)phenyl]-5-methyl-1,2,4-triazin-3-yl}amino)methyl]pyrrolidin-1-yl)ethan-1-one (120 mg), as a solid substance.

Example 152

To a mixture of 2-(3-{[(1R,2R)-2-aminocyclohexyl]amino}-5-methyl-1,2,4-triazin-6-yl)-5-(trifluoromethyl)phenol (210 mg) and dichloromethane (6 mL), DIPEA (0.2 mL) and acetic anhydride (0.1 mL) were added while stirring on ice. The reaction mixture was stirred for 14 hours while the temperature of the mixture was allowed to rise naturally to room temperature. After the reaction mixture was concentrated under reduced pressure, methanol (2 mL), water (0.2 mL) and potassium carbonate (160 mg) were added thereto.

The mixture was stirred at room temperature for 21 hours and concentrated under reduced pressure. Dichloromethane, 10% hydrochloric acid and a saturated aqueous sodium hydrogen carbonate solution were added to the mixture, which was then extracted with dichloromethane. The organic layer was dried over anhydrous sodium sulfate and concentrated under reduced pressure. The obtained residue was purified by silica gel column chromatography (dichloromethane/methanol) to obtain N-[(1R,2R)-2-({6-[2-hydroxy-4-(trifluoromethyl)phenyl]-5-methyl-1,2,4-triazin-3-yl}amino)cyclohexyl]acetamide (170 mg), as a solid substance.

Example 159

To a mixture of (3R,4R)-4-({6-[2-hydroxy-4-(trifluoromethyl)phenyl]-5-methyl-1,2,4-triazin-3-yl}amino)piperidin-3-ol (52 mg) and dichloromethane (5 mL), acetyl chloride (0.050 mL) was added at 0° C. The mixture was stirred at a temperature of 0° C. to 10° C. for 3 hours. The temperature of the reaction mixture was raised to room temperature and the mixture was stirred at the same temperature for 1.5 hours. To the obtained mixture, pyridine (0.011 mL) was added and the mixture was stirred at room temperature for 3 days. To the reaction mixture, 1 M aqueous sodium hydroxide solution (1.3 mL) was added and the mixture was stirred at room temperature for 2 days. To the obtained mixture, 1M hydrochloric acid (1.3 mL) was added at 0° C. and the mixture was extracted with chloroform. After the organic layer was concentrated under reduced pressure, the obtained residue was purified by silica gel column chromatography (chloroform/methanol) to obtain 1-[(3R,4R)-3-hydroxy-4-({6-[2-hydroxy-4-(trifluoromethyl)phenyl]-5-methyl-1,2,4-triazin-3-yl}amino)piperidin-1-yl]ethan-1-one (16 mg), as a solid substance.

Example 160

A mixture of (3R,4R)-4-((6-[2-hydroxy-4-(trifluoromethyl)phenyl]-5-methyl-1,2,4-triazin-3-yl)amino)pyrrolidin-3-ol monohydrochloride (250 mg), dichloromethane (5.0 mL), DIPEA (0.18 mL) and methanesulfonyl chloride (0.054 mL) was stirred at room temperature for 3 hours, under a nitrogen atmosphere. After the reaction mixture was concentrated under reduced pressure, the obtained residue was purified by reversed phase silica gel column chromatography (0.1% TFA aqueous solution/acetonitrile) to obtain (3R,4R)-4-({6-[2-hydroxy-4-(trifluoromethyl)phenyl]-5-methyl-1,2,4-triazin-3-yl}amino)-1-(methanesulfonyl)pyrrolidin-3-ol (9 mg), as a solid substance.

Example 161

To a mixture of 2-(5-methyl-3-{[(3R)-pyrrolidin-3-yl]amino}-1,2,4-triazin-6-yl)-5-(trifluoromethyl)phenol (120 mg), 1,4-dioxane-2,5-diol (85 mg), dichloromethane (3 mL) and acetic acid (0.40 mL), sodium triacetoxyborohydride (150 mg) was added under an argon atmosphere. The mixture was stirred at room temperature for 2 hours. To the reaction mixture, water was added and the mixture was extracted with chloroform. After the organic layer was concentrated under reduced pressure, the obtained residue was purified by silica gel column chromatography (chloroform/methanol) to obtain 2-(3-{[(3R)-1-(2-hydroxyethyl)pyrrolidin-3-yl]amino}-5-methyl-1,2,4-triazin-6-yl)-5-(trifluoromethyl)phenol (10 mg), as a solid substance.

Example 163

To a mixture of (3R,4R)-1-acetyl-4-({6-[2-hydroxy-4-(trifluoromethyl)phenyl]-5-methyl-1,2,4-triazin-3- yl}amino)pyrrolidin-3-yl acetate (250 mg) and methanol (10 mL), potassium carbonate (240 mg) was added at 0° C. under a nitrogen atmosphere. The mixture was stirred at room temperature for 16 hours. The reaction mixture was filtered with celite (registered trademark) and washed with ethyl acetate. The filtrate was concentrated under reduced pressure. The obtained residue was purified by silica gel column chromatography (dichloromethane/methanol) to obtain 1-[(3R,4R)-3-hydroxy-4-({6-[2-hydroxy-4-(trifluoromethyl)phenyl]-5-methyl-1,2,4-triazin-3-yl}amino)pyrrolidin-1-yl]ethan-1-one (45 mg), as a solid substance.

Example 164

To a mixture of [2-hydroxy-4-(trifluoromethyl)phenyl] boronic acid (4.5 g) and 1,4-dioxane (30 mL), 6-chloro-5-methyl-N-[(3R)-1-methylpiperidin-3-yl]-1,2,4-triazin-3-amine (3.5 g), RuPhos Pd G3 (1.3 g), potassium carbonate (6.0 g) and water (6 mL) were added at room temperature and stirred overnight at 100° C. under an argon atmosphere. After the reaction mixture was allowed to cool to room temperature, water and saturated aqueous sodium chloride solution were added to the reaction liquid, the mixture was extracted with chloroform. The organic layer was dried over anhydrous magnesium sulfate. After the reaction mixture was concentrated under reduced pressure, the obtained residue was purified by silica gel column chromatography (basic and neutral silica gel, and chloroform/methanol). The purified substance was suspended in ethyl acetate/hexane and filtered to obtain 2-5-methyl-3-{[(3R)-1-methylpiperidin-3-yl]amino}-1,2,4-triazin-6-yl)-5-(trifluoromethyl)phenol (3.0 g), as a solid substance.

Example 174

To a mixture of 6-[4-(difluoromethoxy)-2-(methoxymethoxy)phenyl]-5-methyl-N-[(3R)-1-methylpiperidin-3-yl]-1,2,4-triazin-3-amine (5.4 g) and methanol (50 mL), 12M hydrochloric acid (10 mL) was added at room temperature and stirred at 60° C. for 1.5 hours. The reaction mixture was cooled with ice, and saturated aqueous sodium hydrogen carbonate solution (300 mL) was added to the mixture and stirred at room temperature for 30 minutes. The obtained mixture was extracted with chloroform and chloroform/methanol (9/1). The combined organic layer was washed with saturated aqueous sodium chloride solution and dried with anhydrous sodium sulfate. After the mixture was concentrated under reduced pressure, the obtained residue was dissolved with chloroform/methanol (9/1), and basic silica gel was added. After the mixture was concentrated under reduced pressure, the obtained residue was purified by silica gel column chromatography (basic and neutral silica gel, and chloroform/methanol). To the purified substance, ethyl acetate (36 mL) was added, and the mixture was stirred at 80° C. To the mixture, heptane (180 mL) was added at the same temperature. After the mixture was allowed to cool to room temperature, the solid substance was filtered to obtain 5-(difluoromethoxy)-2-(5-methyl-3-{[(3R)-1-methylpiperidin-3-yl]amino}-1,2,4-triazin-6-yl)phenol (3.0 g), as a solid substance.

Example 181

To a mixture of 2-(5-methyl-3-{[(3R)-piperidin-3-yl]amino}-1,2,4-triazin-6-yl)-5-(trifluoromethyl)phenol (100 mg), dichloromethane (1.5 mL) and methanol (0.15 mL), acrylonitrile (28 µL) was added, which was stirred at room temperature for 6 hours. To the mixture, acrylonitrile (160 µL) was added, which was stirred at room temperature for 26 hours. After the reaction mixture was concentrated under reduced pressure, the obtained residue was purified by silica gel column chromatography (dichloromethane/methanol) to obtain 3-[(3R)-3-({6-[2-hydroxy-4-(trifluoromethyl)phenyl]-5-methyl-1,2,4-triazin-3-yl}amino)piperidin-1-yl]propanenitrile (31 mg), as a solid substance.

Example 182

To a mixture of methyl (1S,3R)-3-({6-[2-hydroxy-4-(trifluoromethyl)phenyl]-5-methyl-1,2,4-triazin-3-yl}amino)cyclopentane-1-carboxylate (250 mg), THF (3 mL) and water (1.5 mL), lithium hydroxide monohydrate (65 mg) was added, which was stirred at room temperature for 17 hours. To the reaction mixture, 10% hydrochloric acid was added to pH 2 to 3. Water was added to the mixture, which was then extracted with ethyl acetate. The organic layer was washed with saturated sodium chloride aqueous solution and dried over anhydrous sodium sulfate (this organic layer is referred to as organic layer A). To a mixture of methyl (1S,3R)-3-({6-[2-hydroxy-4-(trifluoromethyl)phenyl]-5-methyl-1,2,4-triazin-3-yl}amino)cyclopentane-1-carboxylate (55 mg), THF (0.7 mL) and water (0.35 mL), lithium hydroxide monohydrate (15 mg) was added, which was stirred at room temperature for 17 hours. To the reaction mixture, 10% hydrochloric acid was added to pH 2 to 3. Water was added to the mixture, which was then extracted with ethyl acetate. The organic layer was washed with saturated sodium chloride aqueous solution and dried over anhydrous sodium sulfate (this organic layer is referred to as organic layer B). After the organic layers A and B were combined and concentrated under reduced pressure, the obtained residue was purified by silica gel column chromatography (hexane/ethyl acetate) to obtain (1S,3R)-3-({6-[2-hydroxy-4-(trifluoromethyl)phenyl]-5-methyl-1,2,4-triazin-3-yl}amino)cyclopentane-1-carboxylic acid (190 mg), as a solid substance.

Example 184

To a mixture of 2-(3-{[(1R,2R)-2-hydroxycyclohexyl]amino}-5-methyl-1,2,4-triazin-6-yl)-5-methoxyphenol (200 mg) and ethanol (1 mL), 4M hydrogen chloride ethyl acetate solution (0.23 mL) was added, which was stirred at room temperature for 10 minutes. After the reaction liquid was concentrated under reduced pressure, ethyl acetate (2 mL) was added to the residue and stirred at 50° C. for 48 hours. After the reaction mixture was allowed to cool to room temperature, the solid substance was filtered and washed with cold ethyl acetate (1 mL) to obtain 2-(3-{[(1R,2R)-2-hydroxycyclohexyl]amino}-5-methyl-1,2,4-triazin-6-yl)-5-methoxyphenol monohydrochloride (170 mg), as a crystal.

Example 185

To a mixture of 2-(3-{[(1R,3S)-3-hydroxycyclohexyl]amino}-5-methyl-1,2,4-triazin-6-yl)-5-(trifluoromethyl)phenol (100 mg), dichloromethane (2 mL) and 1,4-dioxane (1 mL), 4M hydrogen chloride 1,4-dioxane solution (0.082 mL) was added, which was stirred at room temperature for 2 hours. After the reaction liquid was concentrated under reduced pressure, 2-butanone (2 mL) was added to the residue and stirred at 50° C. for 72 hours. After the reaction mixture was allowed to cool to room temperature, the solid substance was filtered and washed with cold 2-butanone (1 mL) to obtain 2-(3-{[(1R,3S)-3-hydroxycyclohexyl]amino}-5-methyl-1,2,4-triazin-6-yl)-5-(trifluoromethyl)phenol monohydrochloride (31 mg), as a crystal.

Example 186

To a mixture of 5-(difluoromethoxy)-2-(3-{[(1R,2R)-2-hydroxycyclohexyl]amino}-5-methyl-1,2,4-triazin-6-yl)phenol (200 mg) and ethanol (1 mL), 4M hydrogen chloride ethyl acetate solution (0.2 mL) was added, which was stirred at room temperature for 10 minutes. After the reaction liquid was concentrated under reduced pressure, ethyl acetate (2 mL) was added to the residue and stirred at 50° C. for 48 hours. After the reaction mixture was allowed to cool to room temperature, the solid substance was filtered and washed with cold ethyl acetate (1 mL) to obtain 5-(difluoromethoxy)-2-(3-{[(1R,2R)-2-hydroxycyclohexyl]amino}-5-methyl-1,2,4-triazin-6-yl)phenol monohydrochloride (160 mg), as a crystal.

Example 187

To a mixture of 2-(5-methyl-3-{[(3R)-1-methylpiperidin-3-yl]amino}-1,2,4-triazin-6-yl)-5-(trifluoromethyl)phenol (200 mg) and ethanol (1 mL), 4M hydrogen chloride ethyl acetate solution (0.34 mL) was added, which was stirred at room temperature for 10 minutes. After the reaction liquid was concentrated under reduced pressure, ethyl acetate (2 mL) was added to the residue and stirred at 50° C. for 48 hours. After the reaction mixture was allowed to cool to room temperature, the solid substance was filtered and washed with cold ethyl acetate (1 mL) to obtain 2-(5-methyl-3-{[(3R)-1-methylpiperidin-3-yl]amino}-1,2,4-triazin-6-yl)-5-(trifluoromethyl)phenol dihydrochloride (160 mg), as a crystal.

Example 188

To a mixture of 2-(3-{[(1R,2R)-2-aminocyclohexyl]amino}-5-methyl-1,2,4-triazin-6-yl)-5-(trifluoromethyl)phenol (960 mg) and ethyl acetate (3 mL), 4M hydrogen chloride 1,4-dioxane solution (1.4 mL) and ethyl acetate (3 mL) were added, which was stirred at room temperature for 2 hours. To the reaction mixture, ethyl acetate was added, and the precipitated solid was obtained by filtration and dried to obtain a crude product (880 mg) as a solid. A mixture of the crude product (180 mg) and ethyl acetate (2 mL) was stirred at 50° C. for 62 hours. After the reaction mixture was allowed to cool to room temperature, the precipitated solid substance was filtered to obtain 2-(3-{[(1R,2R)-2-aminocyclohexyl]amino}-5-methyl-1,2,4-triazin-6-yl)-5-(trifluoromethyl)phenol dihydrochloride (45 mg), as a crystal.

Compounds of Production Examples and Examples listed in the tables below were prepared in the same manner as in the above-described Production Examples or Examples.

TABLE 3-1

| PEx | Str |
|---|---|
| 1 | |

TABLE 3-1-continued

| PEx | Str |
|---|---|
| 2 | |
| 3 | |
| 4 | |
| 5 | |
| 6 | |
| 7 | |
| 8 | |

TABLE 3-1-continued

| PEx | Str |
|---|---|
| 9 | |
| 10 | |
| 11 | |
| 12 | |
| 13 | |
| 14 | |
| 15 | |

TABLE 3-1-continued

| PEx | Str |
|---|---|
| 16 | |
| 17 | |
| 18 | |
| 19 | |
| 20 | |

TABLE 3-2

| PEx | Str |
|---|---|
| 21 | |
| 22 | |

TABLE 3-2-continued

| PEx | Str |
|-----|-----|
| 23 | |
| 24 | |
| 25 | |
| 26 | |
| 27 | |
| 28 | |
| 29 | |

TABLE 3-2-continued

| PEx | Str |
|-----|-----|
| 30 | |
| 31 | |
| 32 | # |
| 33 | |
| 34 | |
| 35 | |
| 36 | |

TABLE 3-2-continued

| PEx | Str |
| --- | --- |
| 37 | |
| 38 | |
| 39 | |
| 40 | |

TABLE 3-3

| PEx | Str |
| --- | --- |
| 41 | |
| 42 | |

TABLE 3-3-continued

| PEx | Str |
| --- | --- |
| 43 | |
| 44 | |
| 45 | |
| 46 | |
| 47 | |
| 48 | # | |
| 49 | |

55

TABLE 3-3-continued

| PEx | Str |
|---|---|
| 50 | |
| 51 | |
| 52 # | |
| 53 | |
| 54 | |
| 55 | |
| 56 # | |

56

TABLE 3-3-continued

| PEx | Str |
|---|---|
| 57 | |
| 58 | |
| 59 | |
| 60 | |

TABLE 3-4

| PEx | Str |
|---|---|
| 61 | |
| 62 | |

57

58

TABLE 3-4-continued

TABLE 3-4-continued

| PEx | Str |
|---|---|
| 63 | |
| 64 | |
| 65 | |
| 66 | |
| 67 | |
| 68 | |
| 69 | |
| 70 | |

| PEx | Str |
|---|---|
| 71 | |
| 72 | |
| 73 | |
| 74 | |
| 75 | |
| 76 | |

59

TABLE 3-4-continued

| PEx | Str |
|-----|-----|
| 77 | |
| 78 | |
| 79 | |
| 80 | |

TABLE 3-5

| PEx | Str |
|-----|-----|
| 81 | |
| 82 | |

60

TABLE 3-5-continued

| PEx | Str |
|-----|-----|
| 83 | |
| 84 | |
| 85 | |
| 86 | |
| 87 | |
| 88 | |

61

62

TABLE 3-5-continued

TABLE 3-5-continued

| PEx | Str |
| --- | --- |
| 89 | |
| 90 | |
| 91 | |
| 92 | |
| 93 | |
| 94 | |

| PEx | Str |
| --- | --- |
| 95 | |
| 96 | |
| 97 | |
| 98 | |
| 99 | |
| 100 | |

TABLE 3-6

| PEx | Str |
| --- | --- |
| 101 | |

TABLE 3-6-continued

| PEx | Str |
|-----|-----|
| 102 | |
| 103 | |
| 104 | |
| 105 | |
| 106 | |
| 107 | |

TABLE 3-6-continued

| PEx | Str |
|-----|-----|
| 108 | |
| 109 | |
| 110 | |
| 111 | |
| 112 | |
| 113 | |

TABLE 3-6-continued

| PEx | Str |
| --- | --- |
| 114 | |
| 115 | |
| 116 | |

TABLE 3-6-continued

| PEx | Str |
| --- | --- |
| 117 | |
| 118 | |
| 119 | |
| 120 | |

TABLE 3-7

| PEx | Str |
| --- | --- |
| 121 | |
| 122 | |
| 123 | |

TABLE 3-7-continued

| PEx | Str |
| --- | --- |
| 124 | |
| 125 | |
| 126 | |
| 127 | |
| 128 | |
| 129 | |

TABLE 3-7-continued

| PEx | Str |
|---|---|
| 130 | |
| 131 | |
| 132 | |
| 133 | |
| 134 | |
| 135 | |

TABLE 3-7-continued

| PEx | Str |
|---|---|
| 136 | |
| 137 | |
| 138 | |
| 139 | |
| 140 | |

TABLE 3-8

| PEx | Str |
|---|---|
| 141 | |
| 142 | |

TABLE 3-8-continued

| PEx | Str |
|---|---|
| 143 | |
| 144 | |

73

TABLE 3-8-continued

| PEx | Str |
| --- | --- |
| 145 | |
| 146 | |
| 147 | |
| 148 | |
| 149 | |
| 150 | HCl |

74

TABLE 3-8-continued

| PEx | Str |
| --- | --- |
| 151 | |
| 152 | |
| 153 | |
| 154 | |
| 155 | |
| 156 | |
| 157 | |


75

TABLE 3-8-continued

| PEx | Str |
|---|---|
| 158 | |
| 159 | |
| 160 | |

TABLE 3-9

| PEx | Str |
|---|---|
| 161 | |
| 162 | |
| 163 | |

76

TABLE 3-9-continued

| PEx | Str |
|---|---|
| 164 | |
| 165 | |
| 166 | |
| 167 | |
| 168 | |

TABLE 3-10

| PEx | Str |
|---|---|
| 169 | |
| 170 | |

77

TABLE 3-10-continued

| PEx | Str |
|---|---|
| 171 | |
| 172 | |
| 173 | |
| 174 | |
| 175 | |
| 176 | |
| 177 | |

78

TABLE 3-10-continued

| PEx | Str |
|---|---|
| 178 | |
| 179 | |
| 180 | |
| 181 | |
| 182 | |
| 183 | |
| 184 | |

79

80

TABLE 3-10-continued

TABLE 3-10-continued

| PEx | Str |
| --- | --- |
| 185 | |
| 186 | |

| PEx | Str |
| --- | --- |
| 187 | |
| 188 | |

TABLE 3-11

| PEx | Str |
| --- | --- |
| 189 | |
| 190 | |
| 191 | |
| 192 | |

TABLE 3-11-continued

| PEx | Str |
| --- | --- |
| 193 | |
| 194 | |
| 195 | |
| 196 | |
| 197 | |

TABLE 4-1

| Ex | Str |
| --- | --- |
| 1 | |

TABLE 4-1-continued

| Ex | Str |
| --- | --- |
| 2 | |

83

TABLE 4-1-continued

| Ex | Str |
|----|-----|
| 3 | |
| 4 | |
| 5 | |
| 6 | |
| 7 | |
| 8 | |
| 9 | |

84

TABLE 4-1-continued

| Ex | Str |
|----|-----|
| 10 | |
| 11 | |
| 12 | |
| 13 | |
| 14 | |
| 15 | |
| 16 | |

85

TABLE 4-1-continued

| Ex | Str |
|---|---|
| 17 | |
| 18 | |
| 19 | |
| 20 | |

TABLE 4-2

| Ex | Str |
|---|---|
| 21 | |
| 22 | |
| 23 | |

86

TABLE 4-2-continued

| Ex | Str |
|---|---|
| 24 | |
| 25 | |
| 26 | |
| 27 | |
| 28 | |
| 29 | |
| 30 | |

87

88

TABLE 4-2-continued

TABLE 4-2-continued

| Ex | Str |
|----|-----|
| 31 | |
| 32 | |
| 33 | |
| 34 | |
| 35 | |
| 36 | |
| 37 | |

| Ex | Str |
|----|-----|
| 38 | |
| 39 | # |
| 40 | |

TABLE 4-3

| Ex | Str |
|----|-----|
| 41 | |
| 42 | |
| 43 | |
| 44 | |

TABLE 4-3-continued | TABLE 4-3-continued

| Ex | Str |
|----|-----|
| 45 | |
| 46 | |
| 47 | |
| 48 | |
| 49 | |
| 50 | |
| 51 | |

| Ex | Str |
|----|-----|
| 52 | |
| 53 | |
| 54 | |
| 55 | |
| 56 | |
| 57 | |
| 58 | |

TABLE 4-3-continued

| Ex | Str |
|---|---|
| 59 | |
| 60 | |

TABLE 4-4

| Ex | Str |
|---|---|
| 61 | |
| 62 | |
| 63 | |
| 64 # | |

TABLE 4-4-continued

| Ex | Str |
|---|---|
| 65 | |
| 66 | |
| 67 | |
| 68 | |
| 69 # | |
| 70 | |
| 71 | |

TABLE 4-4-continued

| Ex | Str |
|----|-----|
| 72 | |
| 73 | |
| 74 | |
| 75 | |
| 76 | # |
| 77 | |
| 78 | |

TABLE 4-4-continued

| Ex | Str |
|----|-----|
| 79 | |
| 80 | |

TABLE 4-5

| Ex | Str |
|----|-----|
| 81 | |
| 82 | |
| 83 | |
| 84 | |
| 85 | |

95

TABLE 4-5-continued

| Ex | Str |
|---|---|
| 86 | |
| 87 | |
| 88 | |
| 89 | |
| 90 | |
| 91 | |
| 92 | |

96

TABLE 4-5-continued

| Ex | Str |
|---|---|
| 93 | |
| 94 | |
| 95 | |
| 96 | |
| 97 | |
| 98 | |
| 99 | |

TABLE 4-5-continued

| Ex | Str |
|---|---|
| 100 | |

TABLE 4-6

| Ex | Str |
|---|---|
| 101 | |
| 102 | |
| 103 | |
| 104 | |
| 105 | |
| 106 | |

TABLE 4-6-continued

| Ex | Str |
|---|---|
| 107 | |
| 108 | |
| 109 | |
| 110 | |
| 111 | |
| 112 | |

TABLE 4-6-continued

| Ex | Str |
|---|---|
| 113 | |
| 114 | |
| 115 | |
| 116 | |
| 117 | |
| 118 | |

TABLE 4-6-continued

| Ex | Str |
|---|---|
| 119 | |
| 120 | |

TABLE 4-7

| Ex | Str |
|---|---|
| 121 | |
| 122 | |
| 123 | |

101

TABLE 4-7-continued

| Ex | Str |
|----|-----|
| 124 | OH; F, O, F, F; N N N; OH Me; N H; cyclopropyl |
| 125 | OH; Cl; N N N; NH O; N H; cyclopropyl |
| 126 | OH; F, O, F, F; N N N; NH O; N H; cyclopropyl |
| 127 | OH; F, F, F; N N N; NH O; N H; cyclopropyl |
| 128 | OH; F, F, F; N N N; OH; N H; Me Me |
| 129 | OH; F, F, F; N N N; Me OH; N H; Me Me |

102

TABLE 4-7-continued

| Ex | Str |
|----|-----|
| 130 | F, F, F; OH; N N N; Me OH; N H; F, F, F |
| 131 | OH; F, O, F; N N N; OH; N H; Me |
| 132 | OH; F, F, F; N N N; NH₂; N H; Me |
| 133 | OH; F, F, F; N N N; NH; N H; Me |
| 134 | OH; F, F, F; N N N; NH; N H; pyrrolidine N H; Me |
| 135 | OH; F, F, F; N N N; N H; piperidine N H; Me |
| 136 | OH; F, F, F; N N N; NH₂; N H; Me; Me |


TABLE 4-7-continued

| Ex | Str |
|----|-----|
| 137 | |
| 138 | |
| 139 | |
| 140 | |

TABLE 4-8

| Ex | Str |
|----|-----|
| 141 | |
| 142 | |
| 143 | |

TABLE 4-8-continued

| Ex | Str |
|----|-----|
| 144 | |
| 145 | |
| 146 | |
| 147 | |
| 148 | HCl |
| 149 | |
| 150 | |
| 151 | |

TABLE 4-8-continued

| Ex | Str |
|---|---|
| 152 | |
| 153 | |
| 154 | |
| 155 | |
| 156 | |
| 157 | |
| 158 | |

TABLE 4-8-continued

| Ex | Str |
|---|---|
| 159 | |
| 160 | |

TABLE 4-9

| Ex | Str |
|---|---|
| 161 | |
| 162 | |
| 163 | |

TABLE 4-10

| Ex | Str |
|---|---|
| 164 | |
| 165 | |
| 166 | |
| 167 | |
| 168 | |
| 169 | |
| 170 | |

TABLE 4-10-continued

| Ex | Str |
|---|---|
| 171 | |
| 172 | |
| 173 | |
| 174 | |
| 175 | |
| 176 | |
| 177 | |

109

TABLE 4-10-continued

| Ex | Str |
|---|---|
| 178 | |
| 179 | |
| 180 | |
| 181 | |
| 182 | |
| 183 | |

TABLE 4-11

| Ex | Str |
|---|---|
| 184 | |

110

TABLE 4-11-continued

| Ex | Str |
|---|---|
| 185 | |
| 186 | |
| 187 | |
| 188 | |

TABLE 5-1

| PEx | PSyn | DAT |
|---|---|---|
| 1 | — | ESI+; 243, 245 |
| 2 | 1 | ESI+; 217, 219 |
| 3 | 1 | ESI+; 203, 205 |
| 4 | 1 | FAB; 203 |
| 5 | 1 | ESI+; 229, 231 |
| 6 | 1 | ESI+; 227 |
| 7 | 1 | ESI+; 249, 251 |
| 8 | 1 | ESI+; 229, 231 |
| 9 | 1 | ESI+; 231, 233 |
| 10 | 1 | ESI+; 217, 219 |
| 11 | — | ESI+; 245, 247 |
| 12 | 1 | ESI+; 277, 279 |
| 13 | 1 | ESI+; 229, 231 |
| 14 | 1 | ESI+; 217, 219 |
| 15 | 1 | ESI+; 243, 245 |
| 16 | 1 | ESI+; 231, 233 |
| 17 | 1 | ESI+; 229, 231 |
| 18 | 1 | ESI+; 229, 231 |
| 19 | 1 | ESI+; 243, 245 |
| 20 | 1 | ESI+; 245, 247 |
| 21 | 1 | ESI+: 255, 257 |
| 22 | 1 | ESI+; 229, 231 |
| 23 | 1 | ESI+; 227, 229 |
| 24 | 1 | ESI+; 243, 245 |
| 25 | 1 | ESI+: 237, 239 |
| 26 | 1 | ESI+; 231, 233 |
| 27 | 1 | ESI+; 229, 231 |

TABLE 5-1-continued

| PEx | PSyn | DAT |
|---|---|---|
| 28 | 1 | ESI+; 217, 219 |
| 29 | 1 | ESI+; 229, 231 |
| 30 | 1 | ESI+; 229, 231 |
| 31 | 1 | ESI+; 241, 243 |
| 32 | 1 | ESI+; 255, 257 |
| 33 | 1 | ESI+; 243, 245 |
| 34 | 1 | ESI+; 243, 245 |
| 35 | 1 | ESI+; 242, 244 |

TABLE 5-2

| PEx | PSyn | DAT |
|---|---|---|
| 36 | 1 | ESI+; 228, 230 |
| 37 | 1 | ESI+; 228, 230 |
| 38 | 1 | ESI+; 242, 244 |
| 39 | 1 | ESI+; 256, 258 |
| 40 | 1 | ESI+; 257, 259 |
| 41 | 1 | ESI+; 279, 281 |
| 42 | 1 | ESI+; 314 |
| 43 | 1 | ESI+; 344, 346 |
| 44 | 1 | ESI+; 265, 267 |
| 45 | 1 | ESI+; 302, 304 |
| 46 | 1 | ESI+; 214, 216 |
| 47 | 1 | ESI+; 228, 230 |
| 48 | 1 | ESI+; 229, 231 |
| 49 | 1 | ESI−; 212, 214 |
| 50 | 1 | ESI+; 228 |
| 51 | 1 | ESI+; 257, 259 |
| 52 | 1 | ESI+; 279, 281 |
| 53 | — | ESI+; 268, 270 |
| 54 | 1 | ESI+; 242, 244 |
| 55 | — | ESI+; 243, 245 |
| 56 | 1 | ESI+; 257, 259 |
| 57 | 1 | ESI−; 328, 330 |
| 58 | 1 | ESI+; 257, 259 |
| 59 | 1 | $^1$H-NMR (400 MHz, CDCl$_3$) δ ppm 1.30 (6 H, s) 2.14 (1 H, br s) 2.47 (3 H, s) 3.53 (2 H, d, J = 6.4 Hz) 5.65 (1 H, br s) |
| 60 | 1 | ESI+; 280, 282 [M + Na]+ |
| 61 | 1 | $^1$H-NMR (400 MHz, CDCl$_3$) δ ppm 2.51 (3 H, s) 3.86-3.96 (2 H, m) 5.52 (1 H, br s) 5.98 (1 H, tt, J = 4.1, 55.6 Hz) |
| 62 | 1 | ESI+; 272, 274 |
| 63 | 1 | $^1$H-NMR (400 MHz, CDCl$_3$) δ ppm 2.55 (3 H, s) 2.99 (1 H, br s) 4.03 (2 H, t, J = 4.6 Hz) 4.25 (2 H, t, J = 4.6 Hz) 7.10 (1 H, br s) 7.57 (1 H, s) 7.98 (1 H, s) |
| 64 | 1 | $^1$H-NMR (400 MHz, CDCl$_3$) δ ppm 2.56 (3 H, s) 2.94 (1 H, br s) 3.99 (2 H, br s) 4.18 (2 H, t, J = 4.6 Hz) 6.79 (1 H, d, J = 2.3 Hz) 7.38 (1 H, d, J = 2.3 Hz) 7.74 (1 H, br s) |

TABLE 5-3

| PEx | PSyn | DAT |
|---|---|---|
| 65 | 1 | ESI+; 236, 238 |
| 66 | 1 | ESI+; 225, 227 |
| 67 | 1 | ESI+; 225, 227 |
| 68 | 1 | ESI+; 258, 260 |
| 69 | 1 | ESI+; 243, 245 |
| 70 | 1 | ESI+; 225, 227 |
| 71 | 1 | ESI+; 350, 352 [M + Na]+ |
| 72 | 1 | ESI+; 364, 366 [M + Na]+ |
| 73 | — | ESI+; 364, 366 [M + Na]+ |
| 74 | 1 | ESI+; 317, 319 [M + Na]+ |
| 75 | 1 | ESI+; 251, 253 [M + Na]+ |
| 76 | 1 | ESI+; 229, 231 |
| 77 | 1 | ESI+; 317, 319 [M + Na]+ |
| 78 | 1 | EI+; 197 |
| 79 | 1 | ESI+; 291, 293 [M + Na]+ |
| 80 | 1 | ESI+; 238, 240 |
| 81 | 1 | ESI+; 352, 354 [M + Na]+ |
| 82 | 1 | ESI+; 260, 262 [M + Na]+ |
| 83 | 1 | ESI+; 350, 352 [M + Na]+ |

TABLE 5-3-continued

| PEx | PSyn | DAT |
|---|---|---|
| 84 | 1 | ESI+; 350, 352 [M + Na]+ |
| 85 | 1 | ESI+; 378, 380 [M + Na]+ |
| 86 | 1 | ESI+; 331, 333 [M + Na]+ |
| 87 | — | ESI+; 366, 368 [M + Na]+ |
| 88 | 1 | ESI+; 320, 322 [M + Na]+ |
| 89 | 1 | ESI+; 366, 368 [M + Na]+ |
| 90 | 1 | ESI+; 350, 352 [M + Na]+ |
| 91 | 1 | ESI+; 350, 352 [M + Na]+ |
| 92 | 1 | ESI+; 270, 272 |
| 93 | 1 | ESI+; 270, 272 |
| 94 | — | ESI+; 353 [M + Na]+ |
| 95 | 94 | ESI+; 283 [M + Na]+ |
| 96 | 94 | — |
| 97 | — | ESI+; 141 |
| 98 | 97 | ESI+; 130 |
| 99 | — | ESI+; 221 |

TABLE 5-4

| PEx | PSyn | DAT |
|---|---|---|
| 100 | 99 | ESI+; 235 |
| 101 | 99 | ESI+; 221 |
| 102 | 99 | ESI+; 237 |
| 103 | 99 | ESI+; 245 |
| 104 | 99 | ESI+; 249 |
| 105 | — | ESI+; 299 |
| 106 | 105 | ESI+; 315 |
| 107 | 105 | ESI+; 301 |
| 108 | 105 | ESI+; 315 |
| 109 | 105 | ESI+; 325 |
| 110 | 105 | ESI+; 327 |
| 111 | 105 | ESI+; 300 |
| 112 | 105 | ESI+; 243, 245 |
| 113 | 105 | ESI+; 349, 351 |
| 114 | 105 | ESI+; 315, 317 |
| 115 | 105 | ESI+; 275, 277 |
| 116 | 105 | ESI+; 301, 303 |
| 117 | — | ESI+; 468 |
| 118 | 117 | ESI+; 440 |
| 119 | 117 | ESI+; 470 |
| 120 | 117 | ESI+; 428 |
| 121 | 117 | ESI+; 456 |
| 122 | 117 | ESI+; 468 |
| 123 | 117 | ESI+; 454 |
| 124 | 117 | ESI+; 468 |
| 125 | 117 | ESI+; 421 |
| 126 | 117 | ESI+; 443 [M + Na]+ |
| 127 | 117 | ESI+; 456 |
| 128 | 117 | ESI+; 454 |
| 129 | 117 | ESI+; 454 |
| 130 | 117 | ESI+; 504 [M + Na]+ |
| 131 | 117 | ESI+; 435 |
| 132 | — | ESI+; 470 |
| 133 | 117 | ESI+; 492 [M + Na]+ |
| 134 | 117 | ESI+; 476 [M + Na]+ |

TABLE 5-5

| PEx | PSyn | DAT |
|---|---|---|
| 135 | 117 | ESI+; 454 |
| 136 | 117 | ESI+; 484 |
| 137 | 117 | ESI+; 434, 436 |
| 138 | 117 | ESI+; 414 |
| 139 | — | ESI+; 370 |
| 140 | 139 | ESI+; 368 |
| 141 | — | ESI−; 259 |
| 142 | — | ESI+; 178 |
| 143 | — | ESI+; 241 |
| 144 | — | ESI+; 200 |
| 145 | — | ESI+; 220 |
| 146 | 145 | ESI+; 165 |

TABLE 5-5-continued

| PEx | PSyn | DAT |
|-----|------|-----|
| 147 | 145 | ESI+; 271 |
| 148 | 145 | ESI+; 237 |
| 149 | 145 | ESI+; 197 |
| 150 | — | FAB; 356 |
| 151 | — | FAB; 440 |
| 152 | — | ESI+; 238 [M + Na]+ |
| 153 | — | ESI+; 254 [M + Na]+ |
| 154 | — | ESI+; 259, 261 |
| 155 | — | CI; 283 |
| 156 | — | ESI+; 410 |
| 157 | — | ESI+; 223 |
| 158 | — | ESI+; 226 [M + Na]+ |
| 159 | — | $^1$H-NMR (400 MHz, CDCl$_3$) δ ppm 1.03 (3 H, d, J = 6.9 Hz) 1.46 (9 H, s) 1.60-1.69 (2 H, m) 1.91-2.01 (1 H, m) 3.02 (3 H, s) 3.11-3.24 (2 H, m) 4.05-4.11 (2 H, m) 4.55 (1 H, br s) |
| 160 | — | ESI+; 251 [M + Na]+ |
| 161 | — | $^1$H-NMR (400 MHz, CDCl$_3$) δ ppm 0.93 (3 H, d, J = 6.4 Hz) 1.26-1.35 (1 H, m) 1.44 (9 H, s) 1.49-1.62 (2 H, m) 2.52-2.57 (1 H, m) 2.60-2.65 (1 H, m) 3.07-3.21 (2 H, m) 4.73 (1 H, br s) |
| 162 | — | ESI+; 293 [M + Na]+ |
| 163 | 162 | ESI+; 243 |

TABLE 5-6

| PEx | PSyn | DAT |
|-----|------|-----|
| 164 | 162 | $^1$H-NMR (400 MHz, CDCl$_3$) δ ppm 1.43 (9 H, s) 1.96-2.05 (5 H, m) 2.09-2.18 (2 H, m) 2.32-2.40 (1 H, m) 3.32-3.35 (2 H, m) 4.17-4.23 (1 H, m) 4.71-4.72 (1 H, m) 5.50 (1 H, br s) |
| 165 | — | ESI+; 111 |
| 166 | 165 | ESI+; 171 |
| 167 | 165 | ESI+; 143 |
| 168 | 165 | ESI+; 143 |

TABLE 5-7

| PEx | PSyn | DAT |
|-----|------|-----|
| 169 | — | ESI+; 242, 244 |
| 170 | 1 | ESI+; 243, 245 |
| 171 | 1 | ESI+; 243, 245 |
| 172 | 1 | ESI+; 376, 378 [M + Na]+ |
| 173 | 1 | ESI+; 358, 360 |
| 174 | 1 | ESI+; 386, 388 [M + Na]+ |
| 175 | 1 | ESI+; 386, 388 |
| 176 | 1 | ESI+; 271, 273 |
| 177 | 94 | EI+; 350 |
| 178 | 94 | EI+; 314 |
| 179 | 105 | ESI+; 287 |
| 180 | — | ESI+; 410 |
| 181 | 117 | ESI+; 395 |
| 182 | 117 | ESI+; 431 |
| 183 | 117 | ESI+; 480 |
| 184 | 117 | ESI+; 484 |
| 185 | 117 | ESI+; 490 |
| 186 | 117 | ESI+; 512 |
| 187 | 117 | ESI+; 397 |
| 188 | 139 | ESI+; 390 |
| 189 | 145 | ESI+; 209 |
| 190 | — | EI+; 244 |
| 191 | 190 | EI+; 302 |
| 192 | — | EI+; 266 |
| 193 | — | ESI+; 509 |
| 194 | — | ESI+; 519 [M + Na]+ |
| 195 | — | ESI−; 496 |
| 196 | — | ESI+; 482 |
| 197 | — | ESI+; 496 |

TABLE 6-1

| Ex | Syn | DAT |
|----|-----|-----|
| 1 | — | ESI+; 369 |
| 2 | 1 | ESI+; 343 |
| 3 | 1 | FAB; 329 |
| 4 | 1 | FAB; 329 |
| 5 | 1 | ESI+; 355 |
| 6 | 1 | FAB; 353 |
| 7 | 1 | ESI+; 375 |
| 8 | 1 | ESI+; 355 |
| 9 | 1 | ESI+; 357 |
| 10 | 1 | ESI+; 343 |
| 11 | 1 | ESI+; 371 |
| 12 | 1 | ESI+; 403 |
| 13 | 1 | ESI+; 355 |
| 14 | 1 | ESI+; 343 |
| 15 | 1 | ESI+; 369 |
| 16 | 1 | ESI+; 357 |
| 17 | 1 | ESI+; 355 |
| 18 | 1 | ESI+; 355 |
| 19 | 1 | FAB; 335 |
| 20 | 1 | ESI+; 369 |
| 21 | 1 | ESI+; 371 |
| 22 | 1 | ESI+; 381 |
| 23 | 1 | ESI+; 355 |
| 24 | 1 | ESI+; 353 |
| 25 | 1 | FAB; 326 |
| 26 | 1 | ESI+; 369 |
| 27 | — | ESI+; 385 $^1$H NMR (500 MHz, DMSO-d$_6$) δ ppm 1.17-1.33 (4 H, m) 1.59-1.70 (2 H, m) 1.86-2.03 (2 H, m) 2.17 (3 H, s) 3.38-3.47 (1 H, m) 3.65-3.81 (1 H, m) 4.61 (1 H, d, J = 5.0 Hz) 6.84-6.94 (2 H, m) 7.26-7.42 (2 H, m) 10.43 (1 H, br s) |
| 28 | 1 | ESI+; 363 |
| 29 | 1 | ESI+; 357 |
| 30 | 1 | ESI+; 355 |

TABLE 6-2

| Ex | Syn | DAT |
|----|-----|-----|
| 31 | — | ESI+; 337, 339 $^1$H NMR (500 MHz, DMSO-d$_6$) δ ppm 1.48-1.58 (1 H, m) 1.90-2.01 (1 H, m) 2.17 (3 H, s) 3.03-3.10 (1 H, m) 3.33-3.41 (1 H, m) 3.47-3.56 (1 H, m) 3.78-3.86 (2 H, m) 3.88-3.98 (1 H, m) 4.96 (1 H, d, J = 5.4 Hz) 6.96-6.99 (2 H, m) 7.24-7.28 (1 H, m) 7.38-7.66 (1 H, m) 10.30 (1 H, br s) |
| 32 | 1 | ESI+; 387 |
| 33 | 1 | ESI+; 343 |
| 34 | 1 | ESI+; 355 |
| 35 | 1 | ESI+; 355 |
| 36 | 1 | FAB; 343 |
| 37 | 1 | FAB; 315 |
| 38 | 1 | ESI+; 367 |
| 39 | 1 | ESI+; 381 |
| 40 | 1 | ESI+; 369 |
| 41 | 1 | ESI+; 369 |
| 42 | 1 | ESI+; 368 |
| 43 | 1 | ESI+; 354 |
| 44 | 1 | ESI+; 354 |
| 45 | 1 | ESI+; 368 |
| 46 | 1 | ESI+; 382 |
| 47 | 1 | ESI+; 383 |
| 48 | 1 | ESI+; 405 |
| 49 | 1 | ESI+; 321, 323 |
| 50 | 1 | ESI+; 371 |
| 51 | 1 | ESI+; 301 |
| 52 | 1 | ESI+; 317 |
| 53 | 1 | ESI+; 319 |
| 54 | 1 | ESI+; 349, 351 |
| 55 | 1 | ESI+; 329 |
| 56 | 1 | ESI+; 301 |
| 57 | 1 | FAB; 391 |
| 58 | 1 | ESI+; 399 |

TABLE 6-3

| Ex | Syn | DAT |
|---|---|---|
| 59 | — | ESI+; 331<br>¹H NMR (500 MHz, DMSO-d₆) δ ppm 1.17-1.32 (4 H, m) 1.58-1.70 (2 H, m) 1.86-1.94 (1 H, m) 1.94-2.03 (1 H, m) 2.17 (3 H, s) 3.36-3.46 (1 H, m) 3.64-3.79 (4 H, m) 4.60 (1 H, d, J = 4.9 Hz) 6.47-6.53 (2 H, m) 7.06-7.26 (2 H, m) 9.80 (1 H, s) |
| 60 | 1 | ESI+; 317 |
| 61 | 1 | ESI+; 333 |
| 62 | 1 | ESI+; 340 |
| 63 | 1 | ESI+; 354 |
| 64 | 1 | ESI+; 355 |
| 65 | 1 | ESI+; 340 |
| 66 | 1 | ESI+; 354 |
| 67 | 1 | ESI+; 341 |
| 68 | 1 | ESI+; 383 |
| 69 | 1 | ESI+; 405 |
| 70 | 1 | ESI+; 320, 322 |
| 71 | 1 | ESI+; 300 |
| 72 | 1 | ESI+; 370 |
| 73 | — | ESI+; 394<br>¹H NMR (500 MHz, DMSO-d₆) δ ppm 0.26-0.36 (2 H, m) 0.36-0.45 (2 H, m) 1.31-1.51 (2 H, m) 1.60-1.70 (2 H, m) 1.80-1.91 (1 H, m) 2.09-2.22 (5 H, m) 2.77-2.84 (1 H, m) 3.01-3.14 (1 H, m) 3.80-4.04 (1 H, m) 7.22 (1 H, d, J = 1.0 Hz) 7.26 (1 H, dd, J = 7.9, 1.0 Hz) 7.30-7.85 (2 H, m) 10.50 (1 H, br s) |
| 74 | 1 | ESI+; 368 |
| 75 | — | ESI+; 369<br>¹H NMR (500 MHz, DMSO-d₆) δ ppm 1.03-1.34 (4 H, m) 1.67-1.75 (1 H, m) 1.77-1.91 (2 H, m) 2.07-2.15 (1 H, m) 2.18 (3 H, s) 3.43-3.54 (1 H, m) 3.74-3.98 (1 H, m) 4.66 (1 H, d, J = 4.6 Hz) 7.22 (1 H, d, J = 1.0 Hz) 7.24-7.28 (1 H, m) 7.36-7.90 (2 H, m) 10.51 (1 H, br s) |
| 76 | 1 | ESI+; 383 |

TABLE 6-4

| Ex | Syn | DAT |
|---|---|---|
| 77 | 1 | ESI+; 327 |
| 78 | 1 | ESI+; 343 |
| 79 | 1 | ESI+; 383 |
| 80 | 1 | ESI+; 385 |
| 81 | 1 | ESI+; 315 |
| 82 | 1 | ESI+; 335, 337 |
| 83 | 1 | ESI+; 341 |
| 84 | 1 | ESI+; 385 |
| 85 | 1 | ESI+; 343 |
| 86 | 1 | ESI+; 384 |
| 87 | 1 | ESI+; 335 |
| 88 | 1 | ESI+; 398 |
| 89 | 1 | ESI+; 381 |
| 90 | 1 | ESI+; 381 |
| 91 | 1 | ESI+; 325 |
| 92 | 1 | ESI+; 362 |
| 93 | 1 | ESI+; 351 |
| 94 | 1 | ESI+; 351 |
| 95 | 1 | ESI+; 384 |
| 96 | 1 | ESI+; 369 |
| 97 | 1 | ESI+; 351 |
| 98 | 1 | ESI+; 431 |
| 99 | 1 | ESI+; 355 |
| 100 | 1 | ESI+; 355 |
| 101 | 1 | ESI+; 324 |
| 102 | 1 | ESI+; 364 |
| 103 | 1 | ESI+; 364 |
| 104 | 1 | ESI+; 424 |
| 105 | 1 | ESI+; 396 |
| 106 | 1 | ESI+; 396 |
| 107 | 1 | ESI+; 395 |

TABLE 6-5

| Ex | Syn | DAT |
|---|---|---|
| 108 | — | ESI+; 381<br>¹H NMR (500 MHz, DMSO-d₆) δ ppm 0.94-1.07 (4 H, m) 1.27 (3 H, s) 1.60-1.67 (1 H, m) 2.00-2.07 (2 H, m) 2.29-2.38 (2 H, m) 3.64-4.06 (1 H, m) 4.94 (1 H, s) 7.20-7.23 (1 H, m) 7.24-7.28 (1 H, m) 7.40-8.20 (2 H, m) 10.45 (1 H, br s) |
| 109 | 108 | ESI+; 395 |
| 110 | 108 | ESI+; 381 |
| 111 | 108 | ESI+; 397 |
| 112 | 108 | ESI+; 413 |
| 113 | 108 | ESI+; 363, 365 |
| 114 | 108 | ESI+; 343 |
| 115 | 108 | ESI+; 361, 363 |
| 116 | 108 | ESI+; 411 |
| 117 | 108 | ESI+; 341 |
| 118 | 108 | ESI+; 405 |
| 119 | 108 | ESI+; 327 |
| 120 | 108 | ESI+; 397 |
| 121 | 108 | ESI+; 347, 349 |
| 122 | 108 | ESI+; 409 |
| 123 | 108 | ESI+; 375, 377 |
| 124 | 108 | ESI+; 425 |
| 125 | 108 | ESI+; 346, 348 |
| 126 | 108 | ESI+; 396 |
| 127 | 108 | ESI+; 380 |
| 128 | 108 | ESI+; 397 |
| 129 | 108 | ESI+; 357 |
| 130 | 108 | ESI+; 383 |
| 131 | — | ESI+; 367<br>¹H NMR (500 MHz, DMSO-d₆) δ ppm 1.14-1.34 (4 H, m) 1.56-1.72 (2 H, m) 1.86-2.02 (2 H, m) 2.17 (3 H, s) 3.37-3.47 (1 H, m) 3.64-3.81 (1 H, m) 4.60 (1 H, d, J = 5.0 Hz) 6.69-6.75 (2 H, m) 7.09-7.41 (3 H, m) 10.21 (1 H, br s) |

TABLE 6-6

| Ex | Syn | DAT |
|---|---|---|
| 132 | — | ESI+; 368<br>¹H-NMR (400 MHz, CDCl₃) δ ppm 1.13-1.44 (4 H, m) 1.68-1.71 (2 H, m) 1.96-2.01 (2 H, m) 2.27 (3 H, s) 2.98-3.15 (1 H, m) 3.87-4.05 (1 H, m) 7.20 (1 H, d, J = 8.4 Hz) 7.30-7.33 (2 H, m) |
| 133 | 132 | ESI+; 340 |
| 134 | 132 | ESI+; 354 |
| 135 | 132 | ESI+; 368 |
| 136 | 132 | ESI+; 356 |
| 137 | 132 | ESI+; 354 |
| 138 | 132 | ESI+; 354 |
| 139 | 132 | ESI+; 382 |
| 140 | 132 | ESI+; 351 |
| 141 | — | ESI+; 370<br>¹H-NMR (400 MHz, CD₃OD) δ ppm 2.31 (3 H, s) 2.72-2.78 (1 H, m) 2.91-2.99 (2 H, m) 3.12-3.16 (1 H, m) 3.53-3.63 (2 H, m) 3.66-3.73 (1 H, m) 3.81-3.86 (1 H, m) 3.96-3.99 (1 H, m) 7.18 (1 H, s) 7.26 (1 H, dd, J = 0.9, 7.8 Hz) 7.46 (1 H, d, J = 7.8 Hz) |
| 142 | 132 | ESI+; 370 |
| 143 | 132 | ESI+; 354 |
| 144 | 132 | ESI+; 354 |
| 145 | 132 | ESI+; 384 |
| 146 | 132 | ESI+; 334, 336 |
| 147 | 132 | ESI+; 314 |
| 148 | — | ESI+; 328 |
| 149 | — | ESI+; 337 |
| 150 | 149 | ESI+; 337 |
| 151 | — | ESI+; 396 |
| 152 | — | ESI+; 410 |
| 153 | 152 | ESI+; 410 |
| 154 | 152 | ESI+; 396 |
| 155 | 152 | ESI+; 412 |
| 156 | 152 | ESI+; 396 |
| 157 | 152 | ESI+; 396 |

TABLE 6-7

| Ex | Syn | DAT |
|-----|------|-----------|
| 158 | 152 | ESI+; 412 |
| 159 | — | ESI+; 412 |
| 160 | — | FAB; 434 |
| 161 | — | ESI+; 384 |
| 162 | 161 | ESI+; 370 |
| 163 | — | FAB; 398 |

TABLE 6-8

| Ex | Syn | DAT |
|-----|------|-----------|
| 164 | — | ESI+; 368<br>$^1$H NMR (500 MHz, DMSO-d$_6$) δ ppm 1.25-1.38 (1 H, m) 1.47-1.60 (1 H, m) 1.65-1.75 (1 H, m) 1.79-1.94 (3 H, m) 2.13-2.26 (6 H, m) 2.58-2.69 (1 H, m) 2.80-2.95 (1 H, m) 3.90-4.11 (1 H, m) 7.21-7.24 (1 H, m) 7.24-7.29 (1 H, m) 7.32-7.90 (2 H, m) 10.52 (1 H, br s) |
| 165 | 1 | ESI+; 383 |
| 166 | 1 | ESI+; 369 |
| 167 | 1 | ESI+; 369 |

TABLE 6-8-continued

| Ex | Syn | DAT |
|-----|------|-----------|
| 168 | 108 | ESI+; 331 |
| 169 | 131 | ESI+; 387 |
| 170 | 132 | ESI+; 380 |
| 171 | 132 | ESI+; 384 |
| 172 | 132 | ESI+; 409 |
| 173 | 132 | ESI+; 397 |
| 174 | — | ESI+; 366<br>$^1$H NMR (500 MHz, DMSO-d$_6$) δ ppm 1.24-1.37 (1 H, m) 1.46-1.60 (1 H, m) 1.64-1.75 (1 H, m) 1.78-1.95 (3 H, m) 2.14-2.22 (6 H, m) 2.57-2.69 (1 H, m) 2.78-2.97 (1 H, m) 3.87-4.10 (1 H, m) 6.68-6.80 (2 H, m) 7.07-7.60 (3 H, m) 10.21 (1 H, br s) |
| 175 | 174 | ESI+; 351 |
| 176 | 174 | ESI+; 387 |
| 177 | 161 | ESI+; 396 |
| 178 | 161 | ESI+; 408 |
| 179 | 161 | ESI+; 410 |
| 180 | 161 | ESI+; 404 |
| 181 | — | ESI+; 407 |
| 182 | — | ESI+; 383 |
| 183 | 182 | ESI+; 412 |

TABLE 6-9

| Ex | Syn | DAT |
|-----|------|-----------|
| 184 | — | ESI+; 331<br>$^1$H NMR (500 MHz, CD$_3$OD) δ ppm 1.28-1.58 (4 H, m) 1.70-1.90 (2 H, m) 1.97-2.14 (2 H, m) 2.53 (3 H, s) 3.47-3.79 (2 H, m) 3.82 (3 H, s) 6.51 (1 H, d, J = 2.3 Hz) 6.58 (1 H, dd, J = 8.5, 2.4 Hz) 7.22 (1 H, d, J = 8.4 Hz)<br>2θ(°) = 8.4, 13.8, 14.5, 16.2, 17.5, 20.1, 21,1, 22.6, 23.6, 25.3<br>m.p.; 184.75° C. |
| 185 | — | ESI+; 369<br>$^1$H NMR (500 MHz, DMSO-d$_6$) δ ppm 1.03-1.14 (1 H, m) 1.14-1.35 (3 H, m) 1.67-1.76 (1 H, m) 1.76-1.92 (2 H, m) 2.05-2.18 (1 H, m) 2.23 (3 H, s) 3.42-3.95 (3 H, m) 7.23-7.31 (2 H, m) 7.49 (1 H, d, J = 7.6 Hz) 8.12 (1 H, br s) 10.67 (1 H, br s)<br>2θ(°) = 5.8, 9.5, 12.6, 13.5, 14.4, 14.8, 16.3, 17.1, 18.3, 23.3<br>m.p.; 158.63° C. |
| 186 | — | ESI+, 367<br>$^1$H NMR (500 MHz, CD$_3$OD) δ ppm 1.30-1.57 (4 H, m) 1.74-1.87 (2 H, m) 1.98-2.12 (2 H, m) 2.52 (3 H, s) 3.47-3.78 (2 H, m) 6.79 (1 H, dd, J = 8.4, 2.3 Hz) 6.72-7.05 (2 H, m) 7.34 (1 H, d, J = 8.4 Hz)<br>2θ(°) = 8.9, 9.5, 15.3, 18.2, 19.8, 20.7, 21.5, 21.8, 25.1, 27.0<br>m.p.; 153.32° C. |
| 187 | — | ESI+; 368<br>$^1$H NMR (500 MHz, CD$_3$OD) δ ppm 1.67-1.82 (1 H, m) 1.90-2.19 (2 H, m) 2.19-2.29 (1 H, m) 2.51 (3 H, s) 2.87-3.18 (5 H, m) 3.50-3.61 (1 H, m) 3.71-3.89 (1 H, m) 4.30-4.60 (1 H, m) 7.21-7.26(1 H, m) 7.28-7.33(1 H, m) 7.52 (1 H, d, J = 7.8 Hz)<br>2θ(°) = 5.2, 9.6, 13.0, 15.4, 15.9, 17.9, 20.2, 20.9, 23.9, 29.0 |
| 188 | — | ESI+; 368<br>$^1$H-NMR. (400 MHz, DMSO-d$_6$) δ ppm 1.24-1.31 (2 H, m) 1.37-1.48 (2 H, m) 1.73-1.76 (2 H, m) 1.99-2.09 (2 H, m) 2.24 (3 H, s) 3.04-3.11 (1 H, m) 3.97-4.16 (1 H, m) 7.28-7.29 (2 H, m) 7.48 (1 H, d, J = 8.3 Hz) 7.63 (1 H, br s) 7.95 (3 H, br s) 10.71 (1 H, br s)<br>2θ(°) = 5.9, 8.6, 15.5, 17.6, 21.6, 23.8, 24.8, 27.4, 28.6, 31.4 |

INDUSTRIAL APPLICABILITY

The compound of formula (I) or a salt thereof has an inhibitory effect on NLRP3 inflammasome activation and expected to be used as a preventive and/or therapeutic drug for an inflammatory disease and/or a neurodegenerative disease.

The invention claimed is:

1. A compound of formula (I) or a salt thereof (I)

wherein,

R$^1$ are the same or different from each other, and are C$_{1-6}$ alkyl, halogeno-C$_{1-6}$ alkyl, C$_{3-8}$ cycloalkyl, halogen, —O—C$_{1-6}$ alkyl, —O-halogeno-C$_{1-6}$ alkyl or cyano, R$^2$ is C$_{1-6}$ alkyl, C$_{3-8}$ cycloalkyl, halogeno-C$_{1-6}$ alkyl, —O—C$_{1-6}$ alkyl, —N(C$_{1-6}$ alkyl)$_2$ or aryl, R$^3$ is H or C$_{1-6}$ alkyl, R$^4$ is C$_{1-6}$ alkyl substituted with the same or different one to four R$^5$, —C$_{1-6}$ alkylene-(aryl optionally substituted with the same or different one to four R$^6$), —C$_{1-6}$ alkylene-(C$_{3-8}$ cycloalkyl optionally substituted with the same or different one to four R$^7$), —C$_{1-6}$ alkylene-(heteroaryl optionally substituted with the same or different one to four R$^8$), —C$_{1-6}$ alkylene-(4 to 7-membered saturated heterocyclyl optionally substituted with the same or different one to four R$^9$), C$_{3-8}$ cycloalkyl optionally substituted with the same or different one to four R$^{10}$, heteroaryl optionally substituted with the same or different one to four R$^{11}$, or a 4 to 7-membered saturated heterocyclyl optionally substituted with the same or different one to four R$^{12}$, R$^5$ is —OR$^{13}$, —NR$^{14}$R$^{15}$, halogen or cyano, R$^6$ is C$_{1-6}$ alkyl, halogeno-C$_{1-6}$ alkyl, C$_{3-8}$ cycloalkyl, —OR$^{13}$, —NR$^{14}$R$^{15}$, —C$_{1-6}$ alkylene-OR$^{13}$, —C$_{1-6}$ alkylene-NR$^{14}$R$^{15}$, halogen or cyano, R$^7$ is C$_{1-6}$ alkyl, halogeno-C$_{1-6}$ alkyl, C$_{3-8}$ cycloalkyl, —OR$^{13}$, —NR$^{14}$R$^{15}$, —C$_{1-6}$ alkylene-OR$^{13}$, —C$_{1-6}$ alkylene-NR$^{14}$R$^{15}$, halogen or cyano, R$^8$ is C$_{1-6}$ alkyl, halogeno-C$_{1-6}$ alkyl, C$_{3-8}$ cycloalkyl, —OR$^{13}$, —NR$^{14}$R$^{15}$, —C$_{1-6}$ alkylene-OR$^{13}$, —C$_{1-6}$ alkylene-NR$^{14}$R$^{15}$, halogen or cyano, R$^9$ is C$_{1-6}$ alkyl, halogeno-C$_{1-6}$ alkyl, C$_{3-8}$ cycloalkyl, —OR$^{13}$, —NR$^{14}$R$^{15}$, —C$_{1-6}$ alkylene-OR$^{13}$, —C$_{1-6}$ alkylene-NR$^{14}$R$^{15}$, halogen, cyano, oxo, —C(O)—C$_{1-6}$ alkyl or —S(O)$_2$—C$_{1-6}$ alkyl, R$^{10}$ is C$_{1-6}$ alkyl, halogeno-C$_{1-6}$ alkyl, C$_{3-8}$ cycloalkyl, —OR$^{13}$, —NR$^{14}$R$^{15}$, —C$_{1-6}$ alkylene-OR$^{13}$, —C$_{1-6}$ alkylene-NR$^{14}$R$^{15}$, halogen or cyano, R$^{11}$ is C$_{1-6}$ alkyl, halogeno-C$_{1-6}$ alkyl, C$_{3-8}$ cycloalkyl, —OR$^{13}$, —NR$^{14}$R$^{15}$, —C$_{1-6}$ alkylene-OR$^{13}$, —C$_{1-6}$ alkylene-NR$^{14}$R$^{15}$, halogen or cyano, R$^{12}$ is C$_{1-6}$ alkyl, halogeno-C$_{1-6}$ alkyl, C$_{3-8}$ cycloalkyl, —OR$^{13}$, —NR$^{14}$R$^{15}$, —C$_{1-6}$ alkylene-OR$^{13}$, —C$_{1-6}$ alkylene-NR$^{14}$R$^{15}$, halogen, cyano, oxo, —C(O)—C$_{1-6}$ alkyl or —S(O)$_2$—C$_{1-6}$ alkyl, R$^{13}$ is H or C$_{1-6}$ alkyl, R$^{14}$ and R$^{15}$ are the same or different from each other, and are H, C$_{1-6}$ alkyl or —C(O)—C$_{1-6}$ alkyl, and n is an integer of 1 to 4, which represents the number of R$^1$ substituents.

2. The compound or a salt thereof according to claim 1, wherein the formula (I) is formula (Ia):

(Ia)

wherein,

R$^{1a}$ is C$_{1-6}$ alkyl, halogeno-C$_{1-6}$ alkyl, C$_{3-8}$ cycloalkyl, halogen, —O—C$_{1-6}$ alkyl, —O-halogeno-C$_{1-6}$ alkyl or cyano, R$^{1b}$ are the same or different from each other, and are C$_{1-6}$ alkyl, halogeno-C$_{1-6}$ alkyl or halogen, R$^2$ is C$_{1-6}$ alkyl, C$_{3-8}$ cycloalkyl, halogeno-C$_{1-6}$ alkyl, —N(C$_{1-6}$ alkyl)$_2$ or aryl, R$^3$ is H, R$^4$ is C$_{1-6}$ alkyl substituted with the same or different one to four R$^5$, —C$_{1-6}$ alkylene-(aryl optionally substituted with the same or different one to four R$^6$), —C$_{1-6}$ alkylene-(C$_{3-8}$ cycloalkyl optionally substituted with the same or different one to four R$^7$), —C$_{1-6}$ alkylene-heteroaryl, —C$_{1-6}$ alkylene-(4 to 7-membered saturated heterocyclyl optionally substituted with the same or different one to four R$^9$), C$_{3-8}$ cycloalkyl optionally substituted with the same or different one to four R$^{10}$, heteroaryl or 4 to 7-membered saturated heterocyclyl optionally substituted with the same or different one to four R$^{12}$, R$^5$ is —OR$^{13}$, —NR$^{14}$R$^{15}$, halogen or cyano, R$^6$ is —OR$^{13}$, R$^7$ is —OR$^{13}$, —NR$^{14}$R$^{15}$, —C$_{1-6}$ alkylene-OR$^{13}$ or —C$_{1-6}$ alkylene-NR$^{14}$R$^{15}$, R$^9$ is —C(O)—C$_{1-6}$ alkyl, R$^{10}$ is C$_{1-6}$ alkyl, —OR$^{13}$, —NR$^{14}$R$^{15}$, —C$_{1-6}$ alkylene-OR$^{13}$, —C$_{1-6}$ alkylene-NR$^{14}$R$^{15}$, halogen or cyano, R$^{12}$ is C$_{1-6}$ alkyl, halogeno-C$_{1-6}$ alkyl, C$_{3-8}$ cycloalkyl, —OR$^{13}$, —NR$^{14}$R$^{15}$, —C$_{1-6}$ alkylene-OR$^{13}$, —C$_{1-6}$ alkylene-NR$^{14}$R$^{15}$, halogen, cyano, oxo, —C(O)—C$_{1-6}$ alkyl or —S(O)$_2$—C$_{1-6}$ alkyl, R$^{13}$ is H or C$_{1-6}$ alkyl, R$^{14}$ and R$^{15}$ are the same or different from each other, and are H, C$_{1-6}$ alkyl or —C(O)—C$_{1-6}$ alkyl, and k is 0 or 1, which represents the number of R$^{1b}$ substituents.

3. The compound or a salt thereof according to claim 2, wherein

R$^{1a}$ is C$_{1-6}$ alkyl, halogeno-C$_{1-6}$ alkyl, C$_{3-8}$ cycloalkyl, halogen, —O—C$_{1-6}$ alkyl or —O-halogeno-C$_{1-6}$ alkyl, R$^2$ is C$_{1-6}$ alkyl or C$_{3-8}$ cycloalkyl, R$^4$ is —C$_{1-6}$ alkylene-(C$_{3-8}$ cycloalkyl optionally substituted with the same or different one to four R$^7$), —C$_{1-6}$ alkylene-(4 to 7-membered saturated heterocyclyl optionally substituted with the same or different one to four R$^9$), C$_{3-8}$ cycloalkyl optionally substituted with the same or different one to four R$^{10}$, or a 4 to 7-membered saturated heterocyclyl optionally substituted with the same or different one to four $R^{12}$, and k represents 0.

4. The compound or a salt thereof according to claim 1, wherein the compound is selected from the group consisting of 2-(3-{[(1R,2R)-2-hydroxycyclohexyl] amino}-5-methyl-1,2,4-triazin-6-yl)-5-(trifluoromethoxy) phenol, (3S,4R)-4-{[6-(4-chloro-2-hydroxyphenyl)-5-methyl-1,2,4-triazin-3-yl]amino}oxan-3-ol, 2-(5-cyclopropyl-3-{[(1s,3s)-3-hydroxy-3-methylcyclobutyl]amino}-1,2,4-triazin-6-yl)-5-(trifluoromethyl) phenol, 2-(3-{[(1R,2R)-2-hydroxycyclohexyl]amino}-5-methyl-1,2,4-triazin-6-yl)-5-methoxyphenol, 2-(3-{[(3R)-1-cyclopropylpiperidin-3-yl]amino}-5-methyl-1,2,4-triazin-6-yl)-5-(trifluoromethyl) phenol, 2-(3-{[(1R,3S)-3-hydroxycyclohexyl]amino}-5-methyl-1,2,4-triazin-6-yl)-5-(trifluoromethyl) phenol, 5-(difluoromethoxy)-2-(3-{[(1R,2R)-2-hydroxycyclohexyl]amino}-5-methyl-1,2,4-triazin-6-yl) phenol, 2-(3-{[(1R,2R)-2-aminocyclohexyl]amino}-5-methyl-1,2,4-triazin-6-yl)-5-(trifluoromethyl) phenol, and 2-[5-methyl-3-({[(2R)-morpholin-2-yl]methyl}amino)-1,2,4-triazin-6-yl]-5-(trifluoromethyl)phenol.

5. A pharmaceutical composition comprising the compound or a salt thereof according to claim 1 and one or more pharmaceutically acceptable excipients.

6. The compound or a salt thereof according to claim 1, wherein $R^2$ is $C_{1-6}$ alkyl.

7. The compound or a salt thereof according to claim 1, wherein $R^4$ is 4 to 7-membered saturated heterocyclyl optionally substituted with the same or different one to two $R^{12}$.

8. The compound or a salt thereof according to claim 7, wherein $R^4$ is 4 to 7-membered saturated heterocyclyl optionally substituted with one $R^{12}$.

* * * * *